US012226429B2

(12) United States Patent
Sommadossi et al.

(10) Patent No.: US 12,226,429 B2
(45) Date of Patent: *Feb. 18, 2025

(54) HIGHLY ACTIVE COMPOUNDS AGAINST COVID-19

(71) Applicant: Atea Pharmaceuticals, Inc., Boston, MA (US)

(72) Inventors: Jean-Pierre Sommadossi, Boston, MA (US); Adel Moussa, Burlington, MA (US)

(73) Assignee: Atea Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/225,452

(22) Filed: Jul. 24, 2023

(65) Prior Publication Data

US 2024/0238324 A1 Jul. 18, 2024

Related U.S. Application Data

(63) Continuation of application No. 17/094,541, filed on Nov. 10, 2020, now Pat. No. 11,707,480, which is a continuation of application No. 17/017,443, filed on Sep. 10, 2020, now Pat. No. 10,874,687.

(60) Provisional application No. 62/982,670, filed on Feb. 27, 2020, provisional application No. 62/994,206, filed on Mar. 24, 2020, provisional application No. 63/032,247, filed on May 29, 2020, provisional application No. 63/039,352, filed on Jun. 15, 2020, provisional application No. 63/040,985, filed on Jun. 18, 2020, provisional application No. 63/054,680, filed on Jul. 21, 2020, provisional application No. 63/073,328, filed on Sep. 1, 2020.

(51) Int. Cl.
| | | |
|---|---|---|
| A61K 31/7076 | (2006.01) | |
| A61K 9/00 | (2006.01) | |
| A61K 9/08 | (2006.01) | |
| A61K 9/20 | (2006.01) | |
| A61K 31/706 | (2006.01) | |
| A61K 31/7064 | (2006.01) | |
| A61P 31/14 | (2006.01) | |

(52) U.S. Cl.
CPC ........ *A61K 31/7076* (2013.01); *A61K 9/0019* (2013.01); *A61K 9/0053* (2013.01); *A61K 9/08* (2013.01); *A61K 9/2013* (2013.01); *A61K 9/2018* (2013.01); *A61K 9/2054* (2013.01); *A61K 31/706* (2013.01); *A61K 31/7064* (2013.01); *A61P 31/14* (2018.01)

(58) Field of Classification Search
None
See application file for complete search history.

(56) References Cited

U.S. PATENT DOCUMENTS

| | | | |
|---|---|---|---|
| 5,977,061 | A | 11/1999 | Holy et al. |
| 6,348,587 | B1 | 2/2002 | Schinazi et al. |
| 6,602,999 | B1 | 8/2003 | Kumar et al. |
| 6,660,721 | B2 | 12/2003 | Devos et al. |
| 6,777,395 | B2 | 8/2004 | Bhat et al. |
| 6,784,166 | B2 | 8/2004 | Devos et al. |
| 6,812,219 | B2 | 11/2004 | LaColla et al. |
| 6,908,924 | B2 | 6/2005 | Watanabe et al. |
| 6,911,424 | B2 | 6/2005 | Schinazi et al. |
| 6,914,054 | B2 | 7/2005 | Sommadossi et al. |
| 6,949,522 | B2 | 9/2005 | Otto et al. |
| 7,094,770 | B2 | 8/2006 | Watanabe et al. |
| 7,105,493 | B2 | 9/2006 | Sommadossi et al. |
| 7,105,499 | B2 | 9/2006 | Carroll et al. |
| 7,125,855 | B2 | 10/2006 | Bhat et al. |
| 7,138,376 | B2 | 11/2006 | Gosselin et al. |
| 7,148,206 | B2 | 12/2006 | Sommadossi et al. |
| 7,157,441 | B2 | 1/2007 | Sommadossi et al. |
| 7,163,929 | B2 | 1/2007 | Sommadossi et al. |
| 7,169,766 | B2 | 1/2007 | Sommadossi et al. |
| 7,192,936 | B2 | 3/2007 | LaColla et al. |
| 7,202,224 | B2 | 4/2007 | Eldrup et al. |
| 7,211,570 | B2 | 5/2007 | Schinazi et al. |
| 7,268,119 | B2 | 9/2007 | Cook et al. |
| 7,285,658 | B2 | 10/2007 | Cook et al. |
| 7,307,065 | B2 | 12/2007 | Schinazi et al. |
| 7,323,449 | B2 | 1/2008 | Olsen et al. |
| 7,339,054 | B2 | 3/2008 | Xu et al. |
| 7,365,057 | B2 | 4/2008 | LaColla et al. |
| 7,384,924 | B2 | 6/2008 | LaColla et al. |

(Continued)

FOREIGN PATENT DOCUMENTS

| | | |
|---|---|---|
| CN | 103435672 A | 12/2013 |
| CN | 103980332 A | 8/2014 |

(Continued)

OTHER PUBLICATIONS

Jordan, Paul C., Sarah K. Stevens, and Jerome Deval. "Nucleosides for the treatment of respiratory RNA virus infections." Antiviral Chemistry and Chemotherapy 26 (2018): 2040206618764483.*

(Continued)

*Primary Examiner* — Patrick T Lewis
(74) *Attorney, Agent, or Firm* — Knowles Intellectual Property Strategies, LLC

(57) ABSTRACT

The present invention is the use of a small group of purine nucleotide phosphoramidate disclosed herein or a pharmaceutically acceptable salt thereof in an effective amount for the treatment or prevention of the novel 2019 coronavirus disease (COVID-19) in a host, for example a human, in need thereof.

17 Claims, 5 Drawing Sheets

(56) References Cited

U.S. PATENT DOCUMENTS

| | | |
|---|---|---|
| 7,388,002 B2 | 6/2008 | Babu et al. |
| 7,429,571 B2 | 9/2008 | Chand et al. |
| 7,429,572 B2 | 9/2008 | Clark |
| 7,456,155 B2 | 11/2008 | Sommadossi et al. |
| 7,495,006 B2 | 2/2009 | Liotta et al. |
| 7,514,410 B2 | 4/2009 | Babu et al. |
| 7,534,767 B2 | 5/2009 | Butora et al. |
| 7,547,704 B2 | 6/2009 | LaColla et al. |
| 7,560,434 B2 | 7/2009 | Babu et al. |
| 7,560,550 B2 | 7/2009 | Doring et al. |
| 7,582,618 B2 | 9/2009 | Sommadossi et al. |
| 7,601,820 B2 | 10/2009 | Wang et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,608,601 B2 | 10/2009 | Devos et al. |
| 7,625,875 B2 | 12/2009 | Gosselin et al. |
| 7,632,821 B2 | 12/2009 | Butora et al. |
| 7,635,689 B2 | 12/2009 | LaColla et al. |
| 7,638,502 B2 | 12/2009 | Schinazi et al. |
| 7,652,001 B2 | 1/2010 | Hostetler et al. |
| 7,662,798 B2 | 2/2010 | LaColla et al. |
| 7,662,938 B2 | 2/2010 | Schinazi et al. |
| 7,691,603 B2 | 4/2010 | DeFrees |
| 7,713,941 B2 | 5/2010 | Cook et al. |
| 7,718,790 B2 | 5/2010 | Stuyver et al. |
| 7,749,983 B2 | 7/2010 | Hostetler et al. |
| 7,772,208 B2 | 8/2010 | Schinazi et al. |
| 7,824,851 B2 | 11/2010 | Sommadossi et al. |
| 7,842,672 B2 | 11/2010 | Boojamra et al. |
| RE42,015 E | 12/2010 | Watanabe et al. |
| 7,879,815 B2 | 2/2011 | MacCoss et al. |
| 7,902,202 B2 | 3/2011 | Sommadossi et al. |
| 7,919,247 B2 | 4/2011 | Stuyver et al. |
| 7,932,240 B2 | 4/2011 | Dousson et al. |
| 7,951,789 B2 | 5/2011 | Sommadossi et al. |
| 7,964,580 B2 | 6/2011 | Sofia et al. |
| 7,973,013 B2 | 7/2011 | Cho et al. |
| 7,994,139 B2 | 8/2011 | Babu et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,071,567 B2 | 12/2011 | Devos et al. |
| 8,071,568 B2 | 12/2011 | Narjes et al. |
| 8,093,380 B2 | 1/2012 | Wang et al. |
| 8,114,994 B2 | 2/2012 | Liotta et al. |
| 8,114,997 B2 | 2/2012 | Otto et al. |
| 8,119,607 B2 | 2/2012 | Francom et al. |
| 8,133,870 B2 | 3/2012 | Babu et al. |
| 8,148,349 B2 | 4/2012 | Meppen et al. |
| 8,163,703 B2 | 4/2012 | Babu et al. |
| 8,168,583 B2 | 5/2012 | Schinazi et al. |
| 8,173,621 B2 | 5/2012 | Du et al. |
| 8,193,372 B2 | 6/2012 | Dousson et al. |
| 8,242,085 B2 | 8/2012 | Babu et al. |
| 8,299,038 B2 | 10/2012 | Sommadossi et al. |
| 8,318,682 B2 | 11/2012 | Butler et al. |
| 8,324,179 B2 | 12/2012 | Chen et al. |
| 8,334,270 B2 | 12/2012 | Sofia et al. |
| 8,343,937 B2 | 1/2013 | Sommadossi et al. |
| 8,362,068 B2 | 1/2013 | Dousson et al. |
| 8,399,428 B2 | 3/2013 | Wagner |
| 8,399,429 B2 | 3/2013 | Jonckers et al. |
| 8,415,308 B2 | 4/2013 | Cho et al. |
| 8,415,309 B2 | 4/2013 | Francom et al. |
| 8,415,321 B2 | 4/2013 | Schinazi et al. |
| 8,415,322 B2 | 4/2013 | Clark |
| 8,431,588 B2 | 4/2013 | Jonckers et al. |
| 8,440,813 B2 | 5/2013 | Babu et al. |
| 8,455,451 B2 | 6/2013 | Cho et al. |
| 8,470,834 B2 | 6/2013 | Kwong et al. |
| 8,481,510 B2 | 7/2013 | Jonckers et al. |
| 8,481,712 B2 | 7/2013 | Bhat et al. |
| 8,481,713 B2 | 7/2013 | Wang et al. |
| 8,492,539 B2 | 7/2013 | Chun et al. |
| 8,501,699 B2 | 8/2013 | Francom et al. |
| 8,507,460 B2 | 8/2013 | Surleraux et al. |
| 8,541,434 B2 | 9/2013 | Kwong et al. |
| 8,551,973 B2 | 10/2013 | Bao et al. |
| 8,552,021 B2 | 10/2013 | Jonckers et al. |
| 8,563,530 B2 | 10/2013 | Chang et al. |
| 8,575,119 B2 | 11/2013 | Wang et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,629,263 B2 | 1/2014 | Ross et al. |
| 8,633,309 B2 | 1/2014 | Ross et al. |
| 8,637,475 B1 | 1/2014 | Storer et al. |
| 8,642,756 B2 | 2/2014 | Ross et al. |
| 8,658,616 B2 | 2/2014 | McGuigan et al. |
| 8,673,926 B2 | 3/2014 | Chu |
| 8,674,085 B2 | 3/2014 | Sommadossi et al. |
| 8,680,071 B2 | 3/2014 | Surleraux et al. |
| 8,691,788 B2 | 4/2014 | Sommadossi et al. |
| 8,697,694 B2 | 4/2014 | Arasappan et al. |
| 8,715,638 B2 | 5/2014 | Kwong et al. |
| 8,716,262 B2 | 5/2014 | Sofia et al. |
| 8,716,263 B2 | 5/2014 | Chun et al. |
| 8,735,345 B2 | 5/2014 | Porter et al. |
| 8,735,372 B2 | 5/2014 | Du et al. |
| 8,735,569 B2 | 5/2014 | Ross et al. |
| 8,742,101 B2 | 6/2014 | Storer et al. |
| 8,759,318 B2 | 6/2014 | Chamberlain et al. |
| 8,759,372 B2 | 6/2014 | Roberts et al. |
| 8,759,510 B2 | 6/2014 | Du et al. |
| 8,765,710 B2 | 7/2014 | Sofia et al. |
| 8,772,474 B2 | 7/2014 | Beigelman et al. |
| 8,802,840 B2 | 8/2014 | Francom et al. |
| 8,815,829 B2 | 8/2014 | Schinazi et al. |
| 8,816,074 B2 | 8/2014 | Chu et al. |
| 8,841,275 B2 | 9/2014 | Du et al. |
| 8,846,638 B2 | 9/2014 | Or et al. |
| 8,846,896 B2 | 9/2014 | Serebryany et al. |
| 8,853,171 B2 | 10/2014 | Butler et al. |
| 8,859,595 B2 | 10/2014 | Coats et al. |
| 8,859,756 B2 | 10/2014 | Ross et al. |
| 8,871,737 B2 | 10/2014 | Smith et al. |
| 8,871,785 B2 | 10/2014 | Boojamra et al. |
| 8,877,731 B2 | 11/2014 | Beigelman et al. |
| 8,877,733 B2 | 11/2014 | Cho et al. |
| 8,889,159 B2 | 11/2014 | Cleary et al. |
| 8,889,701 B1 | 11/2014 | Ivachtchenko et al. |
| 8,895,531 B2 | 11/2014 | Shi |
| 8,895,723 B2 | 11/2014 | Serebryany et al. |
| 8,906,880 B2 | 12/2014 | Du et al. |
| 8,912,321 B2 | 12/2014 | Axt et al. |
| 8,921,384 B2 | 12/2014 | Chu |
| 8,927,513 B2 | 1/2015 | Manoharan et al. |
| 8,933,052 B2 | 1/2015 | Jonckers et al. |
| 8,946,244 B2 | 2/2015 | Chu et al. |
| 8,951,985 B2 | 2/2015 | Surleraux et al. |
| 8,957,045 B2 | 2/2015 | Sofia et al. |
| 8,957,046 B2 | 2/2015 | Du et al. |
| 8,980,865 B2 | 3/2015 | Wang et al. |
| 9,012,427 B2 | 4/2015 | Blatt et al. |
| 9,012,428 B2 | 4/2015 | Jonckers et al. |
| 9,045,520 B2 | 6/2015 | Chun et al. |
| 9,061,041 B2 | 6/2015 | Girijavallabhan et al. |
| 9,085,573 B2 | 7/2015 | Du et al. |
| 9,085,599 B2 | 7/2015 | Or et al. |
| 9,090,642 B2 | 7/2015 | Cho et al. |
| 9,109,001 B2 | 8/2015 | Parsy et al. |
| 9,139,604 B2 | 9/2015 | Boojamra et al. |
| 9,156,872 B2 | 10/2015 | Girijavallabhan et al. |
| 9,173,893 B2 | 11/2015 | Cho et al. |
| 9,187,515 B2 | 11/2015 | Mayes et al. |
| 9,192,621 B2 | 11/2015 | Mayes et al. |
| 9,211,300 B2 | 12/2015 | Mayes et al. |
| 9,243,025 B2 | 1/2016 | Surleraux et al. |
| 9,249,174 B2 | 2/2016 | Beigelman et al. |
| 9,339,541 B2 | 5/2016 | Dousson et al. |
| 9,351,989 B2 | 5/2016 | McGuigan et al. |
| 9,403,863 B2 | 8/2016 | Surleraux et al. |
| 9,408,863 B2 | 8/2016 | Verma et al. |

(56) References Cited

U.S. PATENT DOCUMENTS

| | | |
|---|---|---|
| 9,447,132 B2 | 9/2016 | Deshpande et al. |
| 9,598,457 B2 | 3/2017 | Smith et al. |
| 9,603,863 B2 | 3/2017 | Blatt et al. |
| 9,603,864 B2 | 3/2017 | Blatt et al. |
| 9,758,544 B2 | 9/2017 | Beigelman et al. |
| 9,815,864 B2 | 11/2017 | Beigelman et al. |
| 9,822,137 B2 | 11/2017 | Dehaen et al. |
| 9,828,410 B2 | 11/2017 | Sommadossi et al. |
| 9,890,188 B2 | 2/2018 | Wang et al. |
| 10,000,523 B2 | 6/2018 | Sommadossi et al. |
| 10,005,810 B2 | 6/2018 | McGuigan et al. |
| 10,005,811 B2 | 6/2018 | Sommadossi et al. |
| 10,202,386 B2 | 2/2019 | Biggadike et al. |
| 10,239,911 B2 | 3/2019 | Sommadossi et al. |
| 10,519,186 B2 | 12/2019 | Moussa et al. |
| 10,695,361 B2 | 6/2020 | Clarke et al. |
| 2002/0045599 A1 | 4/2002 | Arimilli et al. |
| 2002/0058635 A1 | 5/2002 | Averett |
| 2003/0087873 A1 | 5/2003 | Stuyver et al. |
| 2004/0063658 A1 | 4/2004 | Roberts et al. |
| 2004/0229839 A1 | 11/2004 | Babu et al. |
| 2004/0259934 A1 | 12/2004 | Olsen et al. |
| 2005/0038240 A1 | 2/2005 | Connolly et al. |
| 2005/0203044 A1 | 9/2005 | Zinnen |
| 2007/0265222 A1 | 11/2007 | MacCoss et al. |
| 2008/0207554 A1 | 8/2008 | Beigelman et al. |
| 2009/0156545 A1 | 6/2009 | Hostetler et al. |
| 2009/0176732 A1 | 7/2009 | Beigelman et al. |
| 2009/0181921 A1 | 7/2009 | Blatt et al. |
| 2009/0318380 A1 | 12/2009 | Sofia et al. |
| 2010/0137576 A1 | 6/2010 | Stec et al. |
| 2010/0240604 A1 | 9/2010 | Beigelman et al. |
| 2010/0249068 A1 | 9/2010 | Beigelman et al. |
| 2010/0279969 A1 | 11/2010 | Schinazi et al. |
| 2010/0331397 A1 | 12/2010 | Beigelman et al. |
| 2011/0091943 A1 | 4/2011 | Gallou et al. |
| 2011/0223659 A1 | 9/2011 | Scholl et al. |
| 2011/0257121 A1 | 10/2011 | Chang et al. |
| 2012/0070411 A1 | 3/2012 | Beigelman et al. |
| 2012/0135951 A1 | 5/2012 | Schinazi et al. |
| 2013/0064794 A1 | 3/2013 | Surleraux et al. |
| 2013/0225636 A1 | 8/2013 | Roberts et al. |
| 2013/0244966 A1 | 9/2013 | Milne et al. |
| 2013/0315868 A1 | 11/2013 | Mayes et al. |
| 2014/0038916 A1 | 2/2014 | Wang et al. |
| 2014/0066395 A1 | 3/2014 | Cho et al. |
| 2014/0112886 A1 | 4/2014 | Moussa et al. |
| 2014/0212382 A1 | 7/2014 | Schinazi et al. |
| 2014/0235566 A1 | 8/2014 | Amblard et al. |
| 2015/0011481 A1 | 1/2015 | Vilchez et al. |
| 2015/0011497 A1 | 1/2015 | Beigelman et al. |
| 2015/0057243 A1 | 2/2015 | Zhou et al. |
| 2015/0105341 A1 | 4/2015 | Beigelman et al. |
| 2015/0150897 A1 | 6/2015 | Denning et al. |
| 2015/0183818 A1 | 7/2015 | Tran et al. |
| 2016/0002281 A1 | 1/2016 | Mayes et al. |
| 2016/0220595 A1 | 8/2016 | Liotta et al. |
| 2016/0257706 A1 | 9/2016 | Sommadossi et al. |
| 2016/0271162 A1 | 9/2016 | Moussa et al. |
| 2017/0022242 A1 | 1/2017 | Herdewyn et al. |
| 2017/0029456 A1 | 2/2017 | Dousson et al. |
| 2017/0275322 A1 | 9/2017 | Oinho et al. |
| 2018/0009836 A1 | 1/2018 | Sommadossi et al. |
| 2019/0153017 A1 | 5/2019 | Sommadossi et al. |
| 2019/0201433 A1 | 7/2019 | Sommadossi et al. |
| 2019/0255085 A1 | 8/2019 | Clarke et al. |
| 2020/0087339 A1 | 3/2020 | Moussa et al. |

FOREIGN PATENT DOCUMENTS

| | | |
|---|---|---|
| CN | 105646629 A | 6/2016 |
| CN | 106188192 A | 12/2016 |
| EP | 547008 A1 | 6/1993 |
| EP | 398231 B1 | 7/1997 |
| WO | WO 1998/16184 | 4/1998 |
| WO | WO 1998/52949 A1 | 11/1998 |
| WO | WO 2001/009143 A1 | 2/2001 |
| WO | WO 2001/90121 A2 | 11/2001 |
| WO | WO 2001/92282 A2 | 12/2001 |
| WO | WO 2002/32920 A2 | 4/2002 |
| WO | WO 2003/033508 A1 | 4/2003 |
| WO | WO 2003/039523 A2 | 5/2003 |
| WO | WO 2003/062256 A1 | 7/2003 |
| WO | WO 2003/093290 A2 | 11/2003 |
| WO | WO 2004/002999 A2 | 1/2004 |
| WO | WO 2004/003000 A2 | 1/2004 |
| WO | WO 2004/014312 A2 | 2/2004 |
| WO | WO 2004/052906 A2 | 6/2004 |
| WO | WO 2004/074350 A2 | 9/2004 |
| WO | WO 2004/091499 A2 | 10/2004 |
| WO | WO 2004/106356 A1 | 12/2004 |
| WO | WO 2005/000864 A1 | 1/2005 |
| WO | WO 2005/020884 A2 | 3/2005 |
| WO | WO 2005/021568 A2 | 3/2005 |
| WO | WO 2005/084192 A2 | 9/2005 |
| WO | WO 2005/090370 A1 | 9/2005 |
| WO | WO 2006/012078 A2 | 2/2006 |
| WO | WO 2006/063149 A1 | 6/2006 |
| WO | WO 2006/063717 A2 | 7/2006 |
| WO | WO 2006/094347 A1 | 9/2006 |
| WO | WO 2006/102533 A2 | 9/2006 |
| WO | WO 2006/121820 A1 | 11/2006 |
| WO | WO 2006/130217 A2 | 12/2006 |
| WO | WO 2007/022073 A2 | 2/2007 |
| WO | WO 2007/112028 A2 | 10/2007 |
| WO | WO 2007/130783 A1 | 11/2007 |
| WO | WO 2008/012555 A2 | 1/2008 |
| WO | WO 2008/048128 A1 | 4/2008 |
| WO | WO 2008/062206 A2 | 5/2008 |
| WO | WO 2008/095040 A2 | 10/2008 |
| WO | WO 2009/001097 A2 | 12/2008 |
| WO | WO 2009/003042 A1 | 12/2008 |
| WO | WO 2009/067409 A1 | 5/2009 |
| WO | WO 2009/086192 A1 | 7/2009 |
| WO | WO 2009/086201 A1 | 7/2009 |
| WO | WO 2009/129120 A2 | 10/2009 |
| WO | WO 2010/081082 A2 | 7/2010 |
| WO | WO 2010/091386 A2 | 8/2010 |
| WO | WO 2010/108135 A1 | 9/2010 |
| WO | WO 2010/145778 | 12/2010 |
| WO | WO 2011/005595 A1 | 1/2011 |
| WO | WO 2011/005860 A2 | 1/2011 |
| WO | WO 2012/041965 A1 | 4/2012 |
| WO | WO 2012/048013 A2 | 4/2012 |
| WO | WO 2012/092484 A2 | 7/2012 |
| WO | WO 2012/125900 A1 | 9/2012 |
| WO | WO 2012/154321 A1 | 11/2012 |
| WO | WO 2012/158811 A2 | 11/2012 |
| WO | WO 2013/009737 A1 | 1/2013 |
| WO | WO 2013/019874 A1 | 2/2013 |
| WO | WO 2013/039855 A1 | 3/2013 |
| WO | WO 2013/039920 A1 | 3/2013 |
| WO | WO 2013/044030 A1 | 3/2013 |
| WO | WO 2013/059735 A1 | 4/2013 |
| WO | WO 2013/090420 A2 | 6/2013 |
| WO | WO 2013/096680 A1 | 6/2013 |
| WO | WO 2013/142125 A1 | 9/2013 |
| WO | WO 2013/142157 A1 | 9/2013 |
| WO | WO 2013/142159 A1 | 9/2013 |
| WO | WO 2013/151975 A1 | 10/2013 |
| WO | WO 2013/177219 A1 | 11/2013 |
| WO | WO 2013/187978 A1 | 12/2013 |
| WO | WO 2014/008236 A1 | 1/2014 |
| WO | WO 2014/047117 A1 | 3/2014 |
| WO | WO 2014/052638 A1 | 4/2014 |
| WO | WO 2014/063019 A1 | 4/2014 |
| WO | WO 2014/076490 A1 | 5/2014 |
| WO | WO 2014/082935 A1 | 6/2014 |
| WO | WO 2014/100498 A1 | 6/2014 |
| WO | WO 2014/100505 A1 | 6/2014 |
| WO | WO 2014/120981 A1 | 8/2014 |
| WO | WO 2014/124430 A1 | 8/2014 |
| WO | WO 2014/137930 A1 | 9/2014 |
| WO | WO 2014/169278 A1 | 10/2014 |

(56) References Cited

FOREIGN PATENT DOCUMENTS

| WO | WO 2014/169280 A2 | 10/2014 | | |
|---|---|---|---|---|
| WO | WO 2014/209979 A1 | 12/2014 | | |
| WO | WO 2015/038596 A1 | 3/2015 | | |
| WO | WO 2015/053662 A1 | 4/2015 | | |
| WO | WO 2015/081133 A2 | 6/2015 | | |
| WO | WO 2015/095305 A1 | 6/2015 | | |
| WO | WO 2015/158913 A1 | 10/2015 | | |
| WO | WO 2016/041877 A1 | 3/2016 | | |
| WO | WO 2016/100441 A1 | 6/2016 | | |
| WO | WO 2016/100569 A1 | 6/2016 | | |
| WO | WO 2016/144918 A1 | 9/2016 | | |
| WO | WO 2016/145142 A1 | 9/2016 | | |
| WO | WO 2018/013937 A1 | 1/2018 | | |
| WO | WO-2018048937 A1 * | 3/2018 | ........... | A61K 31/675 |
| WO | WO 2019/200005 A1 | 10/2019 | | |

OTHER PUBLICATIONS

Agostini, Maria L. et al. "Coronavirus Susceptibility to the Antiviral Remdesivir (GS-5734) Is Mediated by the Viral Polymerase and the Proofreading Exoribonuclease," American Society for Microbiology MBio., vol. 9 Issue 2, Mar. 6, 2018.

Ahmad, T. et al. "Cardiac dysfunction associated with a nucleotide polymerase inhibitor for treatment of hepatitis C" Hepatology, 62, 409, 2015.

Ahn et al. "Biochemical characterization of a recombinant SARS coronavirus nsp12 RNA-dependent RNA polymerase capable of copying viral RNA templates", Arch Virol., 157, 2095-2104, 2012.

Atea Pharmaceuticals Presentation, Jefferies Healthcare Conference, Jun. 8, 2022.

Berge, M.S. et al. "Pharmaceutical Salts" Journal of Pharmaceutical Sciences, 66, 1, 1977.

Berliba, et al. "Safety, Pharmacokinetics, and Antiviral Activity of AT-527, a Novel Purine Nucleotide Prodrug, in Hepatitis C Virus-Infected Subjects with or without Cirrhosis," Antimicrobial Agents and Chemotherapy, vol. 63, Issue 12, Dec. 2019.

Brown, Ariane J. et al. "Broad spectrum antiviral remdesivir inhibits human endemic and zoonotic deltacoronaviruses with a highly divergent RNA dependent RNA polymerase," Antiviral Research 169, Jun. 21, 2019.

Chang, W. et al. "Discovery of PSI-353661, a Novel Purine Nucleotide Prodrug for the Treatment of HCV Infection" ACS Med Chem Lett., 2, 130, 2011.

Clinical Trials—(NCT04252664) "A Trial of Remdesivir in Adults with Mild and Moderate COVID-19," Feb. 5, 2020.

Clinical Trial History of changes for study: NCT04396106 Safety and efficacy of AT-527 in subjects with moderate coronavirus disease (COVID-19), May 19, 2020.

Cretton-Scott, E. et al. "In vitro antiviral activity and pharmacology of idx184, a novel and potent inhibitor of HCV replication" (Abstract 588) J. Hepatol., 48, Supplement 2, S220, 2008.

Denison, Mark R. et al. "Coronaviruses an RNA proofreading machine regulates replication fidelity and diversity," RNA Biology 8:2, 270-279; Mar./Apr. 2011.

Freeman et al. 2-amino-9(3-azido-2,3-dideoxy-β-D-erythro-pentofuranosyl)-6-Substituted-9H-Purines: Synthesis and Anti-HIV Activity. Bioorganic and Medicinal Chemistry, 3(4): 447-448, 1995.

Gao et al. "Structure of the RNA-dependent RNA polymerase from COVID-19 virus", Science, 368(6492), 779-782, 2020.

Gilead Sciences Initiates Two Phase 3 Studies of Investigational Antiviral Remdesivir for the Treatment of COVID-19, U.S. FDA Grants Investigational New Drug Authorization to Study Remdesivir for the Treatment of COVID-19, Feb. 26, 2020.

Good, et al. "AT-527, a Double Prodrug of a Guanosine Nucleotide Analog, Is a Potent Inhibitor of SARS-CoV-2 In Vitro and a Promising Oral Antiviral for Treatment of COVID19" Antimicrobial Agents and Chemotherapy, vol. 65, Issue 4, Apr. 2021.

Good, et al. "Preclinical evaluation of AT-527, a novel guanosine nucleotide prodrug with potent, pan-genotypic activity against hepatitis C virus," PLOS One, https://doi.org/10.1371/journal.pone.0227104, Jan. 8, 2020.

Good, S. et al. "AT-337, AT-511, and its Salt Form, AT-527: Novel Potent and Selective Pan-genotypic Purine Nucleotide Prodrug Inhibitors of HCV Polymerase" presented at the AASLD 2017 Liver Meeting; Washington, D.C., Oct. 20-24, 2017.

Grein, J. et al. "Compassionate Use of Remdesivir for Patients with Severe Covid-19," The New England Journal of Medicine, Jun. 11, 2020.

Harris, Lynnette "Utah State University Antiviral Researchers at work on Coronavirus with NIH Support," Health & Wellness, Mar. 26, 2020.

Herman, B. et al. "Substrate mimicry: HIV-1 reverse transcriptase recognizes 6-modified-30-azido-20,30-dideoxyguanosine-50-triphosphates as adenosine analogs" Nucleic Acids Research 40, 381, 2012.

Hirayama, Noriaki, Handbook for Producing Organic Compound Crystals, pp. 17-23, 37-40, 45-51, and 57-65 (reference showing a well-known technique) and English partial translation, 2008.

Hoffman, M. et al., "SARS-CoV-2 Cell Entry Depends on ACE2 and TMPRSS2 and Is Blocked by a Clinically Proven Protease Inhibitor", Cell, 181(2), 271-280, 2020.

Holshue, Michelle L. et al. "First Case of 2019 Novel Coronavirus in the United States," The New England Journal of Medicine, 382; 929-936, Mar. 5, 2020.

Huang et al. "Impact of solid state properties on developability assessment of drug candidates" Advanced Drug Delivery Reviews, 56, 321, 2004.

Huang et al., "Clinical features of patients infected with 2019 novel coronavirus in Wuhan, China", Lancet, 395(10223), 497-506, 2020.

International Search Report and Written Opinion for PCT/US2021/19468, 10 pages, dated May 20, 2021.

Krausslich et al. eds. Antiviral Strategies, Springer-Verlag Berlin Heidelberg, pp. 1-24, 2009.

Lau et al., "Severe acute respiratory syndrome coronavirus-like virus in Chinese horseshoe bats", PNAS, 102(39), 14040-14045, 2005.

Luan et al., "Spike protein recognition of mammalian ACE2 predicts the host range and an optimized ACE2 for SARS-CoV-2 infection", Biochem. Biophys. Res. Commun., 526(1), 165-169, 2020.

Luo, Shouqi et al. "4793: Lack of Reproductive and Developmental Toxicity for AT-527 (Bemnifosbuvir), an Oral Purine Nucleotide Prodrug for COVID-19 Infection", Poster board P857 Society of Toxicology Annual Meeting, Mar. 27, 2022.

Luo, Shouqi et al. "4794: Characterization of the Toxicity Profile of AT-527 (Bemnifosbuvir), a Novel Guanosine Nucleotide Prodrug with Antiviral Activity for COVID-19 Infection", Poster board P858 Society of Toxicology Annual Meeting, Mar. 27, 2022.

McGuigan, C. et al. "Design, synthesis and evaluation of a novel double pro-drug: INX-08189. A new clinical candidate for hepatitis C virus" Bioorganic & Medicinal Chemistry Letters, 20, 4850, 2010.

McGuigan, C. et al. "Dual pro-drugs of 2'-C-methyl guanosine monophosphate as potent and selective inhibitors of hepatitis C virus" Bioorganic & Medicinal Chemistry Letters, 21, 6007, 2011.

Mehellou, Youcef, et al. The ProTide Prodrug Technology: From the Concept to the Clinic—Miniperspective; Journal of Medicinal Chemistry, J. Med. Chem, 61, 2211-2226, 2018.

Murakami, E. et al. "Adenosine Deaminase-like Protein 1 (ADAL1): Characterization and Substrate Specificity in the Hydrolysis of N6- or 06-Substituted Purine or 2-Aminopurine Nucleoside Monophosphates" J Med Chem, 54, 5902, 2011.

Nguyen, Lien et al. International Journal of Biomedical Science: Chiral Drugs: An Overview; 20; 85-100, Jun. 2, 2006.

NIAID's Multi-Pronged Response to the COVID-2019 Outbreak, Allergy and Infectious Diseases, Feb. 19, 2020.

Owen, Dafydd R., et al. "An oral SARS-CoV-2 Mpro inhibitor clinical candidate for the treatment of COVID-19," Science 374, 1586-1593, Dec. 24, 2021.

(56) References Cited

OTHER PUBLICATIONS

Poordad et al. "Daclatasvir with Sofosbuvir and Ribavirin for Hepatitis C Virus Infection with Advanced Cirrhosis or Post-Liver Transplantation Recurrence" Hepatology, 63, 1493, 2016.

Pradere, U. et al. "Synthesis of 5'-Methylene-Phosphonate Furanonucleoside Prodrugs: Application to D-2'-Deoxy-2'-α-fluoro-2'-β-C-methyl Nucleosides" Organic Letters, 14, 4426, 2012.

Press Release, "Atea Pharmaceuticals Provides Update and Topline Results for Phase 2 MOONSONG Trial Evaluating AT-527 in the Outpatient Setting", Oct. 19, 2021.

Press Release, "Atea Pharmaceuticals Introduces New Strategic Clinical Development Program for AT-527 in COVID-19", Dec. 14, 2021.

Press Release, "Atea Pharmaceuticals Reports Nonclinical Bemnifosbuvir (AT-527) Toxicology Data at Society of Toxicology 61st Annual Meeting"; Mar. 28, 2022.

Press Release, "Atea to Advance Global Phase 3 Registrational Study of Bemnifosbuvir in High-Rish Non-Hospitalized Patients with COVID-19", Sep. 13, 2022.

Pruijssers, Andrea J. et al. Nucleoside analogues for the treatment of coronavirus infections, Current Opinion in Virology, 35:57-62, Apr. 2019.

Reddy, P. et al. "2'-Deoxy-2'-α-fluoro-2'-β-C-methyl 3',5'-cyclic phosphate nucleotide prodrug analogs as inhibitors of HCV NS5B polymerase: Discovery of PSI-352938" Bioorganic & Medicinal Chemistry Letters, 20, 7376, 2010.

Rest et al. "SARS associated coronavirus has a recombinant polymerase and coronaviruses have a history of host-shifting", Infect Genet Evol., 3(3), 219-225, 2003.

Rockman, Glenn "To accelerate innovation, the CDC should ease limits on which labs can handle the coronavirus," STAT News, Apr. 14, 2020.

Schoeman and Fielding, "Coronavirus envelope protein: current knowledge", Virology, 16(69), 1-22, 2019.

Serajuddin, A.T.M "Salt formation to improve drug solubility" Advanced Drug Delivery Reviews, 59, 603, 2007.

Shannon, Ashleigh, et al. "Remdesivir and SARS-COV-2: Structural requirements at both nsp12 RdRp and nsp14 Exonuclease active-sites," Antiviral Research, 178, Jun. 2020.

Shannon, Ashleigh et al. "A dual mechanism of action of AT-527 against SARS-CoV-2 polymerase" Nature Communications, 13, 621, Feb. 2, 2022.

Sheahan, Timothy P. et al. "Broad-spectrum antiviral GS-5734 inhibits both epidemic and zoonotic coronaviruses," Sci Transl. Med., 9(396), Jun. 28, 2017.

Smith, Everett C. et al. "Coronaviruses Lacking Exoribonuclease Activity Are Susceptible to Lethal Mutagenesis: Evidence for Proofreading and Potential Therapeutics," PLOS Pathogens, vol. 9 issues 8, Aug. 13, 2013.

Sofia, M.J. "Nucleotide Prodrugs for HCV Therapy," Antiviral Chemistry & Chemotherapy, 22, 23, 2011.

Stahl et al. "Handbook of Pharmaceutical Salts Properties, Selection, and Use", International Union of Pure and Applied Chemistry (IUPAC), (Chapters 6 and 7), 2002.

Subissi et al. "One severe acute respiratory syndrome coronavirus protein complex integrates processive RNA polymerase and exonuclease activities", Proc. Natl. Acad. Sci., 111(37), E3900-E3909, 2014.

Tao, S. et al. Comparison of Three 2'-C-Methyl Guanosine Prodrugs for Hepatitis C including a Novel $^2$-D-2'-C-Me-2,6-Diaminopurine Ribonucleoside Phosphoramidate (RS-1389): Interspecies Hepatocyte and Human Cardiomyocyte Metabolism Profiles. The Liver Meeting, Boston, MA, USA, Nov. 6-11, 2014.

Wang, Manli et al. Remdesivir and chloroquine effectively inhibit the recently emerged novel coronavirus (2019-nCoV) in vitro, Cell Research, 30:269-271, Feb. 4, 2020.

Wu et al. "Ribavirin, viramidine and adenosine-deaminase-catalysed drug activation: implication for nucleoside prodrug design", Journal of Antimicrobial Chemotherapy, vol. 52:543-546, 2003.

Xu, Xiang, et al. "Molecular model of SARS coronavirus polymerase: implications for biochemical functions and drug design," Nucleic Acids Research, vol. 31, No. 24, 7117-7130, Dec. 15, 2003.

Yang et al. "Targeting the Endocytic Pathway and Autophagy Process as a Novel Therapeutic Strategy in COVID-19", Int. J. Biol. Sci., 16(10), 1724-1731, 2020.

Yoon et al. Design, Synthesis, and Anti-RNA Virus of 6'-Fluorinated-Aristeromycin Analogues Journal of Medicine Chemistry, vol. 62, p. 6346-6362, Jun. 7, 2019.

Zhang et al. "Synthesis and evaluation of 30-azido-20,30-dideoxypurine nucleosides as inhibitors of human immunodeficiency virus" Bioorganic and Medicinal Chemistry Letters, 20, 60, 2010.

Zhou et al. "A pneumonia outbreak associated with a new coronavirus of probable bat origin", Nature, 579, 270, 2020.

Zhou, L. et al. "β-D-2'-C-Methyl-2,6-diaminopurine Ribonucleoside Phosphoramidates are Potent and Selective Inhibitors of Hepatitis C Virus (HCV) and Are Bioconverted Intracellularly to Bioactive 2,6-Diaminopurine and Guanosine 5'-Triphosphate Forms" J Med Chem, 58, 3445, 2015.

Zhou, X. et al. "A Phase 1a Study of AT-527, a Novel Pan-Genotypic Purine Nucleotide Prodrug Inhibitor of Hepatitis C Virus (HCV)" presented at The Liver Meeting, Washington, D.C., Oct. 23, 2017.

Zhou, X. et al. "AT-527, a pan-genotypic purine nucleotide prodrug, exhibits potent antiviral activity in subjects with chronic hepatitis C" presented at The International Liver Congress, Paris, France, Apr. 13, 2018.

US, U.S. Pat. No. 9,828,410, B2, U.S. Appl. No. 15/063,461, Sommadossi et al., Nov. 28, 2017.

US, U.S. Pat. No. 10,000,523, B2, U.S. Appl. No. 15/782,628, Sommadossi et al., Jun. 19, 2018.

US, U.S. Pat. No. 10,005,811, B2, U.S. Appl. No. 15/782,638, Sommadossi et al., Jun. 26, 2018.

US, U.S. Pat. No. 10,202,412, B2, U.S. Appl. No. 15/645,701, Sommadossi et al., Feb. 12, 2019.

US, U.S. Pat. No. 10,239,911, B2, U.S. Appl. No. 16/001,549, Sommadossi et al., Mar. 26, 2019.

US, U.S. Pat. No. 10,519,186, B2, U.S. Appl. No. 15/885,630, Moussa et al., Dec. 31, 2019.

US, U.S. Pat. No. 10,815,266, B2, U.S. Appl. No. 16/278,621, Sommadossi et al., Oct. 27, 2020.

US, U.S. Pat. No. 10,870,672, B2, U.S. Appl. No. 16/900,397, Sommadossi et al., Dec. 22, 2020.

US, U.S. Pat. No. 10,870,673, B2, U.S. Appl. No. 16/918,898, Sommadossi et al., Dec. 22, 2020.

US, U.S. Pat. No. 10,874,687, B2, U.S. Appl. No. 17/017,443, Sommadossi et al., Dec. 29, 2020.

US, U.S. Pat. No. 10,875,885, B2, U.S. Appl. No. 16/918,914, Sommadossi et al., Dec. 29, 2020.

US, U.S. Pat. No. 10,894,804, U.S. Appl. No. 16/918,918, Moussa et al., Jan. 19, 2021.

US, U.S. Pat. No. 10,906,928, B2, U.S. Appl. No. 16/687,136, Moussa et al., Feb. 2, 2021.

US, U.S. Pat. No. 10,946,033, B2, U.S. Appl. No. 16/293,423, Sommadossi et al., Mar. 16, 2021.

US, U.S. Pat. No. 11,690,860, B2, U.S. Appl. No. 17/065,149, Sommadossi et al., filed Jul. 4, 2023.

US, U.S. Pat. No. 11,707,480, B2, U.S. Appl. No. 17/094,541, Sommadossi et al., Jul. 25, 2023.

US, U.S. Pat. No. 11,738,038, B2, U.S. Appl. No. 17/306,674, Sommadossi et al., Aug. 29, 2023.

US, U.S. Pat. No. 11,813,278, B2, U.S. Appl. No. 17/184,445, Sommadossi et al., Nov. 14, 2023.

US, U.S. Pat. No. 11,975,016, B2, U.S. Appl. No. 17/482,224, Sommadossi et al., May 7, 2024.

US, U.S. Pat. No. 12,006,340, B2, U.S. Appl. No. 18/100,448, Moussa et al., Jun. 11, 2024.

US, 2020/0179415, A1, U.S. Appl. No. 16/703,599, Sommadossi et al., Jun. 11, 2020.

US, 2020/0222442, A1, U.S. Appl. No. 16/821,850, Sommadossi et al., Jul. 16, 2020.

(56) References Cited

OTHER PUBLICATIONS

US, 2021/0009628, A1, U.S. Appl. No. 17/028,724, Sommadossi et al., Jan. 14, 2021.
US, 2021/0087217, A1, U.S. Appl. No. 17/118,314, Moussa et al., Mar. 25, 2021.
US, 2021/0277045, A1, U.S. Appl. No. 17/306,659, Moussa et al., Sep. 9, 2021.
US, 2022/0267366, A1, U.S. Appl. No. 17/306,643, Sommadossi et al., Aug. 25, 2022.
US, 2023/0049294, A1, U.S. Appl. No. 17/971,318, Moussa et al., Feb. 16, 2023.
US, 2023/0331751, A1, U.S. Appl. No. 18/111,316, Moussa et al., Oct. 19, 2023.
US, 2023/0364121, A1, U.S. Appl. No. 18/132,300, Sommadossi et al., Nov. 16, 2023.
US, 2023/0365611, A1, U.S. Appl. No. 18/226,064, Moussa et al., Nov. 16, 2023.
US, 2024/0002426, A1, U.S. Appl. No. 18/100,452, Sommadossi et al., Jan. 4, 2024.
US, 2024/0148770, A1, U.S. Appl. No. 18/540,608, Sommadossi et al., May 9, 2024.
U.S. Appl. No. 18/206,921, Sommadossi et al., filed Jun. 7, 2023,
U.S. Appl. No. 18/368,959, Sommadossi et al., filed Sep. 15, 2023.
U.S. Appl. No. 18/592,037, Sommadossi et al., filed Feb. 29, 2024
U.S. Appl. No. 18/739,149, Moussa et al., filed Jun. 10, 2024, \* cited by examiner

HIGHLY ACTIVE COMPOUNDS AGAINST COVID-19

CROSS-REFERENCE TO RELATED APPLICATIONS

This application is a continuation of U.S. Ser. No. 17/094,541, filed Nov. 10, 2020; which is a continuation U.S. Ser. No. 17/017,443, filed Sep. 10, 2020, which claims the benefit of U.S. Provisional Application No. 62/982,670, filed Feb. 27, 2020; U.S. Provisional Application No. 62/994,206, filed Mar. 24, 2020; U.S. Provisional Application No. 63/032,247, filed May 29, 2020; U.S. Provisional Application No. 63/039,352, filed Jun. 15, 2020; U.S. Provisional Application No. 63/040,985, filed Jun. 18, 2020; U.S. Provisional Application No. 63/054,680, filed Jul. 21, 2020; and U.S. Provisional 63/073,328 file Sep. 1, 2020. The entirety of each of these applications is incorporated by reference in their entireties for all purposes.

FIELD OF THE INVENTION

The present invention is directed to the use of selected purine nucleotides and their pharmaceutically acceptable salts which have advantageous activity and dosage convenience for the treatment or prevention of COVID-19 caused by the SARS-CoV-2 virus in a host, typically a human, in need thereof.

BACKGROUND OF THE INVENTION

In December 2019, a number of patients in Wuhan, China were diagnosed with pneumonia. These patients exhibited symptoms similar to the SARS (severe acute respiratory syndrome) outbreak in 2002-2003. In January 2020, the infectious cause was identified as a novel coronavirus that was named severe acute respiratory syndrome coronavirus-2 (SARS-CoV-2), and the resulting disease called coronavirus disease 2019 (COVID-19). This potentially severe and sometimes lethal disease quickly spread throughout the world. On Mar. 11, 2020, the World Health Organization declared COVID-19 a global pandemic.

The majority of patients infected with SARS-CoV-2 exhibit mild, cold-like symptoms, including fever, cough, fatigue, shortness of breath, muscle aches, and loss of taste and/or smell. These symptoms usually resolve with minimal medical care in a few weeks. However, occasionally, symptoms persist for months. The virus may cause long-term damage to the lungs, heart, and brain. Furthermore, in some patients, especially older adults, immunocompromised individuals, or those with underlying conditions, the virus can cause severe symptoms that result in hospitalization, ventilation, and/or death.

SARS-CoV-2 is a coronavirus (CoV), which is in the order Nidovirales, family Coronaviridae, subfamily Coronavirinae. These viruses are enveloped viruses with a single-strand, positive-sense RNA genome. SARS-CoV-2 is approximately 30 kilobases in size, which is among the largest known RNA genomes. Related coronaviruses include severe acute respiratory syndrome coronavirus (SARS-CoV) and Middle East respiratory syndrome coronavirus (MERS-CoV). However, SARS-CoV-2 only shares 79.5% of its genome with SARS-CoV, and is therefore considered a new human-infecting betacoronavirus (Zhou et al. Nature 2020, 579, 270). Compared to SARS-CoV and MERS-CoV, SARS-CoV-2 exhibits a faster human-to-human transmission rate (Huang et al., Lancet 2000, 395, 497), making it particularly challenging to contain and dangerous.

CoVs often originate as enzootic infections that cross the animal-human species barrier and progress to establish zoonotic diseases in humans (Lau et al., PNAS 2005, 102, 14040-5; Rest et al., Infect Genet Evol. 2003, 3, 219-25). Cross-species barrier jumps allowed CoVs such as the SARS CoV and the Middle Eastern respiratory syndrome CoV (MERS) to manifest as virulent human viruses (Schoeman and Fielding, Virology 2019, 16, 69). Similarly, genome sequencing has revealed that SARS-CoV-2 is 96% identical at the whole-genome level to a bat coronavirus (Zhou et al. Nature 2020, 579, 270) and therefore most likely originated in bats.

SARS-CoV-2 enters human cells by binding to angiotensin converting enzyme 2 (hACE2) receptors. Spike glycoproteins on the surface of the virus envelope bind to the ACE2 receptor and then the human transmembrane protease serine 2 cleaves and activates the spike protein, which allows SARS-CoV-2 to enter the cell through endocytosis or direct fusion with the host membrane (Luan et al. Biochem. Biophys. Res. Commun. 2020: 527, 165; Hoffman, M. et al. Cell, 2020, 181, 271; Yang et al. Int. J. Biol. Sci. 2020, 16, 1724).

Once inside the cell, SARS-CoV-2 transcription and replication is mediated by a multi-subunit polymerase complex. The catalytic subunit of the complex is the RNA-dependent RNA polymerase (RdRp) known as nsp12. While the isolated nsp12 subunit is capable of conducting the polymerase reaction by itself, the presence of cofactors nsp7 and nsp8 significantly increases the efficiency of the polymerase reaction (Ahn et al. Arch Virol. 2012, 157, 2095; Subissi et al. Proc. Natl. Acad. Sci., 2014, 111, E3900).

In April 2020, a crystal structure of the SARS-CoV-2 nsp-12, in complex with nsp-7 and nsp-8, was resolved (Gao et al. Science 2020, 368:779-782). The structure of nsp12 contains a polymerase C-terminal RdRp domain that is connected to an N-terminal extension domain referred to as the nidovirus RdRp-associated nucleotidyltransferase (NiRAN) domain. This NiRAN domain, which is conserved in all nidoviruses that are able to conduct nucleotidylation activity, is characterized by an α and β fold composed of eight α helices and a five stranded β-sheet (Gao et al. Science 2020, 368:779-782). The C-terminal domain has been characterized as a "cupped right hand" domain with finger, thumb, and palm subdomains.

The history of creating therapeutics for human coronavirus diseases illustrates the complexity and challenges of the problem. There are still no commercial vaccines or drugs for MERS-CoV and SARS-CoV, despite the fact that the viruses were discovered in 2012 and 2003, respectively.

The lack of approved treatment, in combination with its high mortality rate and its ease and speed of transmission, highlights the need for the development of an effective COVID-19 antiviral medication.

It is therefore an object of the present invention to provide compounds, compositions, and methods for the treatment and prevention of COVID-19 disease.

SUMMARY OF THE INVENTION

The present invention provides a treatment for a host in need thereof infected with the SARS-CoV-2 virus comprising administering an effective amount of a selected purine nucleotide compound as further described herein, and in particular, Compound 1 or 2 as described below, for the advantageous treatment, prevention, or prophylaxis of COVID-19 disease. These purine nucleotides exhibit focused activity against the virus.

Further, and importantly, these compounds can be administered to hosts, such as humans, in need thereof, using a simple solid oral dosage form that can be conveniently taken at home or generally outside of a medical facility, and without requiring a parenteral administration or hospitalization. If desired or appropriate, the active compounds described herein can alternatively be administered parenterally or orally in a medical facility. The therapy can be used to treat mild, moderate or severe disease.

In one embodiment of the present invention, a compound of Formula I

Formula I

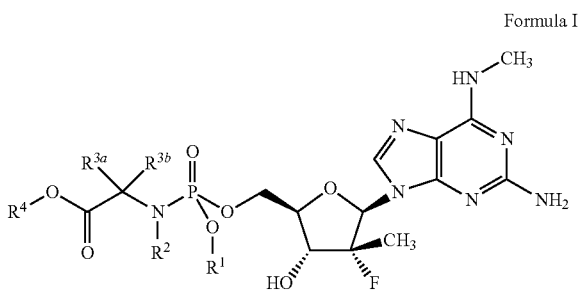

or a pharmaceutically acceptable salt thereof, optionally in a pharmaceutically acceptable carrier, is administered to a host, typically a human, in need thereof infected with SARS-CoV-2 or at risk of infection or reinfection with the SARS-CoV-2 virus, i.e., as a prophylactic (and wherein the term prophylactic means total prevention or minimization of infection relative to disease without such prophylactic treatment), wherein:

- $R^1$ is hydrogen, $C_{1-6}$alkyl (including methyl, ethyl, propyl, and isopropyl), $C_{3-7}$cycloalkyl, or aryl (including phenyl and napthyl) and in an alternative embodiment, $R^1$ is aryl-$C_{1-4}$alkyl (including benzyl);
- $R^2$ is hydrogen or $C_{1-6}$alkyl (including methyl, ethyl, propyl, and isopropyl);
- $R^{3a}$ and $R^{3b}$ are independently selected from hydrogen, $C_{1-6}$alkyl (including methyl, ethyl, propyl, and isopropyl), and $C_{3-7}$cycloalkyl; and
- $R^4$ is hydrogen, $C_{1-6}$alkyl (including methyl, ethyl, propyl, and isopropyl), $C_{1-6}$haloalkyl, or $C_{3-7}$cycloalkyl and in an alternative embodiment, $R^4$ is aryl-$C_{1-4}$alkyl (including benzyl).

Non-limiting examples of $C_1$-$C_6$alkyl include methyl, ethyl, propyl, isopropyl, butyl, t-butyl, sec-butyl, isobutyl, —$CH_2C(CH_3)_3$, —$CH(CH_2CH_3)_2$, and —$CH_2CH(CH_2CH_3)_2$. Non-limiting examples of $C_3$-$C_6$cycloalkyl include cyclopropyl, $CH_2$-cyclopropyl, cyclobutyl, and $CH_2$-cyclobutyl.

A non-limiting example of a compound of Formula I is Compound 1 or a pharmaceutically acceptable salt thereof. In one embodiment, Compound 1 or a pharmaceutically acceptable salt thereof, optionally in a pharmaceutically acceptable carrier, is administered to a host in need thereof, such as a human, infected with SARS-CoV-2, or to a host at risk of infection with SARS-CoV-2, i.e., as a prophylactic.

Compound 1

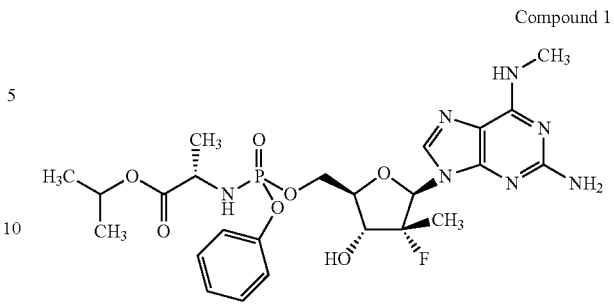

Compound 1 is depicted above without regard to stereochemistry at the phosphorus atom, which is chiral. Compound 1 can be used either without regard to stereochemistry at the phosphorus, or a phosphoro-racemic form, or with any desired ratio of phosphorus R- and S-enantiomers of the compound, including enantiomerically enriched (i.e., up to at least 90%, 95%, 98%, 99%, or even 100% free of the opposite enantiomer, which are in fact diastereomers because there are multiple chiral carbons in the molecule). Compound 1A is the S-enantiomer and Compound 1B is the R-enantiomer.

Compound 1A

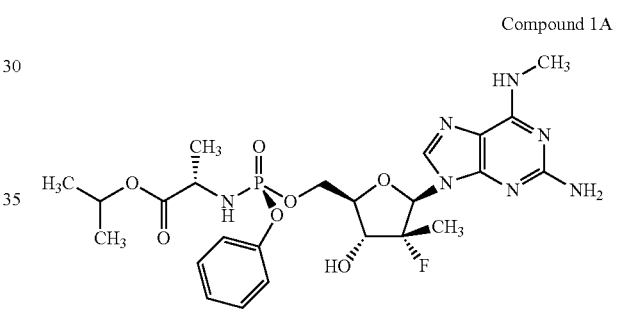

Compound 1B

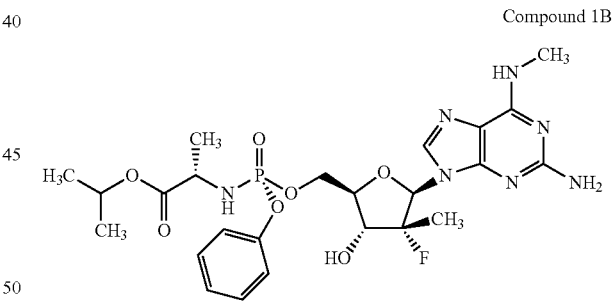

Compound 1A and Compound 1B are potent inhibitors against COVID-19 caused by the SARS-CoV-2 virus. As described in Example 5 and Example 6, Compound 1A exhibits an $EC_{90}$ value of 0.54 μM against SARS-Cov-2 in HAE cells (human airway epithelial cells). The assay using HAE cells is an in vitro model of the lung and is a representative system for SARS-CoV-2 replication. It has also been surprisingly discovered that the active triphosphate metabolite of Compound 1A is robustly formed when exposed to normal primary bronchial and nasal epithelial cells. As described in Example 7, when Compound 1A was incubated in human nasal and bronchial epithelial cells, the half-life of the active triphosphate species is greater than 1.5 days in both bronchial and nasal epithelial cells. This could not have been predicted in advance and is especially important in treating patients with early stages of the infection when the virus is heavily concentrated in the nasal and bronchial cells.

The data herein presented shows that the compound concentrates in the lung over the liver, and previously reported data confirms that the compounds also preferentially concentrate in the liver over the heart (see for example, Example 19 of PCT Application PCT/US2018/016301). Taken together, this data confirms that the compound concentrates in the target organ, the lung, over the liver or heart, reducing toxicity.

In one embodiment, Compound 1A or Compound 1B or a pharmaceutically acceptable salt thereof, optionally in a pharmaceutically acceptable carrier, is administered to a host, for example, a human, in need thereof infected with SARS-CoV-2, or a host at risk of infection, i.e., as a prophylactic. In one embodiment, the pharmaceutically acceptable salt is a hemi-sulfate salt, shown below as Compound 2, Compound 2A, and Compound 2B:

Compound 2

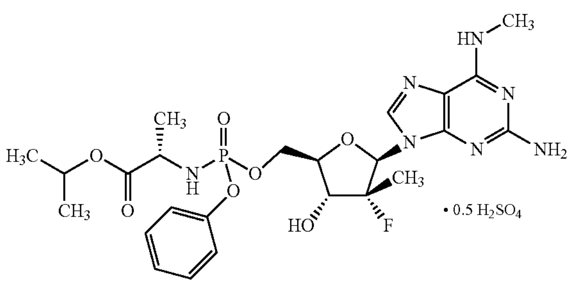

Compound 2A

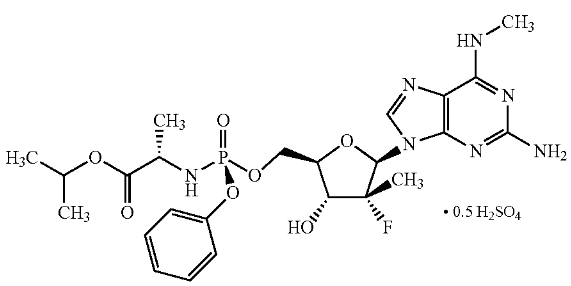

Compound 2B

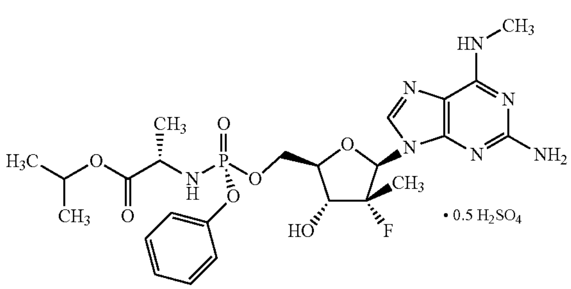

As described in Example 8, Compound 2A was administered to non-human primates and the intracellular concentration of the active triphosphate species was measured in lung, kidney, and liver cells. Surprisingly, the active triphosphate metabolite concentrated in the lung over the liver (Table 8) and the half-life of the active metabolite in the lung is 9.4 hours (FIG. 7). This is important because COVID-19 typically presents as a respiratory illness. In fact, the active triphosphate species concentration is 1.6 times higher in the lung than the liver after twice a day oral administration of 30 mg/kg of Compound 2A.

Furthermore, the compounds of the present invention may inhibit SARS-CoV-2 infection via a unique mechanism of action that accounts for high selectivity for SARS-CoV-2. CoV viral replication is achieved at the RNA-dependent RNA polymerase (RdRp) nsp12 subunit, which is activated by co-factors nsp7 and nsp8. As discussed in Example 6, there is a 30-fold difference in Compound 1A activity against SARS-CoV-2 and MERS-CoV, even though MERS-CoV and other CoVs, such as SARS-CoV-1 and SARS-CoV-2, do not exhibit significant structural differences at the RdRp active site. This suggests that polymerase inhibition is not the basis for differential activity of the nucleotides.

COVID-19 is an acute viral infection for which antiviral therapeutics may be effective within the first stage of the infection when viral load is at its maximum and there is rapid viral replication initially in nasal, throat and pulmonary cells. The availability of a potent, safe, oral antiviral administered to individuals infected with SARS-CoV-2 in the early stages of the disease has the potential to avert clinical illness, minimize long term damage, and mitigate the COVID-19 pandemic. As described above, it has been shown that selected compounds of the present invention are able to concentrate in the lungs over the liver. This is therapeutically beneficial when treating patients in the first stages of infection with the SARS-CoV-2 pathogen when it is desirable to prevent or lessen late stage viral damage. High concentrations in the lung over the heart and liver is also therapeutically beneficial for treating patients in later stages of the infection.

The present invention also includes the use of a compound of Formula II to treat or prevent COVID-19 disease in a host in need thereof as described herein:

Formula II 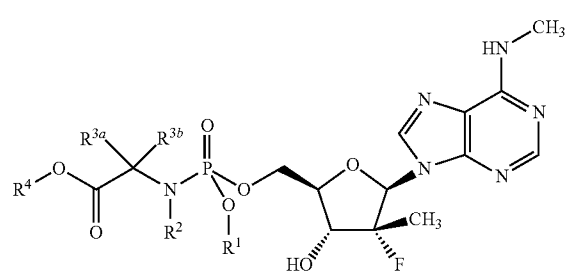 or a pharmaceutically acceptable salt thereof, wherein:

$R^1$ is hydrogen, $C_{1-6}$alkyl (including methyl, ethyl, propyl, and isopropyl), $C_{3-7}$cycloalkyl, or aryl (including phenyl and napthyl) and in an alternative embodiment, $R^1$ is aryl-$C_{1-4}$alkyl (including benzyl);

$R^2$ is hydrogen or $C_{1-6}$alkyl (including methyl, ethyl, propyl, and isopropyl);

$R^{3a}$ and $R^{3b}$ are independently selected from hydrogen, $C_{1-6}$alkyl (including methyl, ethyl, propyl, and isopropyl), and $C_{3-7}$cycloalkyl; and $R^4$ is hydrogen, $C_{1-6}$alkyl (including methyl, ethyl, propyl, and isopropyl), $C_{1-6}$haloalkyl, or $C_{3-7}$cycloalkyl and in an alternative embodiment, $R^4$ is aryl-$C_{1-4}$alkyl (including benzyl).

In one embodiment, a compound of Formula II or a pharmaceutically acceptable salt thereof, optionally in a pharmaceutically acceptable carrier, is administered to a host in need thereof infected with SARS-CoV-2, or to a host at risk of infection with SARS-CoV-2, i.e., as a prophylactic.

A non-limiting example of a compound of Formula II is Compound 3 or a pharmaceutically acceptable salt thereof.

Compound 3A

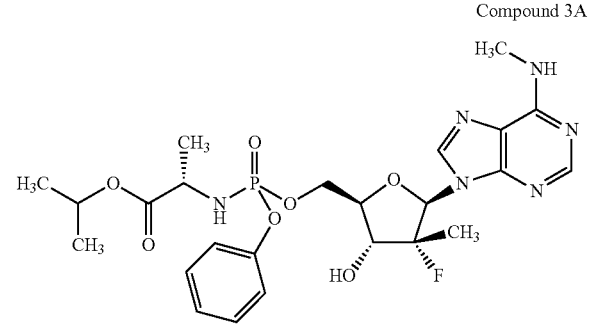 [SMILES: CNc1ncnc2c1ncn2[C@@H]1O[C@H](COP(=O)(N[C@@H](C)C(=O)OC(C)C)Oc2ccccc2)[C@@H](O)[C@@]1(C)F]

In one embodiment, Compound 3 or a pharmaceutically acceptable salt thereof, optionally in a pharmaceutically acceptable carrier, is administered to a host in need thereof infected with SARS-CoV-2, or to a host at risk of infection, i.e., as a prophylactic. Compound 3 can be used in a phosphoro-racemic form, or with any desired ratio of phosphorus R- and S-enantiomers of the compound, including enantiomerically enriched material up to pure enantiomers. Compound 3A is the S-enantiomer and Compound 3B is the R-enantiomer.

Compound 3A

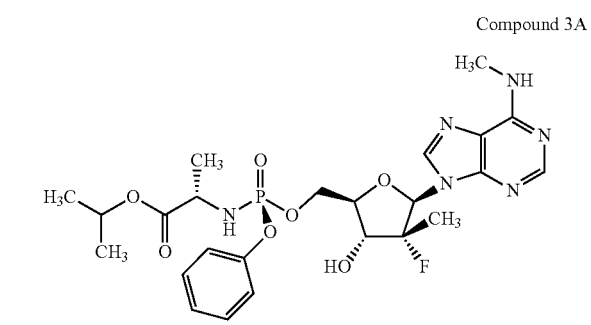

Compound 3B

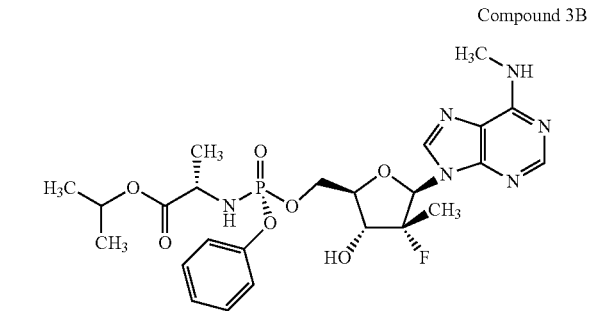

An additional non-limiting example of Formula II includes Compound 4. Alternative configurations of Compound 4 include Compound 4A and Compound 4B. In one embodiment, Compound 4, optionally in a pharmaceutically acceptable carrier, is administered to a host in need thereof infected with COVID-19 or to a host at risk of infection, i.e., as a prophylactic.

Compound 4

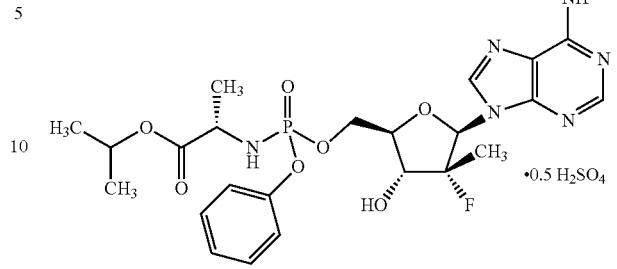

Compound 4A

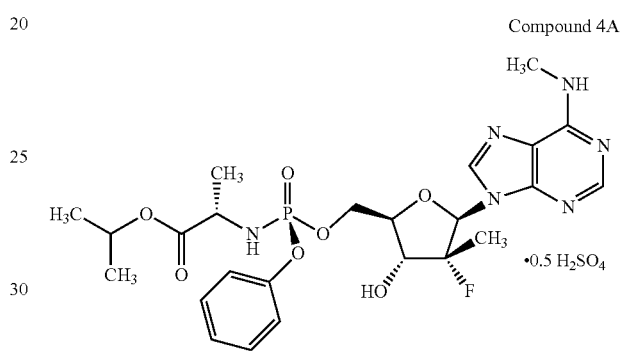

Compound 4B

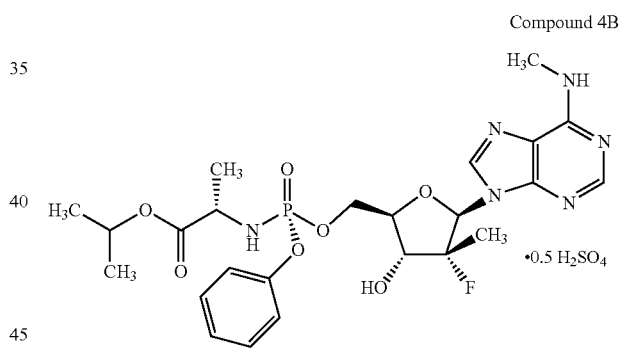

The present invention also includes the use of a compound of Formula III, Formula IV, or Formula V wherein $R^5$ is a monophosphate, a diphosphate, a triphosphate, or $R^6$ wherein $R^6$ is a stabilized phosphate prodrug that metabolizes in vivo to a monophosphate, diphosphate, or triphosphate to treat or prevent COVID-19 disease in a host in need thereof as described herein:

Formula III

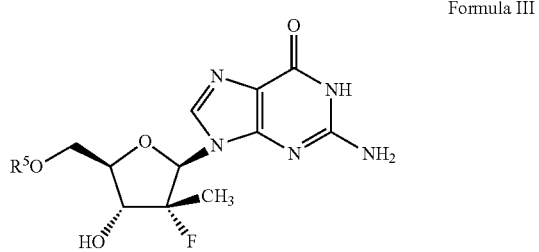

Formula IV
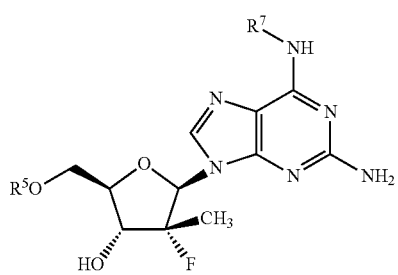
Formula V
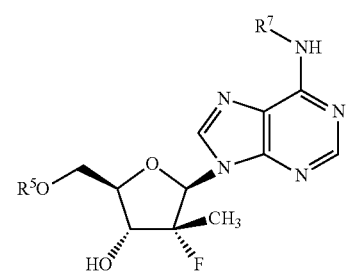
wherein
R⁵ is selected from
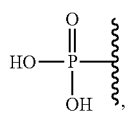
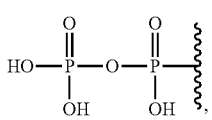
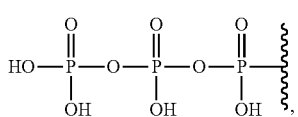
and R⁶;
R⁶ is a stabilized phosphate prodrug that metabolizes in vivo to a monophosphate, diphosphate, or triphosphate; and
R⁷ is selected from hydrogen and methyl.
Non-limiting examples of compounds of Formula III, Formula IV, or Formula V include:
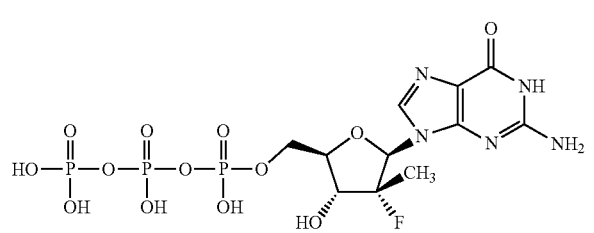
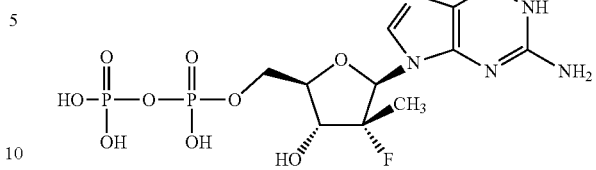
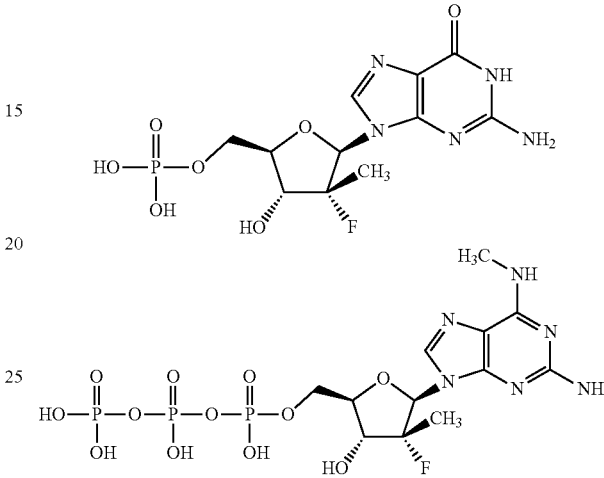
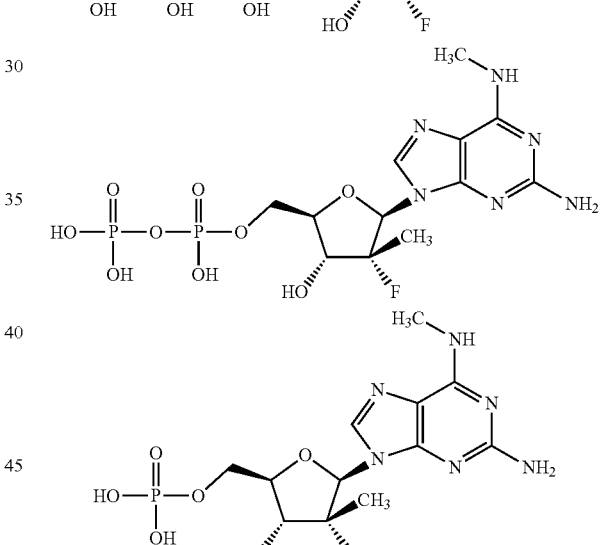
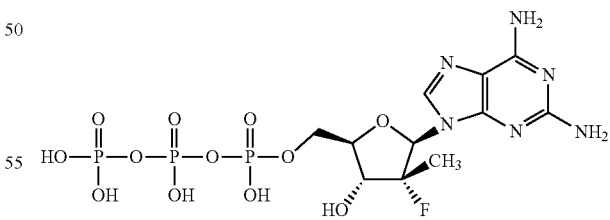
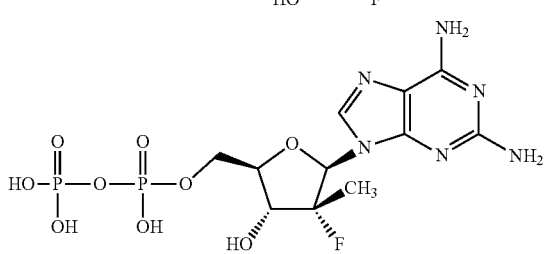

-continued

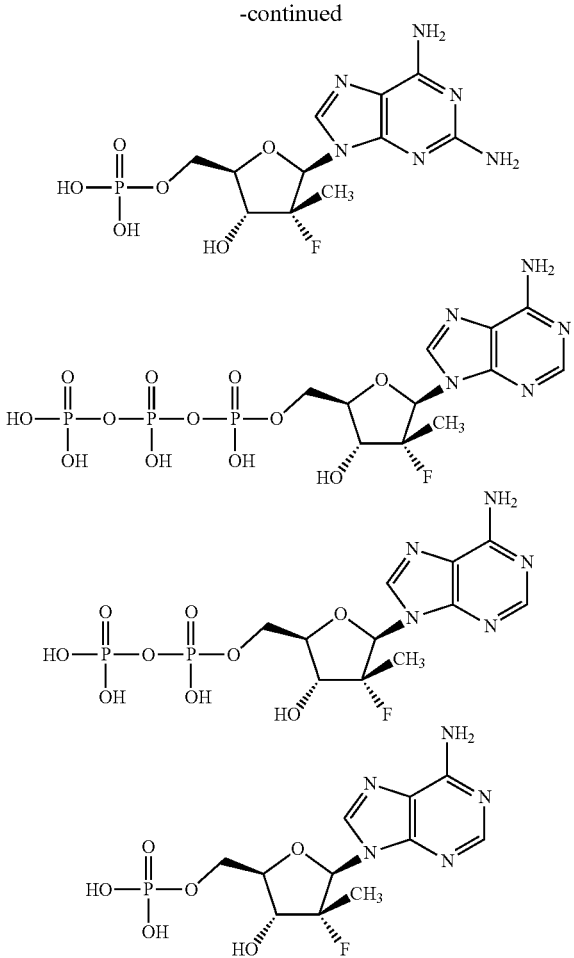

The phosphorus in any of the Formulas above may be chiral and thus can be provided as an R or S enantiomer or a mixture thereof, including a racemic mixture. The compound is typically at least 90% free of the opposite enantiomer, and can be at least 95%, 96%, 97%, 98%, 99% or even 100% free of the opposite enantiomer (e.g., enantiomerically enriched). Unless described otherwise, the compound is at least 90% free of the opposite enantiomer. For example, Compound 1 is depicted without regard to stereochemistry at the phosphorus atom, which is chiral. Compound 1 can be used in a racemic form, or with any desired ratio of phosphorus $R_p$- and $S_p$-enantiomers of the compound, including enantiomerically enriched material up to pure enantiomers. Compound 1A has S-stereochemistry at the phosphorus and Compound 1B has R-stereochemistry at the phosphorus. In some embodiments, Compound 1 is used in a form at least 90% free of the opposite enantiomer, and can be at least 98%, 99% or even 100% free of the opposite enantiomer. For example, Compound 1A can be at least 90%, 95%, 98%, 99%, or even 100% free of the opposite $R_p$-enantiomer. Alternatively, Compound 1B can be at least 90%, 95%, 98%, 99%, or even 100% free of the opposite $S_p$-enantiomer.

Similarly, Compound 2 shown below is depicted without regard to stereochemistry at the phosphorus atom, which is chiral. Compound 2 can be used in a racemic form, or with any desired ratio of phosphorus R- and S-enantiomers of the compound, including enantiomerically enriched material up to pure enantiomers. Compound 2A has S-stereochemistry at the phosphorus and Compound 2B has R-stereochemistry at the phosphorus. In some embodiments, Compound 2 is used in a form at least 90% free of the opposite enantiomer, and can be at least 98%, 99% or even 100% free of the opposite enantiomer. In one embodiment, Compound 2A can be at least 90%, 95%, 98%, 99%, or even 100% free of the opposite $R_p$-enantiomer. In one embodiment, Compound 2B can be at least 90%, 95%, 98%, 99%, or even 100% free of the opposite $S_p$-enantiomer.

Unless described otherwise, compounds of the present invention that are drawn with stereochemistry at the phosphorus are at least 90% free of the opposite enantiomer.

Compounds, compositions, dosage forms, and methods are provided for the treatment of COVID-19 caused by the SARS-CoV-2 virus in a host in need thereof via administration of an effective amount of a compound of Formula I, Formula II, Formula III, Formula IV, or Formula V or a pharmaceutically acceptable salt thereof. In one embodiment, a compound of Formula I, Formula II, Formula III, Formula IV, or Formula V or a pharmaceutically acceptable salt thereof can also be used in an effective amount prophylactically to prevent or restrict the progression of COVID-19 in a host in need thereof who has been exposed to the virus or who is at risk of infection or reinfection.

The weight of active compound in the dosage form described herein is with respect to either the free form or the salt form of the compound unless otherwise specifically indicated. For example, approximately 600 mg of Compound 2 is the equivalent of approximately 550 mg of Compound 1. In one non-limiting embodiment, a loading dose is 1100 mg/day (base) (i.e., 1200 mg/day hemisulfate salt of Compound 1), and a maintenance dose is 550 mg/day (base) (i.e, 600 mg/day of hemisulfate salt)).

In certain embodiments, a compound of Formula I, Formula II, Formula III, Formula IV, or Formula V or a pharmaceutically acceptable salt thereof is administered at a dose of at least about 100, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, or 1700 mg. In certain embodiments, a compound of Formula I, Formula II, Formula III, Formula IV, or Formula V or a pharmaceutically acceptable salt thereof is administered at a dose of at least 500 mg, at least 600 mg, at least 700 mg, at least 800 mg, at least 900 mg, at least 1000 mg, at least 1100 mg, at least 1200 mg, at least 1300 mg, at least 1400 mg or at least 1500 mg.

In certain embodiments, a compound of Formula I, Formula II, Formula III, Formula IV, or Formula V or a pharmaceutically acceptable salt thereof, for example Compound 1 or Compound 3 or a pharmaceutically acceptable salt thereof, including Compound 2 or Compound 4, is administered at an initial dose (or loading dose) followed by a maintenance dose, wherein the loading dose is at the discretion of the physician based on the severity of the presented disease and the size of the patient. In certain embodiments, the loading dose is about or at least 1.5 times greater, about or at least 2 times greater, about or at least 2.5 times greater, or about or at least 3 times greater than the maintenance dose. In one embodiment, the loading dose is administered once, twice, three, four, or more times before the first maintenance dose, and may be given once, twice, three times or four times a day as instructed by the physician.

In one embodiment, a compound of Formula I, Formula II, Formula III, Formula IV, or Formula V or a pharmaceutically acceptable salt thereof, for example Compound 1 or Compound 3 or a pharmaceutically acceptable salt thereof, including Compound 2 or Compound 4, is administered at a daily loading dose (which can be provided in one or several dosages throughout the day) of at least about 800 mg, at least about 900 mg, at least about 1000 mg, at least about 1100 mg, at least about 1200 mg, at least about 1300 mg, or at least about 1400 mg followed by a maintenance dose of at least about 300 mg, at least about 350 mg, at least about 400 mg, at least about 450 mg, at least about 500 mg, at least about 550 mg, at least about 600 mg, at least about 650 mg, at least about 700 mg, or at least about 750 mg and the maintenance dose is taken once, twice, or three times a day. In one embodiment, the maintenance dose is taken twice a day, and optionally over 1, 2, 3, or 4 days. In one embodiment, the maintenance dose is thereafter administered 1, 2 or 3 times a day for at least about 4 days, at least about 5 days, at least about 6 days, at least about 7 days, at least about 8 days, at least about 9 days, at least about 10 days, at least about 15 days, at least about 20 days, at least about 25 days, or more.

In certain embodiments, Compound 1 or Compound 3 or a pharmaceutically acceptable salt thereof, including Compound 2 or Compound 4, is administered at a dose of at least about 300 mg, at least about 350 mg, at least about 400 mg, at least about 450 mg, at least about 500 mg, at least about 550 mg, at least about 650, or at least about 750 and the dose is taken once, twice, or three times a day.

In one embodiment, Compound 1 or a pharmaceutically acceptable salt thereof, for example Compound 2, is administered at a dose of at least about 500 mg, at least about 550 mg, or at least 600 mg and the dose is taken twice daily. In one embodiment, Compound 1 or a pharmaceutically acceptable salt thereof, for example Compound 2, is administered at a loading dose of at least about 1000 mg, at least about 1100 mg, or at least about 1200 mg followed by a maintenance dose of at least about 500 mg, at least about 550 mg, or at least 600 mg twice daily. In one embodiment, the maintenance dose is administered for at least about 4, 5, 6, 7, 8, 9, 10, or more days. In one embodiment, Compound 1 is Compound 1A. In one embodiment, Compound 1 is Compound 1B. In one embodiment, Compound 2 is Compound 2A. In one embodiment, Compound 2 is Compound 2B.

In certain embodiments, the method of the present invention includes administering an effective amount of a compound as described herein, such as Formula I, Formula II, Formula III, Formula IV, or Formula V or a pharmaceutically acceptable salt thereof, for example Compound 1 or Compound 2, once, twice, or three times a day as necessary to treat the infection. In one embodiment, a compound Formula I, Formula II, Formula III, Formula IV, or Formula V or a pharmaceutically acceptable salt thereof, for example Compound 1 or Compound 2, is administered for at least about 4, 5, 6, 7, 8, 9, 10, 15, 20, 25, or more days, or for a length of time at the discretion of a healthcare provider. Alternatively, the compound can be administered for a time period that is appropriate to avoid infection or reduce the severity of an infection of a human or other animal at risk of becoming infected with the virus.

In one embodiment, the compound of the present invention is administered indefinitely until the risk of infection or reinfection no longer exits. In one embodiment, a compound of Formula I, Formula II, Formula III, Formula IV, or Formula V or a pharmaceutically acceptable salt thereof is administered for at least 1 month, at least 2 months, at least 3 months, at least 4 months, at least 5 months, or at least 6 months or more. In certain embodiments, a compound of Formula I, Formula II, Formula III, Formula IV, or Formula V or a pharmaceutically acceptable salt thereof is administered once, twice, three, or four or more times a day.

In another alternative embodiment, a method to prevent transmission is provided that includes administering an effective amount of one of the compounds described herein to humans for a sufficient length of time prior to exposure to crowds that can be infected, including during travel or public events or meetings, including for example, up to 3, 5, 7, 10, 12, 14 or more days prior to a communicable situation.

The present invention thus includes the following features:

(a) A method for the treatment of the 2019 coronavirus disease (COVID-19) caused by the SARS-CoV-2 virus in a host in need thereof comprising administering an effective amount of a compound of Formula I, Formula II, Formula III, Formula IV, or Formula V or a pharmaceutically acceptable salt thereof, optionally in a pharmaceutically carrier;

(b) A method for the prevention or minimization of infection of the 2019 coronavirus disease (COVID-19) caused by the SARS-CoV-2 virus in a host in need thereof comprising administering an effective amount of a compound of Formula I, Formula II, Formula III, Formula IV, or Formula V or a pharmaceutically acceptable salt thereof, optionally in a pharmaceutically carrier;

(c) The method of (b) for the prevention of reinfection of the 2019 coronavirus disease (COVID-19) caused by the SARS-CoV-2 virus in a host in need thereof, (d) The method of (a)-(c) wherein the compound is of Formula I;

(e) The method of (a)-(c) wherein the compound is of Formula II;

(f) The method of (a)-(c) wherein the compound is of Formula III;

(g) The method of (a)-(c) wherein the compound is of Formula IV;

(h) The method of (a)-(c) wherein the compound is of Formula V;

(i) The method of (a)-(c) wherein the compound is Compound 1;

(j) The method of (a)-(c) wherein the compound is Compound 1A;

(k) The method of (a)-(c) wherein the compound is Compound 1B;

(l) The method of (a)-(c) wherein the compound is Compound 2;

(m) The method of (a)-(c) wherein the compound is Compound 2A;

(n) The method of (a)-(c) wherein the compound is Compound 2B;

(o) The method of (a)-(c) wherein the compound is Compound 3;

(p) The method of (a)-(c) wherein the compound is Compound 3A;

(q) The method of (a)-(c) wherein the compound is Compound 3B;

(r) The method of (a)-(c) wherein the compound is Compound 4;

(s) The method of (a)-(c) wherein the compound is Compound 4A;

(t) The method of (a)-(c) wherein the compound is Compound 4B;

(u) A compound of Formula I, Formula II, Formula III, Formula IV, or Formula V or a pharmaceutically acceptable salt thereof for use to treat COVID-19 in a host in need thereof, optionally in a pharmaceutically acceptable carrier;
- (v) A compound of Formula I, Formula II, Formula III, Formula IV, or Formula V or a pharmaceutically acceptable salt thereof for use to prevent or minimize (relative to without treatment) an infection of COVID-19 in a host in need thereof, optionally in a pharmaceutically acceptable carrier;
- (w) The compound of (v) to prevent a reinfection of COVID-19 in a host in need thereof;
- (x) The use of a compound of Formula I, Formula II, Formula III, Formula IV, or Formula V or a pharmaceutically acceptable salt thereof, optionally in a pharmaceutically acceptable carrier, in the manufacture of a medicament for the treatment of COVID-19;
- (y) The use of a compound of Formula I, Formula II, Formula III, Formula IV, or Formula V or a pharmaceutically acceptable salt thereof, optionally in a pharmaceutically acceptable carrier, in the manufacture of a medicament for the prevention of COVID-19 in a host in need thereof;
- (z) The use of (y) to prevent a reinfection of COVID-19 in a host in need thereof;
- (aa) Any of the above embodiments, wherein the pharmaceutically acceptable carrier is in a dosage form suitable for oral administration;
- (bb) The dosage form of (aa) wherein the dosage form is a solid dosage form;
- (cc) The dosage form of (bb) in the form of a tablet;
- (dd) The dosage form of (bb) in the form of a capsule;
- (ee) The dosage form of (aa) wherein the dosage form is a liquid dosage form;
- (ff) The dosage form of (ee) in the form of a solution or a suspension;
- (gg) Any of embodiments (a)-(z), wherein the pharmaceutically acceptable carrier is in a dosage form suitable for intravenous administration;
- (hh) Any of embodiments (a)-(z), wherein the pharmaceutically acceptable carrier is in a dosage form suitable for parenteral administration;
- (ii) Any of the above embodiments, wherein a compound of Formula I, Formula II, Formula III, Formula IV, or Formula V or a pharmaceutically acceptable salt thereof is administered once a day;
- (jj) Any of the above embodiments, wherein a compound of Formula I, Formula II, Formula III, Formula IV, or Formula V or a pharmaceutically acceptable salt thereof is administered twice a day;
- (kk) Any of the above embodiments, wherein a compound of Formula I, Formula II, Formula III, Formula IV, or Formula V or a pharmaceutically acceptable salt thereof is administered three times a day;
- (ll) Any of the above embodiments, wherein a compound of Formula I, Formula II, Formula III, Formula IV, or Formula V or a pharmaceutically acceptable salt thereof is administered for at least one month, at least two months, at least three months, at least four months, at least five months, or at least six months or more.
- (mm) Any of the above embodiments, wherein a compound of Formula I, Formula II, Formula III, Formula IV, or Formula V or a pharmaceutically acceptable salt thereof is administered at least once, at least twice, or at least three times a day indefinitely until the risk of infection no longer exists;
- (nn) Any of the above embodiments, wherein a compound of Formula I, Formula II, Formula III, Formula IV, or Formula V or a pharmaceutically acceptable salt thereof is administered at a dose of at least about 400 mg;
- (oo) Any of the above embodiments, wherein a compound of Formula I, Formula II, Formula III, Formula IV, or Formula V or a pharmaceutically acceptable salt thereof is administered at a dose of at least about 500 mg;
- (pp) Any of the above embodiments, wherein a compound of Formula I, Formula II, Formula III, Formula IV, or Formula V or a pharmaceutically acceptable salt thereof is administered at a dose of at least about 550 mg;
- (qq) Any of the above embodiments, wherein a compound of Formula I, Formula II, Formula III, Formula IV, or Formula V or a pharmaceutically acceptable salt thereof is administered at a dose of at least about 600 mg;
- (rr) A method for the treatment of COVID-19 in a host in need thereof comprising administering an effective amount of Compound 1, wherein Compound 1 is administered at a dose of at least about 550 mg and the dose is administered twice a day;
- (ss) A method for the treatment of COVID-19 in a host in need thereof comprising administering an effective amount of Compound 1, wherein Compound 1 is administered at a loading dose of at least about 1100 mg followed by a dose of at least about 550 mg twice a day;
- (tt) Embodiment (rr or ss) wherein Compound 1 is Compound 1A;
- (uu) Embodiment (rr or ss) wherein Compound 1 is Compound 1B;
- (vv) A method for the treatment of COVID-19 in a host in need thereof comprising administering an effective amount of Compound 2, wherein Compound 2 is administered at a dose of at least about 600 mg and the dose is administered twice a day;
- (ww) A method for the treatment of COVID-19 in a host in need thereof comprising administering an effective amount of Compound 2, wherein Compound 2 is administered at a loading dose of at least about 1200 mg followed by a dose of at least about 600 mg twice a day;
- (xx) Embodiment (vv or ww) wherein Compound 2 is Compound 2A;
- (yy) Embodiment (vv or ww) wherein Compound 2 is Compound 2B;
- (zz) A compound of Formula II or a pharmaceutically acceptable salt thereof;
- (aaa) Compound 4 or a pharmaceutically acceptable salt as described herein;
- (bbb) Compound 4A and Compound 4B as described herein;
- (ccc) A pharmaceutical formulation comprising an effective amount of a compound of Formula II, optionally in a pharmaceutically acceptable carrier.

DETAILED DESCRIPTION OF THE INVENTION

Figure 1:
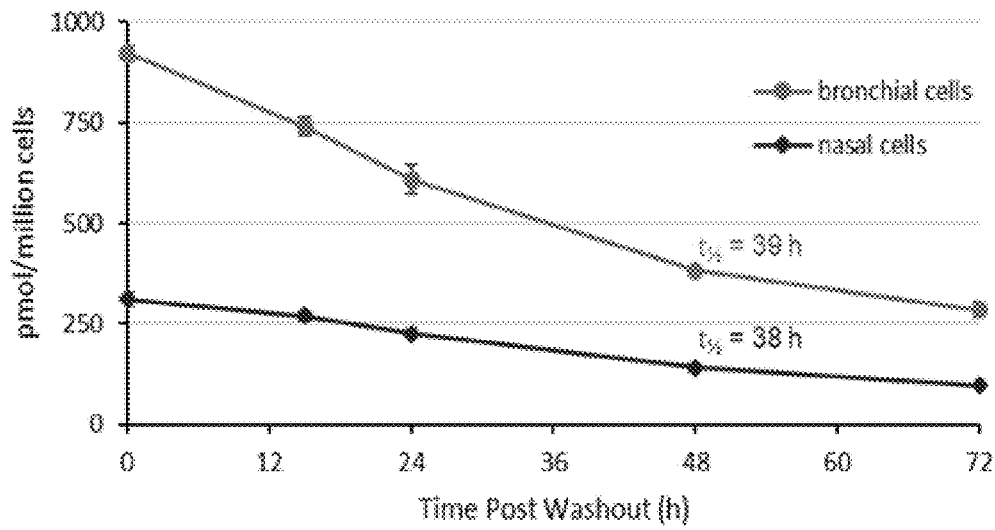
FIG. 1 is a graph of the concentration of triphosphate Compound 1-6 in human bronchial and nasal epithelial cells after exposure to 10 μM of Compound 1A as described in Example 7. The half-life of Compound 1-6 in bronchial cells and nasal cells was 39 hours and 38 hours, respectively. The x-axis is the time post-washout measured in hours and the y-axis is the concentration of Compound 1-6 in pmol/million cells.

The invention disclosed herein is a method for the treatment or prevention of the 2019 coronavirus disease (COVID-19) caused by the SARS-CoV-2 virus in a host in need thereof comprising administering an effective amount of a compound of Formula I or a pharmaceutically acceptable salt thereof:

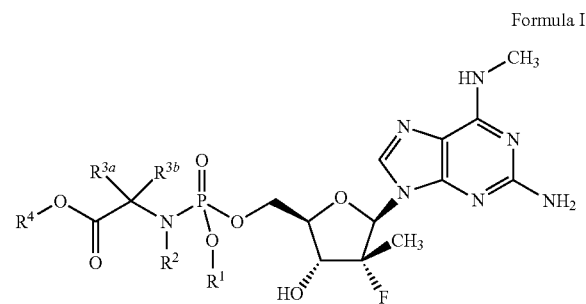

Formula I wherein
$R^1$ is hydrogen, $C_{1-6}$alkyl (including methyl, ethyl, propyl, and isopropyl), $C_{3-7}$cycloalkyl, or aryl (including phenyl and napthyl) and in an alternative embodiment, $R^1$ is aryl-$C_{1-4}$alkyl (including benzyl);
$R^2$ is hydrogen or $C_{1-6}$alkyl (including methyl, ethyl, propyl, and isopropyl);
$R^{3a}$ and $R^{3b}$ are independently selected from hydrogen, $C_{1-6}$alkyl (including methyl, ethyl, propyl, and isopropyl), and $C_{3-7}$cycloalkyl; and
$R^4$ is hydrogen, $C_{1-6}$alkyl (including methyl, ethyl, propyl, and isopropyl), $C_{1-6}$haloalkyl, or $C_{3-7}$cycloalkyl and in an alternative embodiment, $R^4$ is aryl-$C_{1-4}$alkyl (including benzyl).

Non-limiting examples of a compound of Formula I include Compound 1 and Compound 2. In one embodiment, the compounds are administered as the S-enantiomer, such as Compound 1A. In one embodiment, the compounds are administered as the R-enantiomer, such as Compound 1B. In one embodiment, a compound of Formula I is Compound 2, Compound 2A, or Compound 2B.

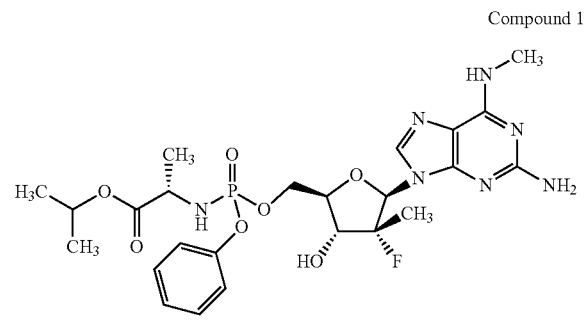

Compound 1

Compound 2
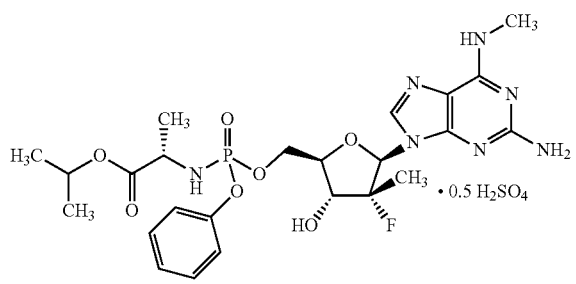
Compound 1A
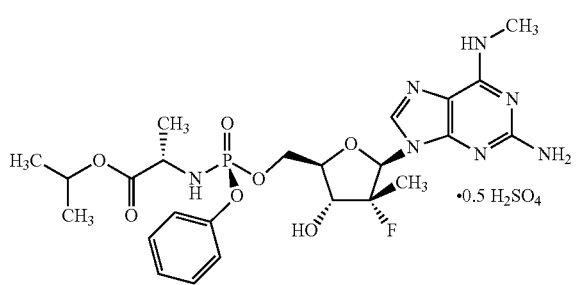
Compound 1B
Compound 2A
Compound 2B
Alternative configurations of Compound 1 or a pharmaceutically acceptable salt thereof that can be used include:
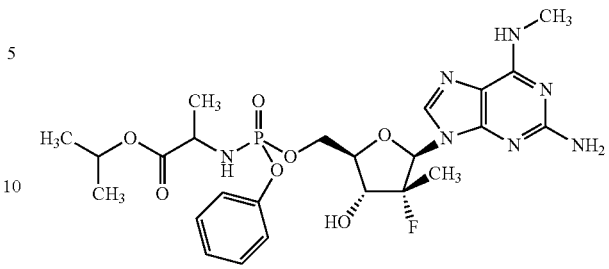
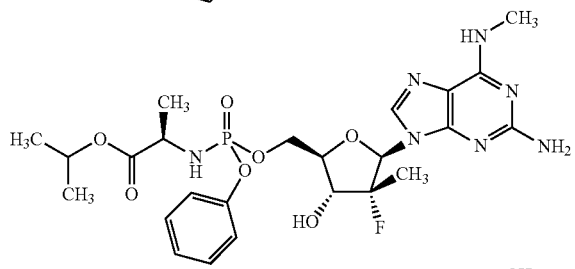
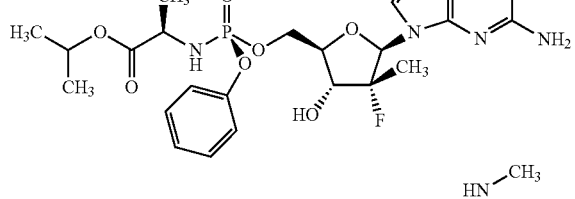
Alternative configurations of Compound 2 that can be used include:
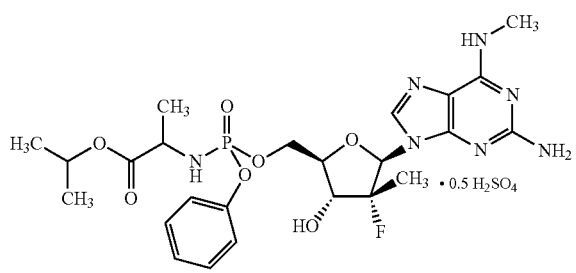
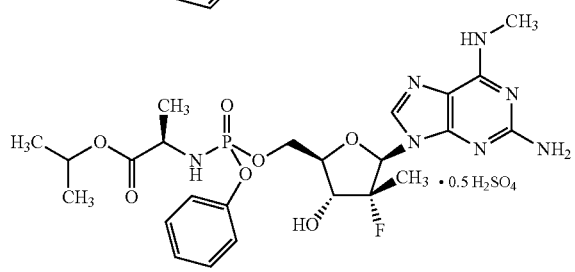

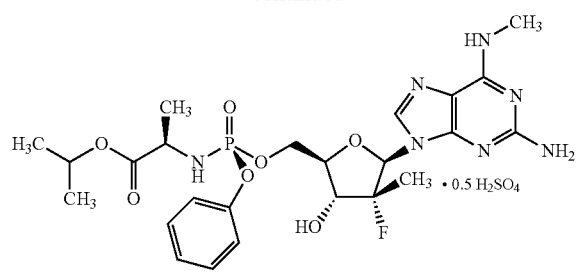
Additional non-limiting examples of a compound of Formula I include:
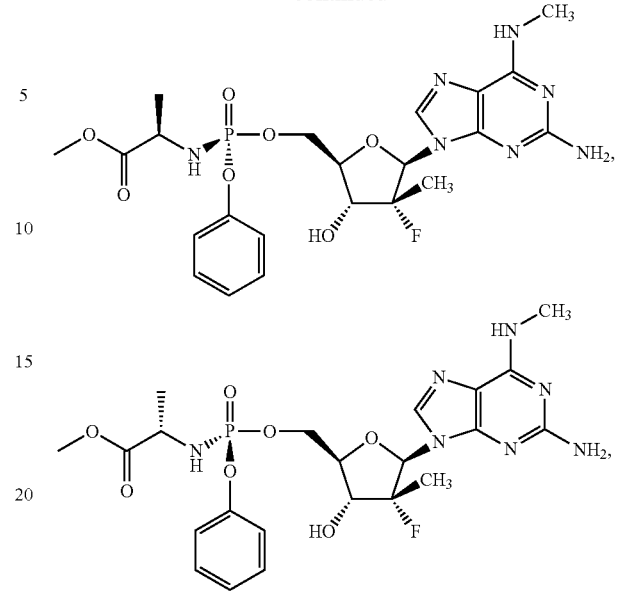
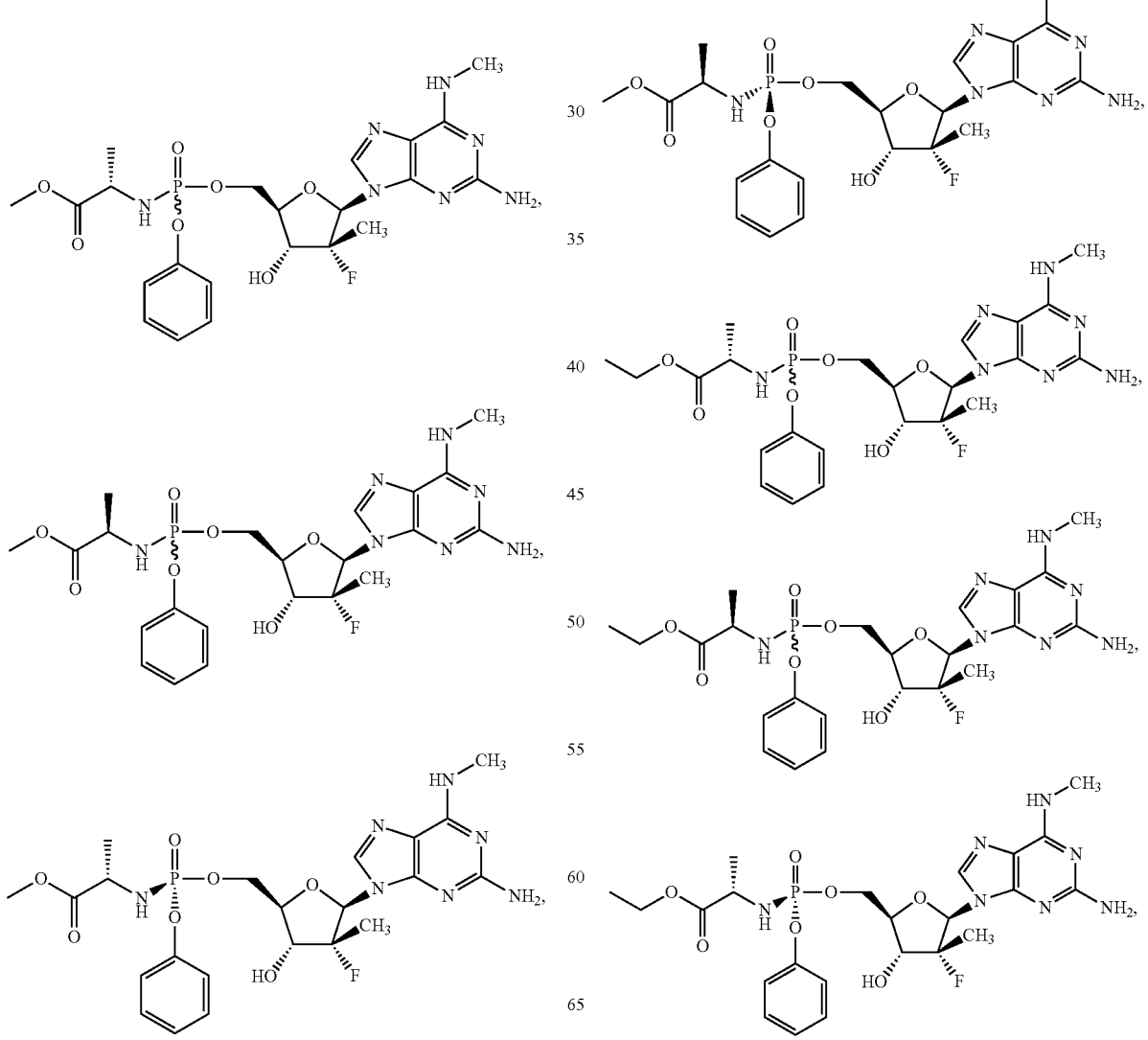

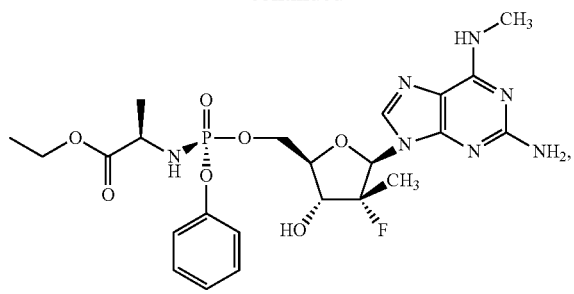
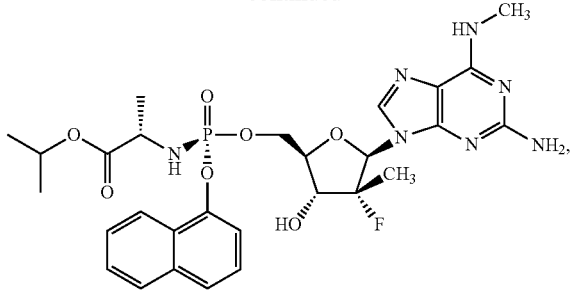 [SMILES: CNc1nc(N)nc2c1ncn2[C@@H]1O[C@H](CO[P@](=O)(N[C@@H](C)C(=O)OC(C)C)Oc2cccc3ccccc23)[C@@H](O)[C@@]1(C)F]
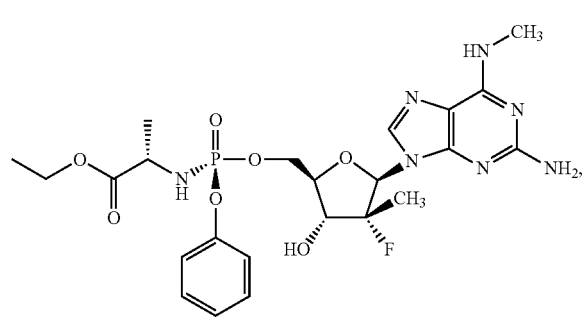
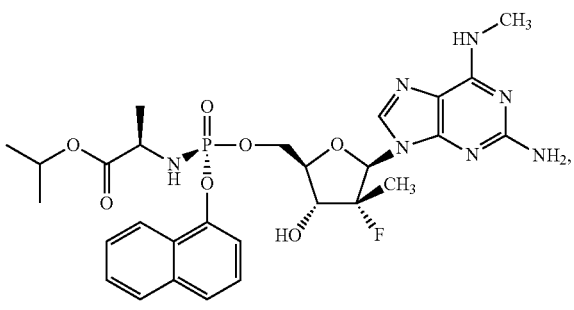
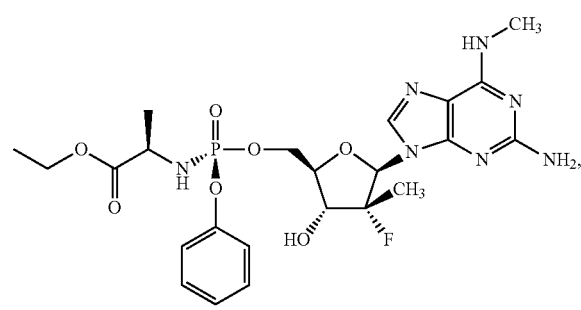
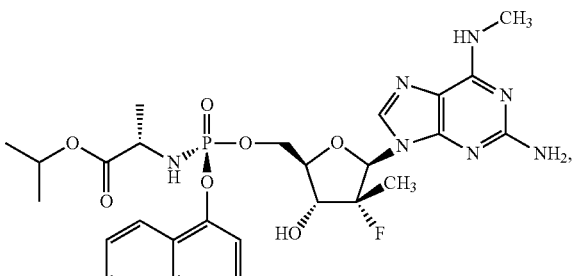
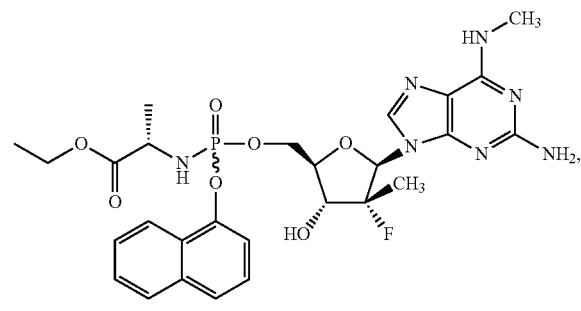
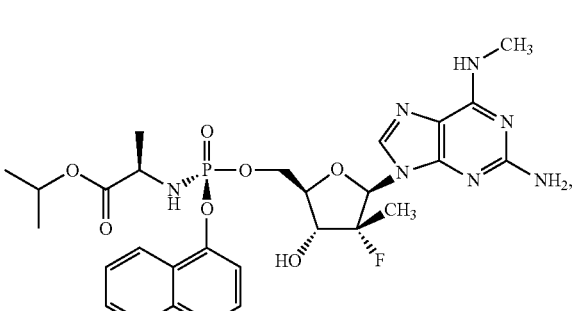
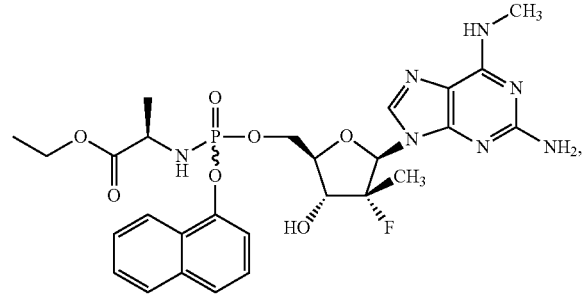
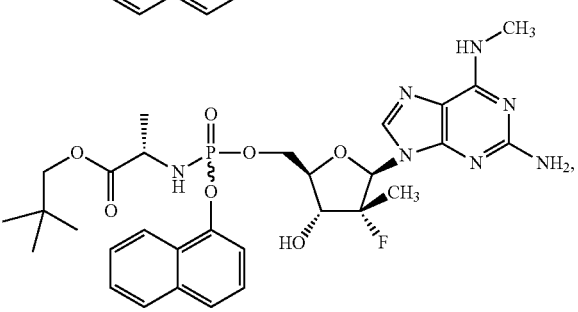

-continued

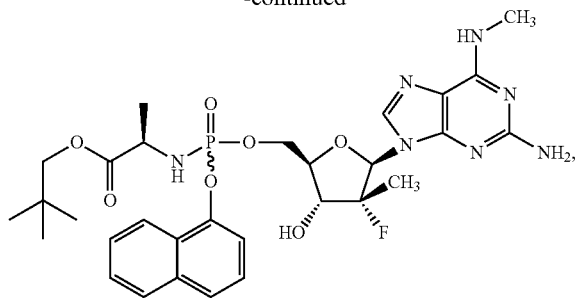

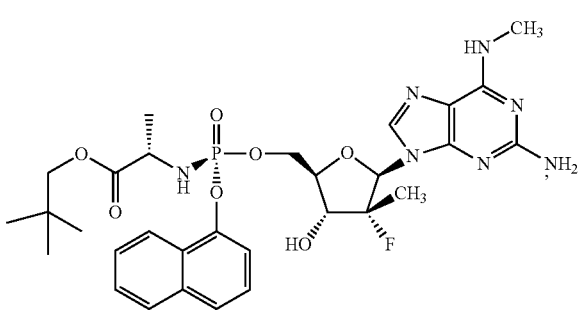

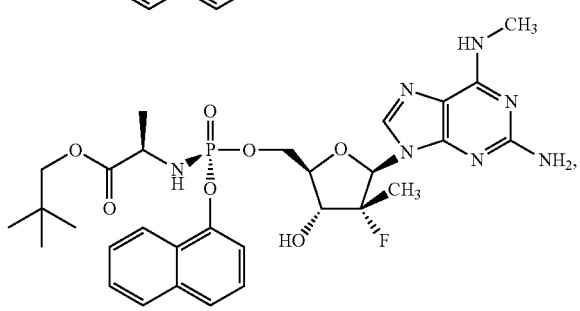

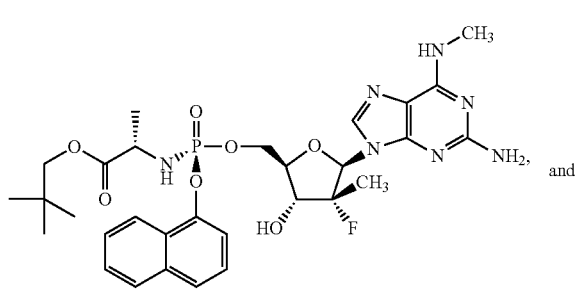

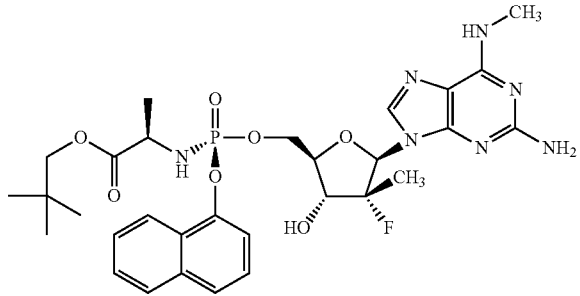

or a pharmaceutically acceptable salt thereof.

The present invention also includes the use of an effective amount of a compound of Formula II to treat or prevent COVID-19 in a host in need thereof:

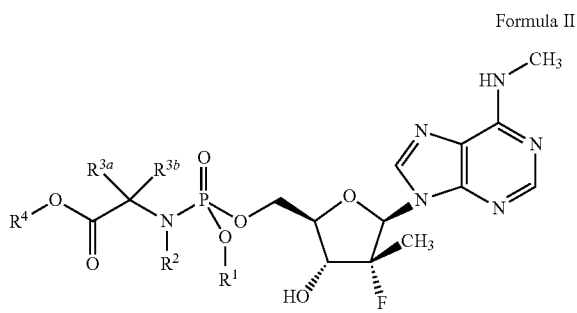

Formula II or a pharmaceutically acceptable salt thereof, wherein:
$R^1$ is hydrogen, $C_{1-6}$alkyl (including methyl, ethyl, propyl, and isopropyl), $C_{3-7}$cycloalkyl, or aryl (including phenyl and napthyl) and in an alternative embodiment, $R^1$ is aryl-$C_{1-4}$alkyl (including benzyl);
$R^2$ is hydrogen or $C_{1-6}$alkyl (including methyl, ethyl, propyl, and isopropyl);
$R^{3a}$ and $R^{3b}$ are independently selected from hydrogen, $C_{1-6}$alkyl (including methyl, ethyl, propyl, and isopropyl), and $C_{3-7}$cycloalkyl; and
$R^4$ is hydrogen, $C_{1-6}$alkyl (including methyl, ethyl, propyl, and isopropyl), $C_{1-6}$haloalkyl, or $C_{3-7}$cycloalkyl and in an alternative embodiment, $R^4$ is aryl-$C_{1-4}$alkyl (including benzyl).

In one embodiment, a compound of Formula II or a pharmaceutically acceptable salt thereof, optionally in a pharmaceutically acceptable carrier, is administered in an effective amount to a host in need thereof infected with SARS-CoV-2, or at risk of infection with SARS-CoV-2, i.e., as a prophylactic.

Non-limiting examples of a compound of Formula II include Compound 3 and Compound 4. In one embodiment, the compounds are administered as the S-enantiomer, such as Compound 3A and Compound 4A. In one embodiment, the compounds are administered as the R-enantiomer, such as Compound 3B or Compound 4B.

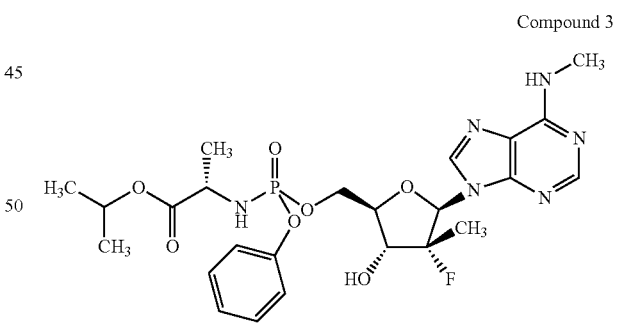

Compound 3

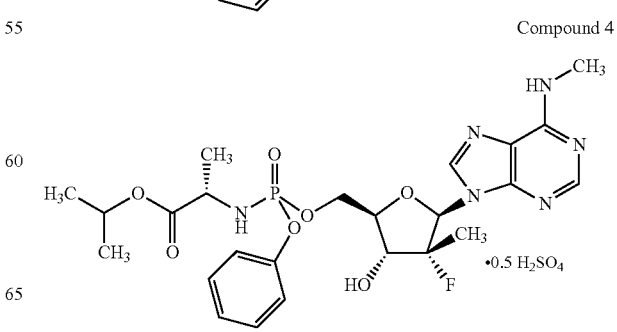

Compound 4

Compound 3A
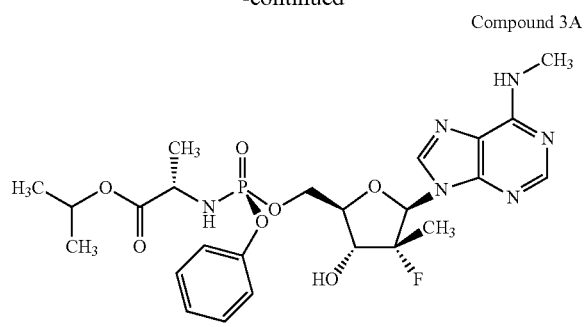
Compound 3B
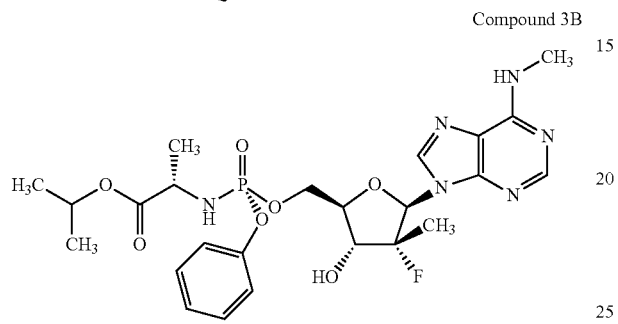
Compound 4A
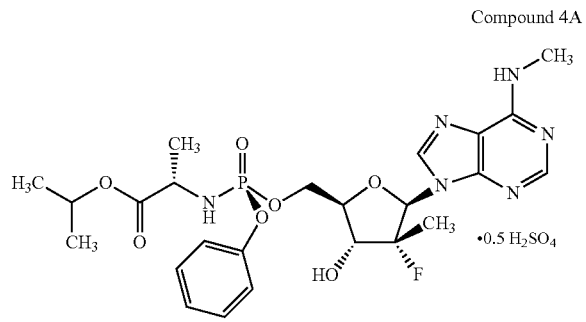
Compound 4B
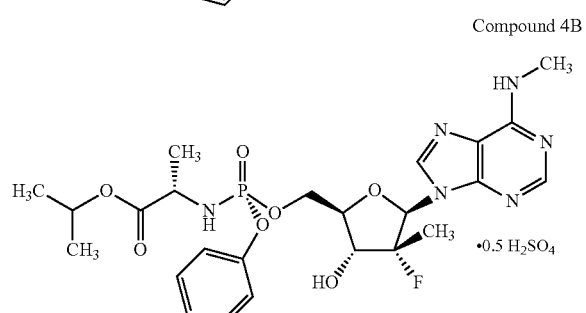
Alternative configurations of Compound 3 or a pharmaceutically acceptable salt thereof include:
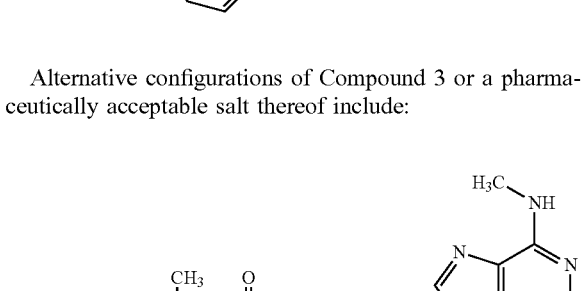
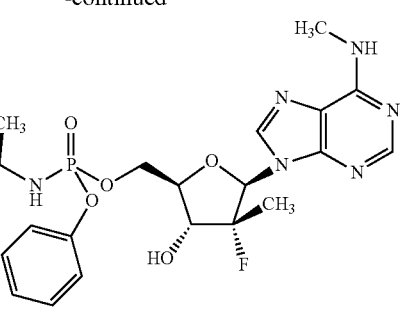
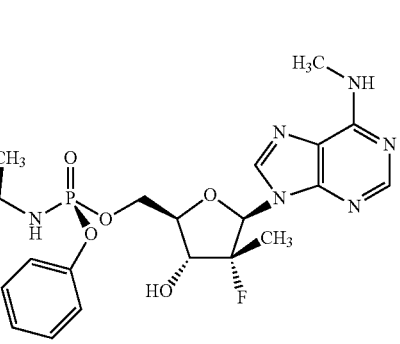
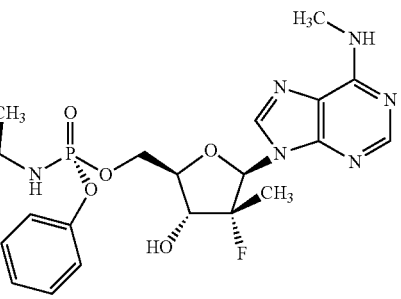
Additional alternative configurations of Compound 4 include:
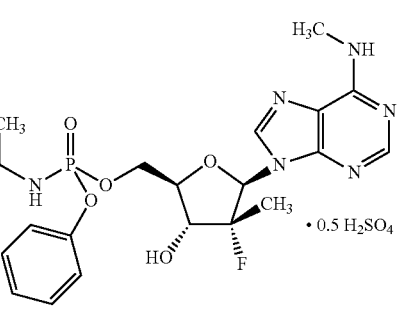
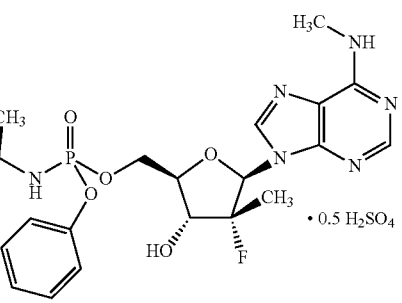

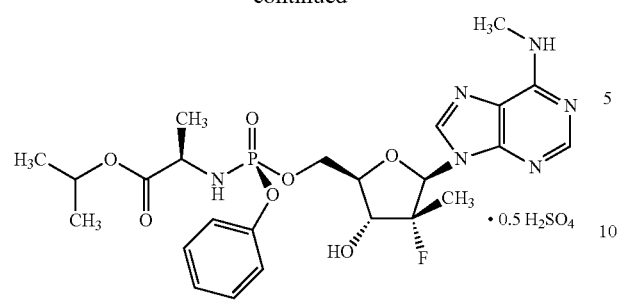
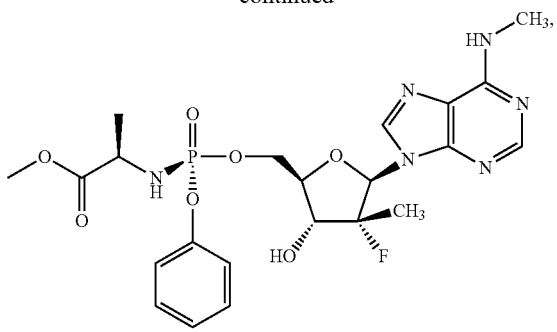
Additional non-limiting examples of a compound of Formula II include:
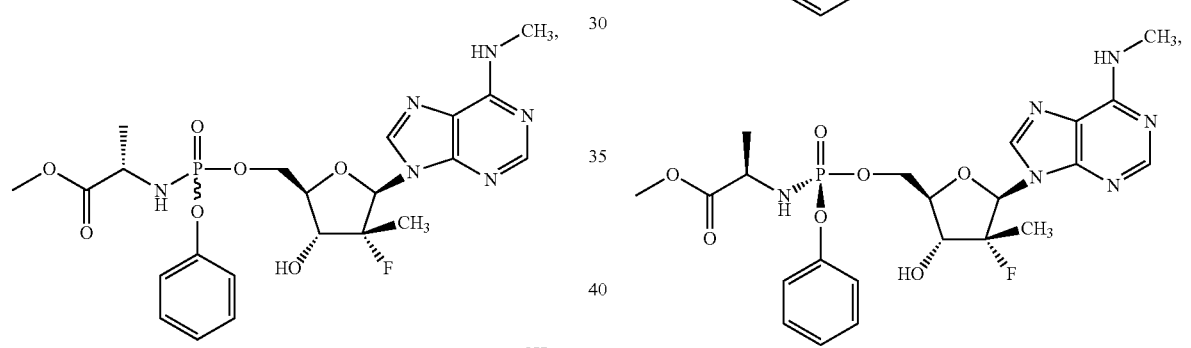
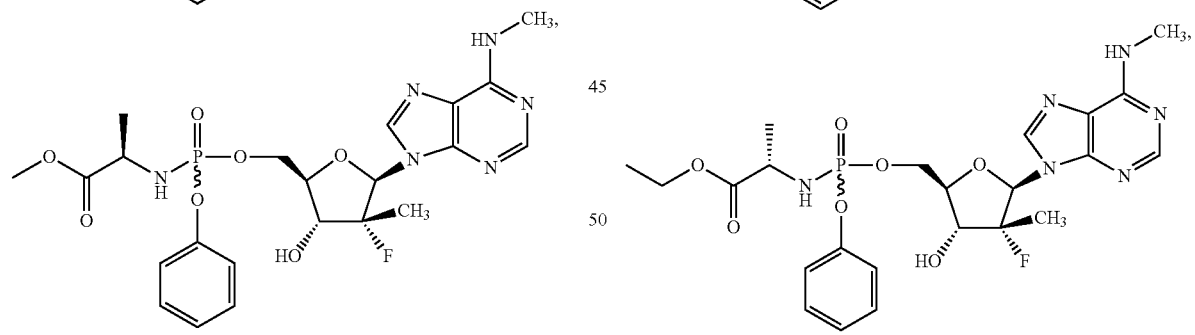
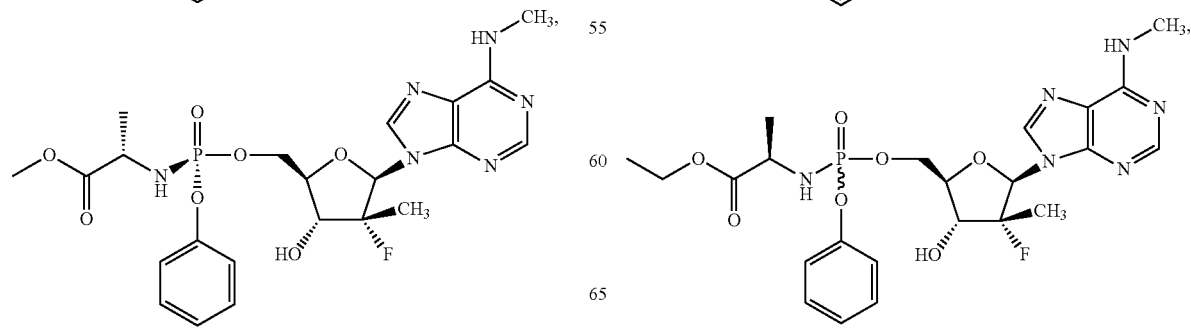

31
-continued
32
-continued
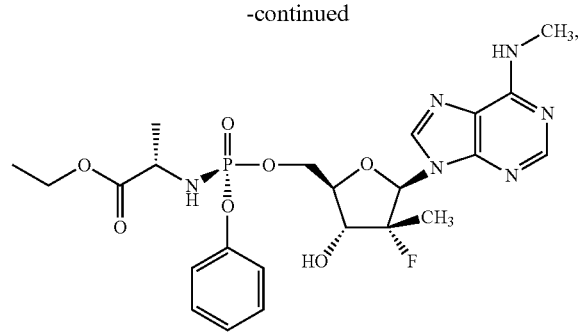
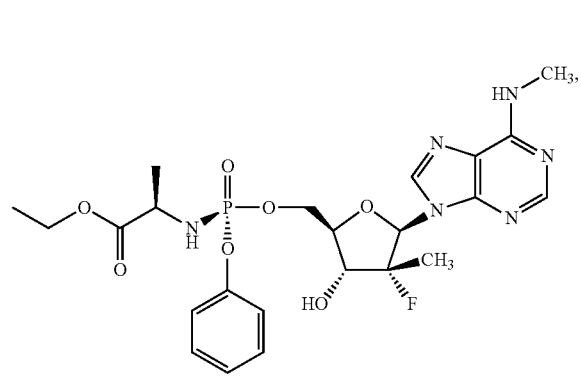
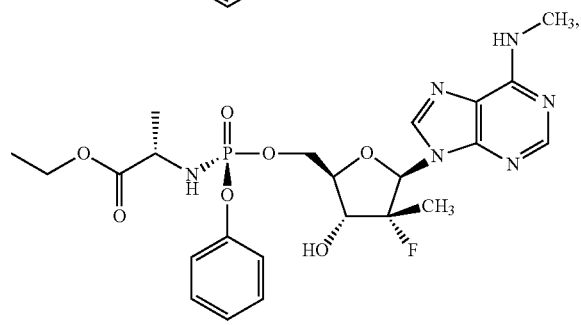
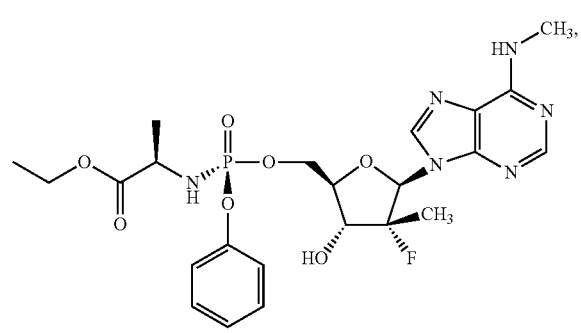
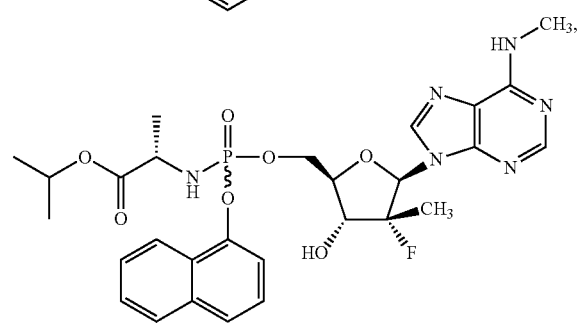

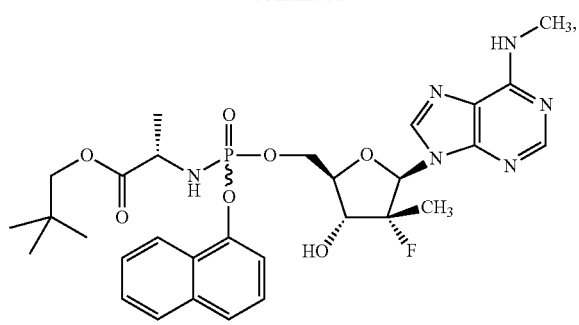

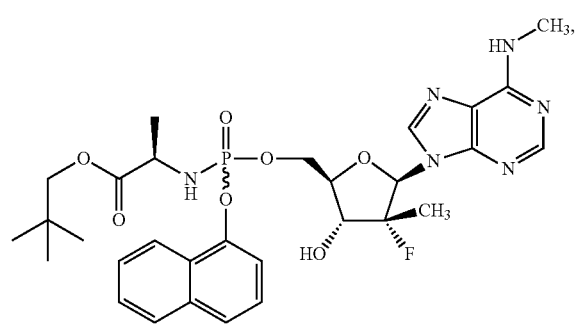

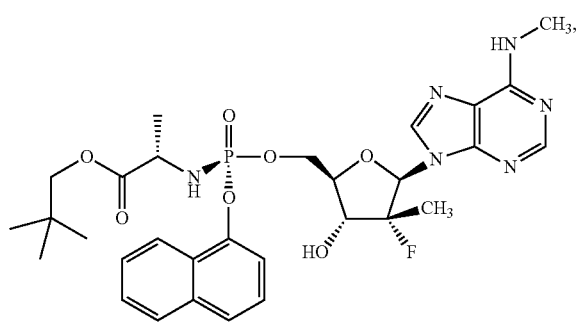

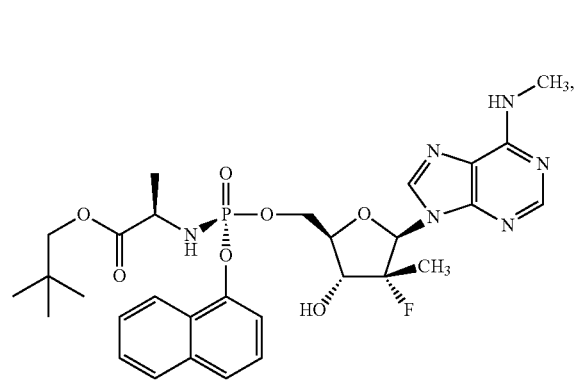

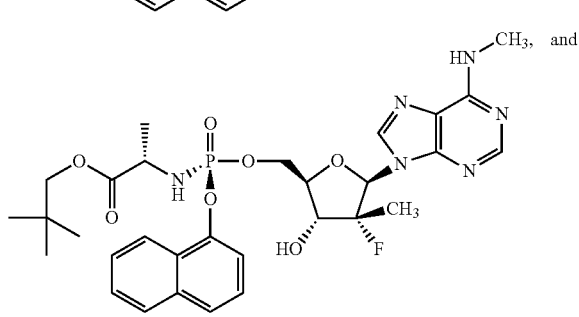

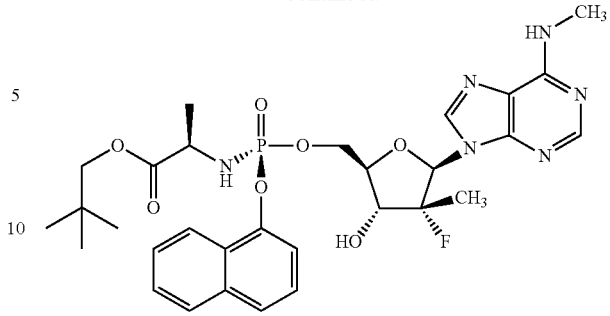

or a pharmaceutically acceptable salt thereof.

The present invention also includes the use of a compound of Formula III, Formula IV, or Formula V wherein $R^5$ is a monophosphate, a diphosphate, a triphosphate, or $R^6$ wherein $R^6$ is a stabilized phosphate prodrug that metabolizes in vivo to a monophosphate, diphosphate, or triphosphate to treat or prevent COVID-19 disease in a host in need thereof as described herein:

Formula III

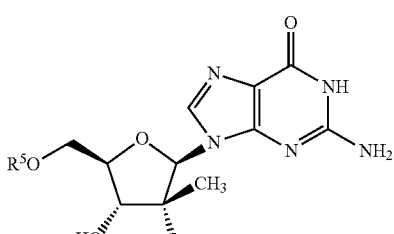

Formula IV

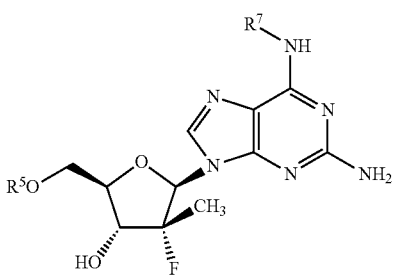

Formula V

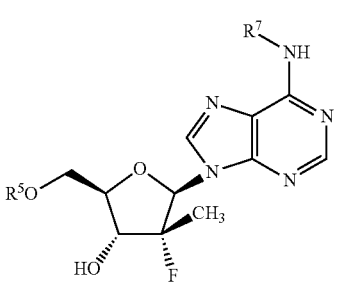

wherein
$R^5$ is selected from

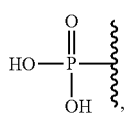

-continued

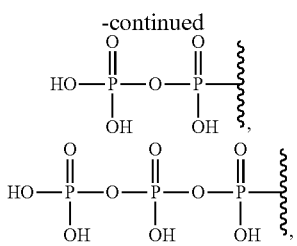

or R[6];

R[6] is a stabilized phosphate prodrug that metabolizes in vivo to a monophosphate, diphosphate, or triphosphate; and R[7] is selected from hydrogen and methyl.

In some embodiments, a compound of Formula I, Formula II, Formula III, Formula IV, or Formula V, for example Compound 1A, Compound 1B, Compound 2A, Compound 2B, Compound 3A, Compound 3B, Compound 4A, or Compound 4B is used in a form at least 90% free of the opposite enantiomer, and can be at least 98%, 99% or even 100% free of the opposite enantiomer.

Compound 1 (isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate) was previously described in U.S. Pat. Nos. 9,828,410; 10,000,523; 10,005,811; and 10,239,911 and PCT Applications WO 2016/144918; WO 2018/048937; WO 2019/200005; and, WO 2020/117966 assigned to Atea Pharmaceuticals. The synthesis of Compound 1 is described in Example 1 below.

Compound 2 was previously disclosed in U.S. Pat. No. 10,519,186 and PCT Applications WO 2018/144640; WO 2019/200005; and, WO 2020/117966 assigned to Atea Pharmaceuticals. Compound 2A has demonstrated potent in vitro activity against clinical isolates of hepatitis C virus (HCV) by inhibiting the RNA-dependent RNA polymerase (RdRp) (Good, S. S. et al. *PLoS ONE* 15(1), e0227104 (2020)). Compound 2A has been evaluated in a Phase 1B study (Berliba, E. et al. *Antimicrob. Agents Chemther.* 63, e011201-19 (2020)) and a Phase 2 clinical trial (Mungar, Q. et al. EASL abstract (2020)). In the latter study, Compound 2A was safe and well-tolerated for up to 12 weeks in HCV-infected subjects and achieved a high rate of efficacy.

The synthesis of Compound 2 (the hemi-sulfate salt of isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate) is described in Example 2 below.

In one embodiment Compound 2 is provided in a pharmaceutically acceptable composition or solid dosage form thereof.

A non-limiting illustrative process for the preparation of Compound 2 includes
(i) a first step of dissolving Compound 1 in an organic solvent, for example, acetone, ethyl acetate, methanol, acetonitrile, or ether, or the like, in a flask or container;
(ii) charging a second flask or container with a second organic solvent, which may be the same as or different from the organic solvent in step (i), optionally cooling the second solvent to 0-10 degrees C., and adding dropwise $H_2SO_4$ to the second organic solvent to create a $H_2SO_4$/organic solvent mixture; and wherein the solvent for example may be methanol;
(iii) adding dropwise the $H_2SO_4$/solvent mixture at a molar ratio of 0.5/1.0 from step (ii) to the solution of Compound 1 of step (i) at ambient or slightly increased or decreased temperature (for example 23-35 degrees C.);
(iv) stirring the reaction of step (iii) until precipitate of Compound 2 is formed, for example at ambient or slightly increased or decreased temperature;
(v) optionally filtering the resulting precipitate from step (iv) and washing with an organic solvent; and
(vi) optionally drying the resulting Compound 2 in a vacuum, optionally at elevated a temperature, for example, 55, 56, 57, 58, 59, or 60° C.

In one embodiment, the solvent of step (iii) is an alcohol, for example methanol, ethanol, or isopropyl alcohol. In one embodiment, the solvent of step (iii) is an alkyl ester, for example ethyl acetate.

Scheme 1 provides the metabolic pathway of a compound of Formula I, which involves the initial de-esterification of the phosphoramidate (Compound 1) to form metabolite 1-1, which spontaneously decomposes to metabolite 1-2. Metabolite 1-2 is next converted to the N[6]-methyl-2,6-diaminopurine-5'-monophosphate derivative (metabolite 1-3), which is in turn metabolized to the free 5'-hydroxyl-N[6]-methyl-2,6-diaminopurine nucleoside (metabolite 1-8) and ((2R,3R,4R,5R)-5-(2-amino-6-oxo-1,6-dihydro-9H-purin-9-yl)-4-fluoro-3-hydroxy-4-methyltetrahydrofuran-2-yl) methyl dihydrogen phosphate as the 5'-monophosphate (metabolite 1-4). Metabolite 1-4 is anabolized to the corresponding diphosphate (metabolite 1-5) and then the active triphosphate derivative (metabolite 1-6). The 5'-triphosphate can be further metabolized to generate 2-amino-9-((2R,3R,4R,5R)-3-fluoro-4-hydroxy-5-(hydroxymethyl)-3-methyltetrahydrofuran-2-yl)-1,9-dihydro-6H-purin-6-one (1-7). Metabolite 1-7 is measurable in plasma and is therefore a surrogate for the active triphosphate (1-6), which is not measurable in plasma.

Scheme 1

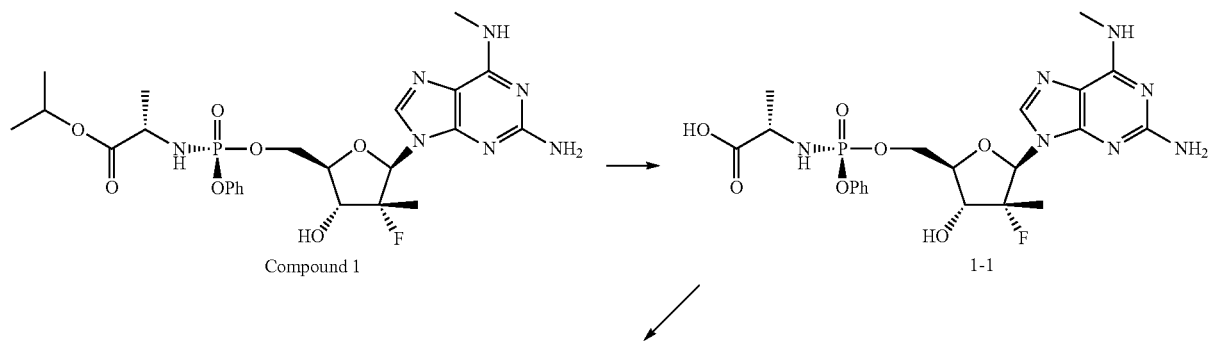

Compound 1 → 1-1

-continued

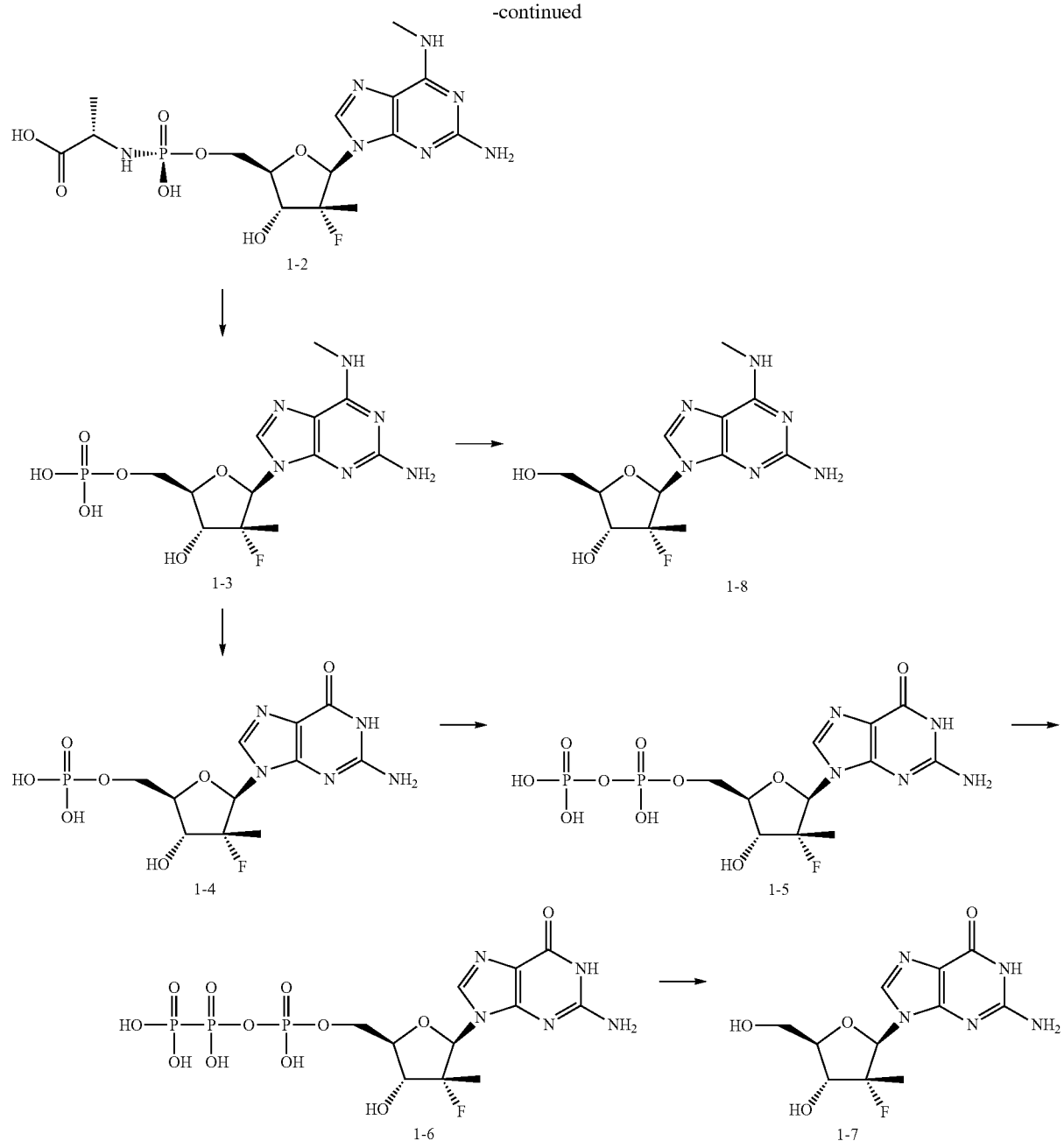

Definitions

A "patient" or "host" or "subject" is a human or non-human animal in need of treatment or prevention of COVID-19 caused by the SARS-CoV-2 virus. Typically, the host is a human. A "patient" or "host" or "subject" also refers to, for example, a mammal, primate (e.g., human), cow, sheep, goat, horse, dog, cat, rabbit, rat, mice, bird and the like.

The term "prophylactic" or "preventative" when used refers to the administration of an active compound to prevent, reduce the likelihood of an occurrence or a reoccurrence of COVID-19, or to minimize a new infection relative to infection that would occur without such treatment. The present invention includes both treatment and prophylactic or preventative therapies. In one embodiment, the active compound is administered to a host who has been exposed to and is thus at risk of contracting COVID-19. In another alternative embodiment, a method to prevent transmission is provided that includes administering an effective amount of one of the compounds described herein to humans for a sufficient length of time prior to exposure to crowds that can be infected, including during travel or public events or meetings, including for example, up to 3, 5, 7, 10, 12, 14 or more days prior to a communicable situation.

The terms "coadminister," "coadministration," or "in combination" are used to describe the administration of a compound of Formula I, Formula II, Formula III, Formula IV, or Formula V or a pharmaceutically acceptable salt thereof, according to the present invention in combination with at least one other antiviral active agent. The timing of the coadministration is best determined by the medical specialist treating the patient. It is sometimes desired that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

A "pharmaceutically acceptable salt" is a derivative of the disclosed compound in which the parent compound is modified to an inorganic and organic, acid or base addition salt thereof without undue toxicity. The salts of the present compounds can be synthesized from the parent compound with a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds may optionally be provided in the form of a solvate.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids that are not unduly toxic. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

The compound can be delivered in any molar ratio of salt that delivers the desired result. For example, the compound can be provided with less than a molar equivalent of a counter ion, such as in the form of a hemi-sulfate salt. Alternatively, the compound can be provided with more than a molar equivalent of counter ion, such as in the form of a di-sulfate salt. Non-limiting examples of molar ratios of the compound to the counter ion include 1:0.25, 1:0.5, 1:1, and 1:2.

"Alkyl" is a straight chain or branched saturated aliphatic hydrocarbon group. In certain embodiments, the alkyl is $C_1$-$C_2$, $C_1$-$C_3$, $C_1$-$C_4$, $C_1$-$C_5$, or $C_1$-$C_6$ (i.e., the alkyl chain can be 1, 2, 3, 4, 5, or 6 carbons in length). The specified ranges as used herein indicate an alkyl group with length of each member of the range described as an independent species. For example, $C_1$-$C_6$ alkyl as used herein indicates an alkyl group having from 1, 2, 3, 4, 5, or 6 carbon atoms and is intended to mean that each of these is described as an independent species and $C_1$-$C_4$ alkyl as used herein indicates an alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane and 2,3-dimethylbutane.

"Cycloalkyl" is a saturated mono-cycle hydrocarbon ring system. Non-limiting examples of cycloalkyl groups include cyclopropyl, cyclobutyl, cyclopentyl, and cyclohexyl.

"Alkenyl" refers to a non-aromatic hydrocarbon group which contains at least one double bond between adjacent carbon atoms and a similar structure to an alkyl group as otherwise described herein. For example, an alkenyl group can have to 4 carbon atoms (i.e., $C_2$-$C_4$ alkenyl). Examples of suitable alkenyl groups include, but are not limited to, ethenyl or vinyl (—CH═CH$_2$), allyl (—CH$_2$CH═CH$_2$), 1-butenyl (—C═CH—CH$_2$CH$_3$) and 2-butenyl (—CH$_2$CH═CHCH$_2$).

The term "alkynyl" refers to a non-aromatic hydrocarbon group containing at least one triple bond between adjacent carbon atoms and a similar structure to an alkyl group as otherwise described herein. For example, an alkynyl group can have 2 to 4 carbon atoms (i.e., $C_2$-$C_4$ alkynyl). Examples of alkynyl groups include, but are not limited to ethynyl and propargyl.

"Aryl" indicates aromatic groups containing only carbon in the aromatic ring or rings. In one embodiment, the aryl groups contain 1 to 3 separate or fused rings and is 6 to about 14 or 18 ring atoms, without heteroatoms as ring members. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above. In one embodiment, aryl groups include, for example, dihydroindole, dihydrobenzofuran, isoindoline-1-one and indolin-2-one.

"Arylalkyl" is an alkyl group as described herein substituted with an aryl group as described herein. Examples include benzyl, 2-phenyl(alkyl), 3-phenyl(alkyl), and napthyl(alkyl).

The term phosphoramidate is used throughout the specification to describe a moiety at the 5' position of the furanose ring of the nucleoside and forms a prodrug form of the nucleoside compound, wherein the phosphorus atom is linked through a 5'-O— bond and wherein the phosphorus is also covalently bound to at least one nitrogen, forming a P—N bond. In some embodiments, the phosphorus is covalently linked to the amino moiety of a natural or synthetic amino acid (which may be in the form of an ester). Phosphoramidate groups for use in the present invention include, for example, those of the structures:

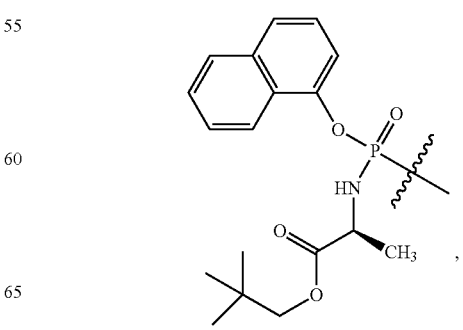

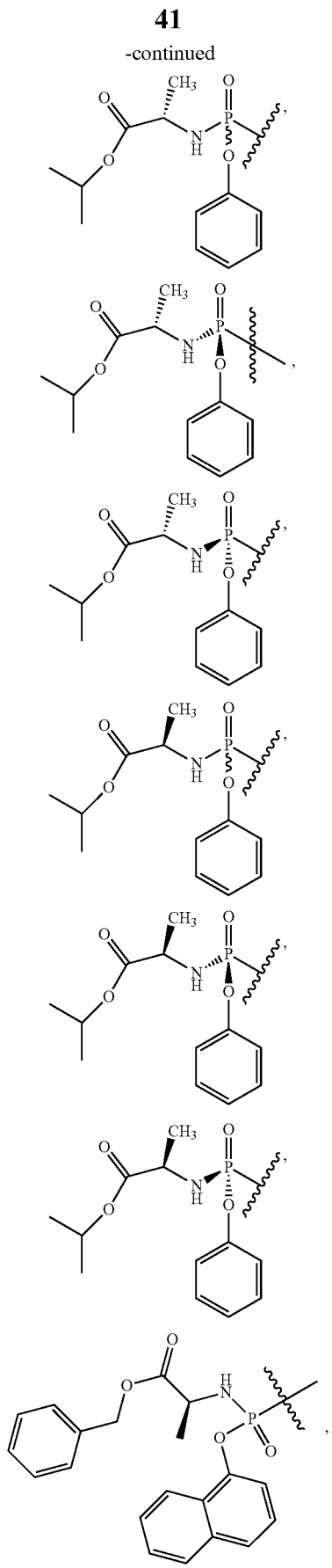

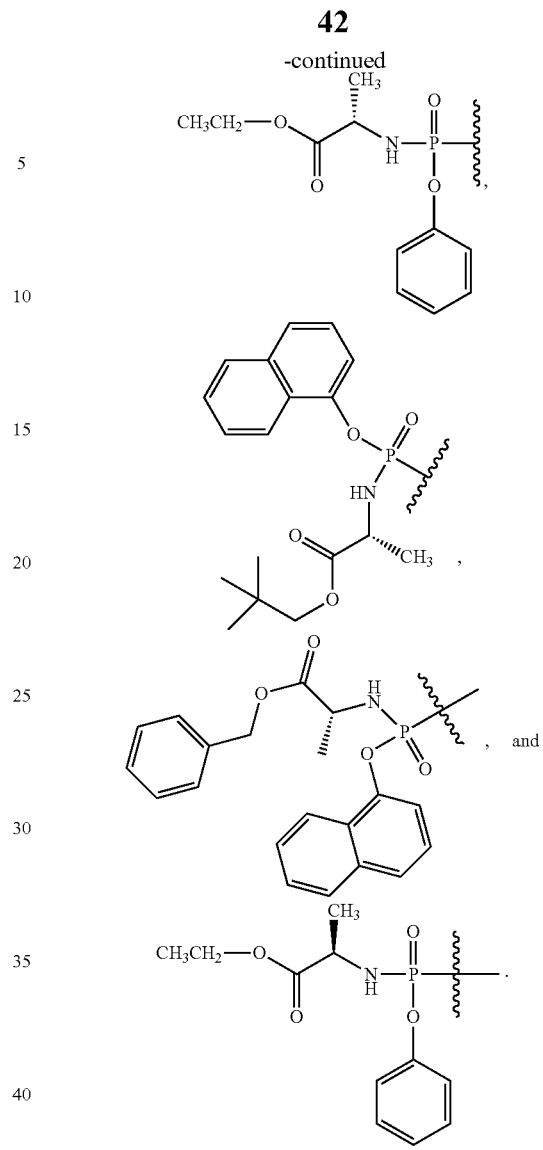

Other phosphoramidates for use in the present invention include those of the structure:

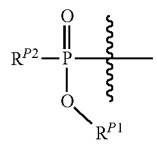

wherein:
$R^{P1}$ is an optionally substituted linear, branched, or cyclic alkyl group, or an optionally substituted aryl, heteroaryl or heterocyclic group or a linked combination thereof; and
$R^{P2}$ is a —$NR^{N1}R^{N2}$ group or a B' group;
wherein:
$R^{N1}$ and $R^{N2}$ are each independently H, $C_{1-8}$alkyl, ($C_3$-$C_7$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alky-; which may be optionally substituted; or
$R^{N1}$ and $R^{N2}$ along with the nitrogen atom to which that are attached, join to form a 3 to 7 membered heterocyclic ring;

B' is a

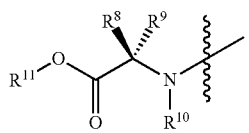

group;
wherein:
R[8] is hydrogen, (C$_1$-C$_8$)alkyl, (C$_2$-C$_8$)alkenyl, (C$_2$-C$_8$) alkynyl, (C$_3$-C$_8$cycloalkyl)C$_0$-C$_4$alkyl-, (aryl)C$_0$-C$_4$alkyl-, (C$_3$-C$_6$heterocyclo)C$_0$-C$_4$alkyl-, (heteroaryl)C$_0$-C$_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often R[8] is hydrogen, methyl, isopropyl, or isobutyl);

R[9] is hydrogen, (C$_1$-C$_8$)alkyl, (C$_2$-C$_8$)alkenyl, (C$_2$-C$_8$) alkynyl, (C$_3$-C$_8$cycloalkyl)C$_0$-C$_4$alkyl-, (aryl)C$_0$-C$_4$alkyl-, (C$_3$-C$_6$heterocyclo)C$_0$-C$_4$alkyl-, (heteroaryl)C$_0$-C$_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often R[9] is hydrogen, methyl, isopropyl, or isobutyl);

R[10] is hydrogen or C$_1$-C$_3$alkyl; or
R[8] and R[9] can form a (C$_3$-C$_7$)cycloalkyl or (C$_3$-C$_7$) heterocyclic group; or
R[10] and R[8] or R[9] can form (C$_3$-C$_6$)heterocyclic group; and
R[11] is hydrogen, (C$_1$-C$_6$)alkyl, (C$_3$-C$_6$)alkenyl, (C$_3$-C$_6$) alkynyl, (C$_3$-C$_8$cycloalkyl)C$_0$-C$_4$alkyl, (aryl)C$_0$-C$_4$alkyl-, (C$_3$-C$_6$heterocyclo)C$_0$-C$_4$alkyl-, (heteroaryl)C$_0$-C$_4$alky-.

Preferred R[P1] groups include optionally substituted phenyl, naphthyl, and monocyclic heteroaryl groups, especially those groups (particularly lipophilic groups) which enhance bioavailability of the compounds in the cells of the patient and which exhibit reduced toxicity, enhanced therapeutic index and enhanced pharmacokinetics (the compounds are metabolized and excreted more slowly).

Stabilized Phosphate Prodrugs

Stabilized phosphate prodrugs are moieties that can deliver a mono, di, or triphosphate in vivo. For example, McGuigan has disclosed phosphoramidates in U.S. Pat. Nos. 8,933,053; 8,759,318; 8,658,616; 8,263,575; 8,119,779; 7,951,787 and 7,115,590. Alios has disclosed thiophosphoramidates in U.S. Pat. Nos. 8,895,723 and 8,871,737 incorporated by reference herein. Alios has also disclosed cyclic nucleotides in U.S. Pat. No. 8,772,474 incorporated by reference herein. Idenix has disclosed cyclic phosphoramidates and phosphoramidate/SATE derivatives in WO 2013/177219 incorporated by reference herein. Idenix has also disclosed substituted carbonyloxymethylphosphoramidate compounds in WO 2013/039920 incorporated by reference herein. Hostetler has disclosed lipid phosphate prodrugs, see, for example, U.S. Pat. No. 7,517,858. Hostetler has also disclosed lipid conjugates of phosphonate prodrugs, see, for example, U.S. Pat. Nos. 8,889,658; 8,846,643; 8,710,030; 8,309,565; 8,008,308; and 7,790,703. Emory University has disclosed nucleotide sphingoid and lipid derivatives in WO 2014/124430. RFS Pharma has disclosed purine nucleoside monophosphate prodrugs in WO 2010/091386. Cocrystal Pharma Inc. has also disclosed purine nucleoside monophosphate prodrugs in U.S. Pat. No. 9,173,893 incorporated by reference herein. HepDirect™ technology is disclosed in the article "Design, Synthesis, and Characterization of a Series of Cytochrome P(450) 3A-Activated Prodrugs (HepDirect Prodrugs) Useful for Targeting Phosph(on)ate-Based Drugs to the Liver," (J. Am. Chem. Soc. 126, 5154-5163 (2004). Additional phosphate prodrugs include, but are not limited to phosphate esters, 3',5'-cyclic phosphates including CycloSAL, SATE derivatives (S-acyl-2thioesters) and DTE (dithiodiethyl) prodrugs. For literature reviews that disclose non-limiting examples see: A. Ray and K. Hostetler, "Application of kinase bypass strategies to nucleoside antivirals," Antiviral Research (2011) 277-291; M. Sofia, "Nucleotide prodrugs for HCV therapy," Antiviral Chemistry and Chemotherapy 2011; 22-23-49; and S. Peyrottes et al., "SATE Pronucleotide Approaches: An Overview," Mini Reviews in Medicinal Chemistry 2004, 4, 395. In one embodiment, a 5'-prodrug described in any of these patent filings or literature can be used in the R[5] position of the presented compounds.

In one alternative embodiment, the stabilized phosphate prodrugs, include, but are not limited to those described in U.S. Pat. Nos. 9,173,893 and 8,609,627, incorporated by reference herein, including for processes of preparation. For example, 5'-prodrugs can be represented by the group:

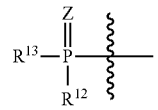

wherein
Z is O or S;
R[12] and R[13], when administered in vivo, are capable of providing the nucleoside monophosphate, diphosphate, or triphosphate. Representative R[12] and R[13] are independently selected from:
(a) OR[14] where R[14] is selected from H, Li, Na, K, phenyl and pyridinyl and wherein phenyl and pyridinyl are optionally substituted with one to three substituents independently selected from the group consisting of (CH$_2$)$_{0-6}$CO$_2$R[17] and (CH$_2$)$_{0-6}$CON(R[17])$_2$;
R[17] is independently H, C$_{1-20}$ alkyl, the carbon chain derived from a fatty alcohol (such as oleyl alcohol, octacosanol, triacontanol, linoleyl alcohol, and etc) or C$_{1-20}$ alkyl substituted with a lower alkyl, alkoxy, di(lower alkyl)-amino, fluoro, C$_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are C$_{1-5}$ alkyl, or C$_{1-5}$ alkyl substituted with a lower alkyl, alkoxy, di(lower alkyl)-amino, fluoro, C$_{3-10}$ cycloalkyl, or cycloalkyl;

(b)

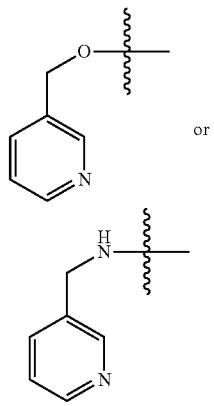

(c) the ester of a D-amino acid or L-amino acid:

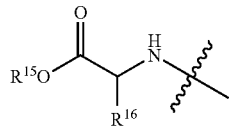

wherein
R$^{16}$ is restricted to those sidechains occurring in natural L-amino acids, and
R$^{15}$ is H, C$_{1-20}$ alkyl, the carbon chain derived from a fatty alcohol (such as oleyl alcohol, octacosanol, triacontanol, linoleyl alcohol, and etc) or C$_{1-20}$ alkyl substituted with a lower alkyl, alkoxy, di(lower alkyl)-amino, fluoro, C$_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are C$_{1-5}$ alkyl, or C$_{1-5}$ alkyl substituted with a lower alkyl, alkoxy, di(lower alkyl)-amino, fluoro, C$_{3-10}$ cycloalkyl, or cycloalkyl;

(d) R$^{12}$ and R$^{13}$ can come together to form a ring:

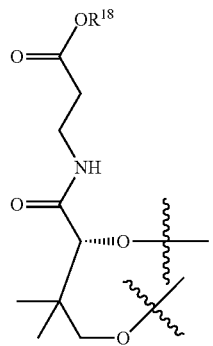

wherein
R$^{18}$ is H, C$_{1-20}$ alkyl, C$_{1-20}$ alkenyl, the carbon chain derived from a fatty alcohol (such as oleyl alcohol, octacosanol, triacontanol, linoleyl alcohol, etc) or C$_{1-20}$ alkyl substituted with a lower alkyl, alkoxy, di(lower alkyl)-amino, fluoro, C$_{3-10}$ cycloalkyl, cycloalkyl alkyl, cycloheteroalkyl, aryl, such as phenyl, heteroaryl, such as, pyridinyl, substituted aryl, or substituted heteroaryl;

wherein the substituents are C$_{1-5}$ alkyl, or C$_{1-5}$ alkyl substituted with a lower alkyl, alkoxy, di(lower alkyl)-amino, fluoro, C$_{3-10}$ cycloalkyl, or cycloalkyl;

(e) R$^{12}$ and R$^{13}$ can come together to form a ring selected from

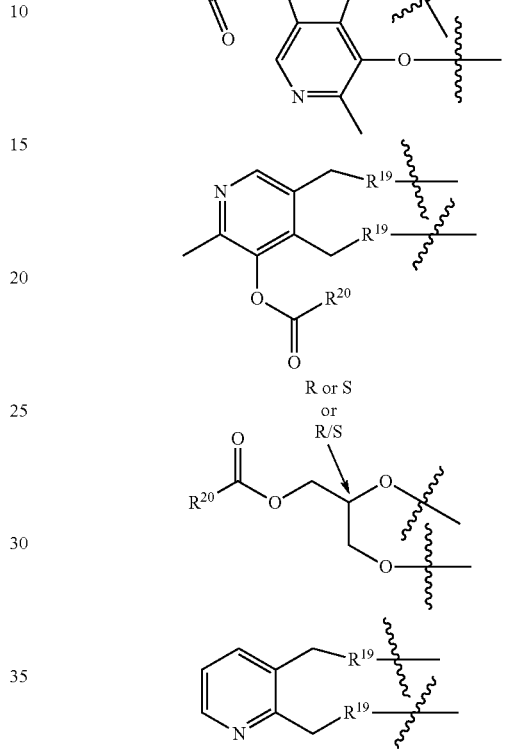

wherein
R$^{19}$ is O or NH; and
R$^{20}$ is selected from H, C$_{1-20}$ alkyl, C$_{1-20}$ alkenyl, the carbon chain derived from a fatty acid (such as oleic acid, linoleic acid, and the like), and C$_{1-20}$ alkyl substituted with a lower alkyl, alkoxy, di(lower alkyl)-amino, fluoro, C$_{3-10}$ cycloalkyl, cycloalkyl alkyl, cycloheteroalkyl, aryl, such as phenyl, heteroaryl, such as pyridinyl, substituted aryl, or substituted heteroaryl; wherein the substituents are C$_{1-5}$ alkyl, or C$_{1-5}$ alkyl substituted with a lower alkyl, alkoxy, di(lower alkyl)-amino, fluoro, C$_{3-10}$ cycloalkyl, or cycloalkyl.

In an alternate embodiment, 3',5'-prodrugs can be represented by:

Formula III'

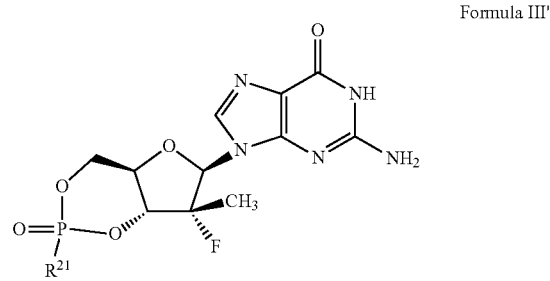

-continued

Formula IV'

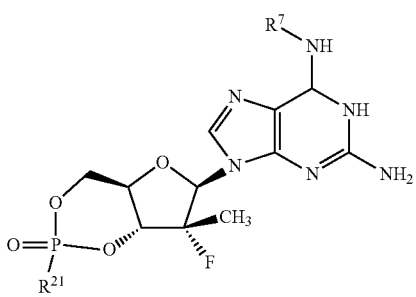

Formula V'

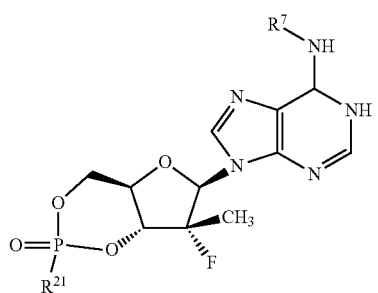

wherein:
when chirality exists at the phosphorous center it may be wholly or partially $R_p$ or $S_p$ or any mixture thereof, and can be enantiomerically enriched;
$R^{21}$ is selected from $OR^{14}$,

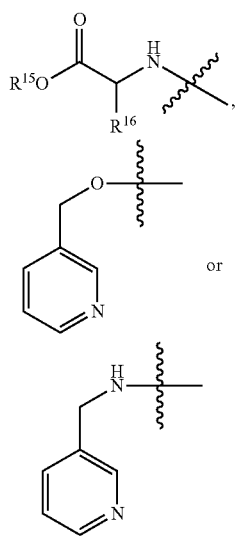

and fatty alcohol derived (for example but not limited to linoleyl-O— and oleyl-O—;
$R^7$ is selected from hydrogen and methyl; and
$R^{14}$, $R^{15}$, and $R^{16}$ are as defined herein.

Isotopic Substitution

The present invention includes the use of an effective amount of a compound of Formula I (including for example Compound 1, 1A or 1B) or Formula II (including for example, Compound 3, 3A, or 3B), Formula III, Formula IV, or Formula V or a pharmaceutically acceptable salt thereof, wherein the compounds have a desired isotopic substitutions of atoms at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2H$) and tritium ($^3H$) may be used anywhere in described structures. Alternatively or in addition, isotopes of carbon, e.g., $^{13}C$ and $^{14}C$, may be used. An example of an isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect). Achillion Pharmaceuticals, Inc. (WO/2014/169278 and WO/2014/169280) describes deuteration of nucleotides to improve their pharmacokinetic or pharmacodynamic, including at the 5-position of the molecule.

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break-down can reduce the rate of or eliminate the metabolism at that bond. At any position of the compound that a hydrogen atom may be present, the hydrogen atom can be any isotope of hydrogen, including protium (H), deuterium ($^2H$) and tritium ($^3H$). Thus, reference herein to a compound encompasses all potential isotopic forms unless the context clearly dictates otherwise.

The term "isotopically-labeled" analog refers to an analog that is a "deuterated analog", a "$^{13}C$-labeled analog," or a "deuterated/$^{13}C$-labeled analog." The term "deuterated analog" means a compound described herein, whereby a H-isotope, i.e., hydrogen/protium ($^1H$), is substituted by a H-isotope, i.e., deuterium ($^2H$). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location. Unless indicated to the contrary, the deuteration is at least 80% at the selected location. Deuteration of the nucleoside can occur at any replaceable hydrogen that provides the desired results.

For example, non-limiting examples of deuterated compounds of Formula I include:

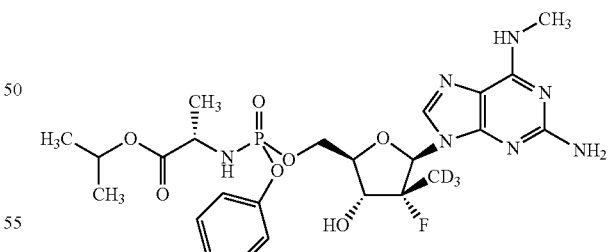

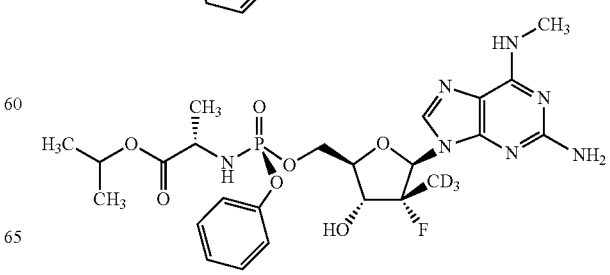

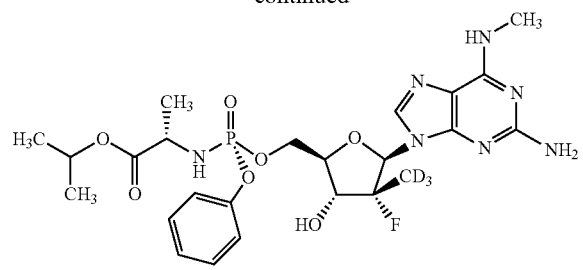
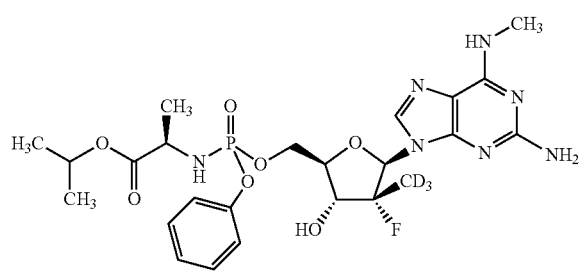
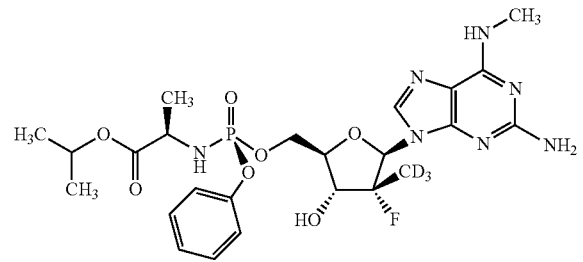
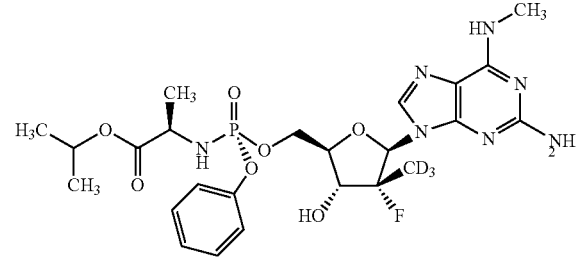
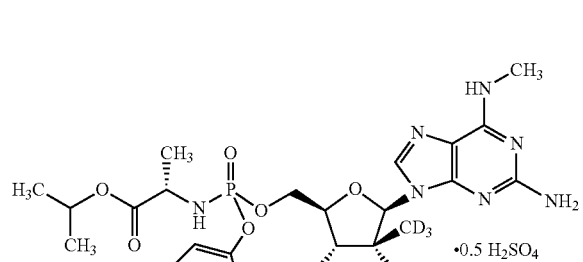
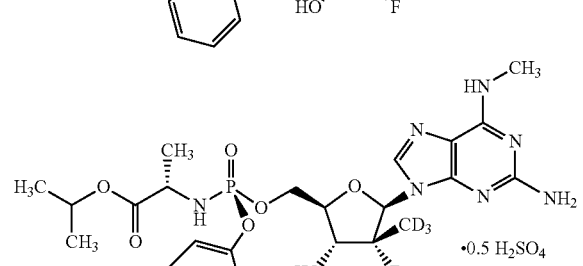
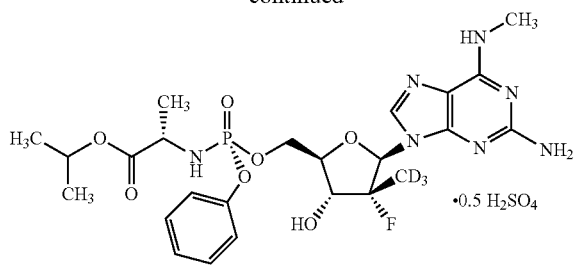
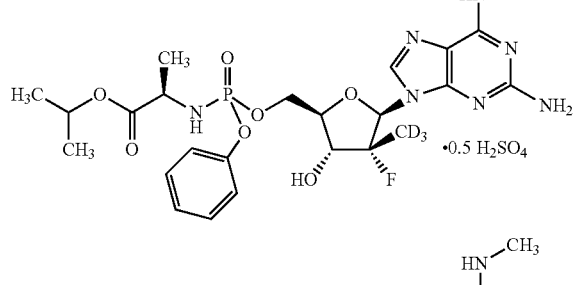
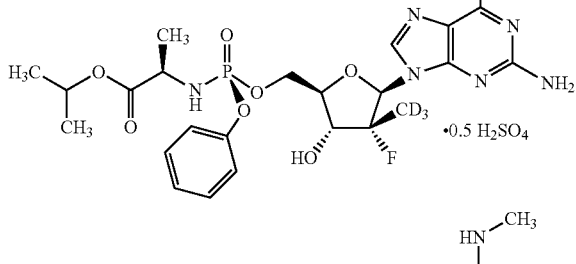
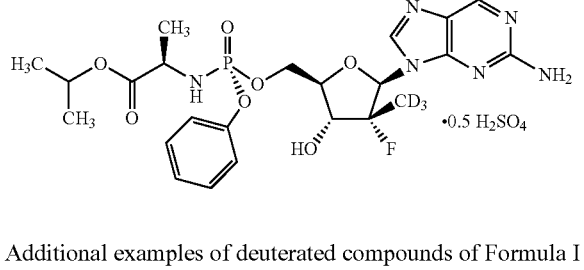
Additional examples of deuterated compounds of Formula I include:
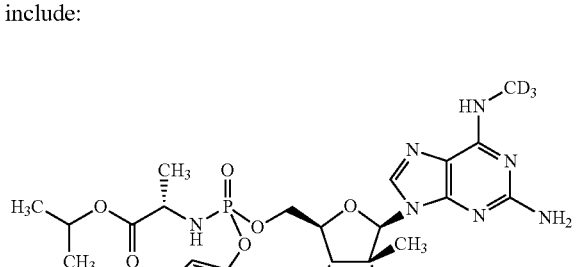
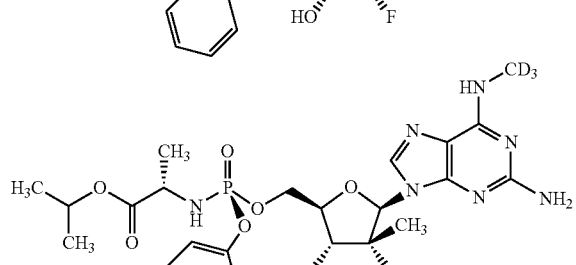

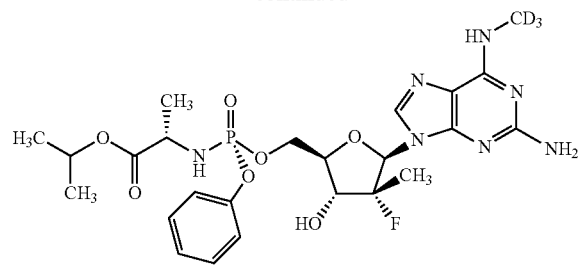

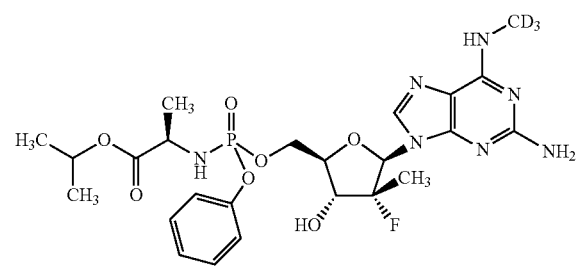

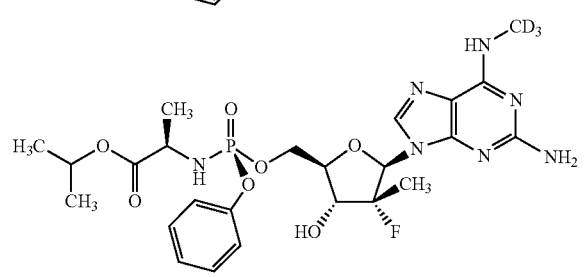

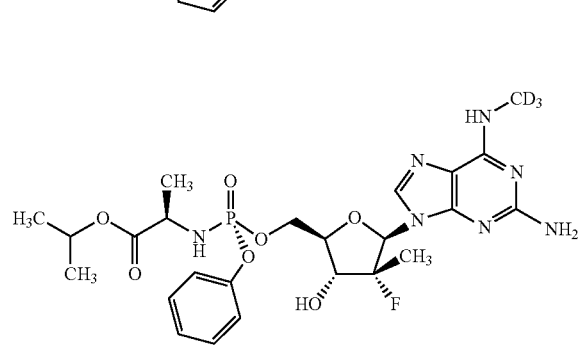

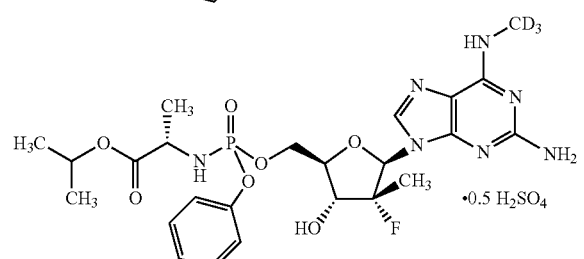

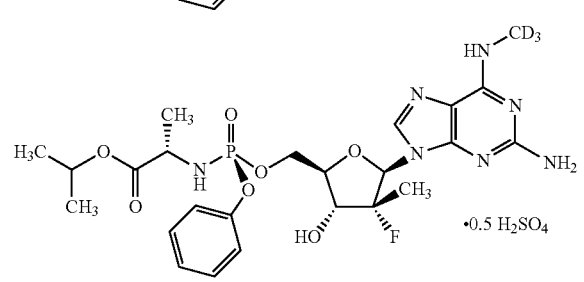

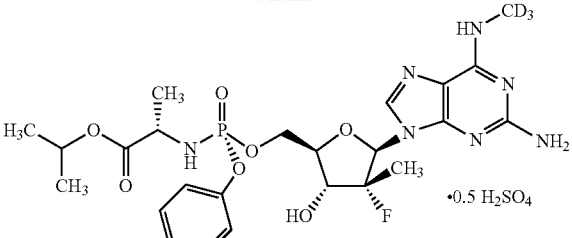

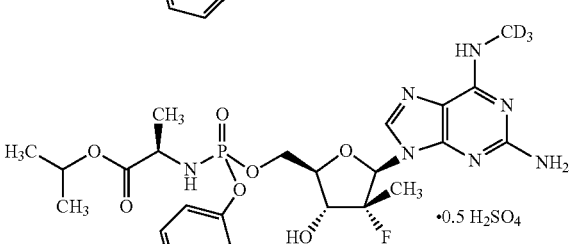

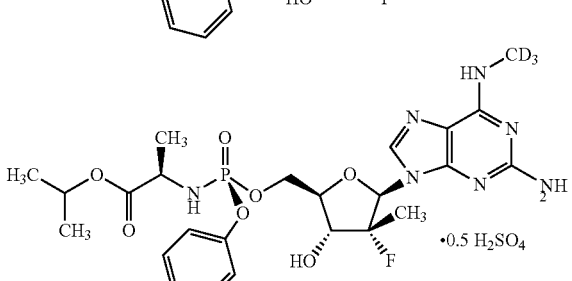

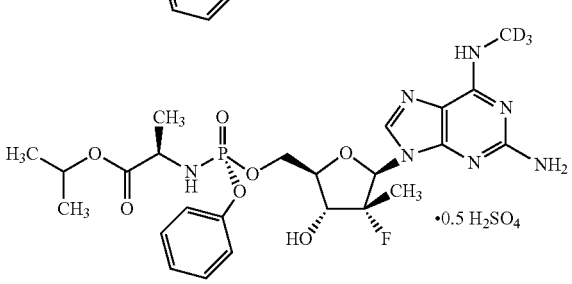

Methods of Treatment or Prophylaxis

Treatment, as used herein, refers to the administration of a compound of Formula I, Formula II, Formula III, Formula IV, or Formula V or a pharmaceutically acceptable salt thereof, in an effective amount to a host, for example a human, that is or may become infected with SARS-CoV-2. In one embodiment the method of treatment comprises administration of an effective amount of Compound 1A or Compound 3A or a pharmaceutically acceptable salt thereof, for example Compound 2A or Compound 4A. In one embodiment the method of treatment comprises administration of an effective amount of Compound 1B or Compound 3B or a pharmaceutically acceptable salt thereof, for example Compound 2B or Compound 4B.

The present invention also includes prophylactic or preventative therapies. In one embodiment, a compound of Formula I, Formula II, Formula III, Formula IV, or Formula V or a pharmaceutically acceptable salt thereof, is administered to a host who has been exposed to and thus is at risk of infection or at risk of reinfection of SARS-CoV-2. Prophylactic treatment may be administered, for example, to a subject not yet exposed to or infected with SARS-CoV-2 but who is susceptible to, or otherwise at risk of exposure or infection with SARS-CoV-2. In one embodiment, a host at risk for infection or reinfection is administered a compound of Formula I, Formula II, Formula III, Formula IV, or Formula V or a pharmaceutically acceptable salt thereof indefinitely until the risk of exposure no longer exists.

In another alternative embodiment, a method to prevent transmission is provided that includes administering an effective amount of one of the compounds described herein to humans for a sufficient length of time prior to exposure to crowds that can be infected, including during travel or public events or meetings, including for example, up to 3, 5, 7, 10, 12, 14 or more days prior to a communicable situation, either because the human is infected or to prevent infection from an infected person in the communicable situation.

In one embodiment, a compound of Formula I, Formula II, Formula III, Formula IV, or Formula V or a pharmaceutically acceptable salt thereof is administered in an effective amount for at least two weeks, three weeks, one month, two months, three months, four months, five months, or six months or more after infection.

The invention is directed to a method of treatment of COVID-19, including drug resistant and multidrug resistant forms of the virus and related disease states, conditions, or complications of the viral infection, including pneumonia, such as 2019 novel coronavirus-infected pneumonia (NCIP), acute lung injury (ALI), and acute respiratory distress syndrome (ARDS). Additional non-limiting complications include hypoxemic respiratory failure, acute respiratory failure (ARF), acute liver injury, acute cardiac injury, acute kidney injury, septic shock, disseminated intravascular coagulation, blood clots, multisystem inflammatory syndrome, chronic fatigue, rhabdomyolysis, and cytokine storm.

The method also comprises administering to a host in need thereof, typically a human, an effective amount of a compound of Formula I, Formula II, Formula III, Formula IV, or Formula V or a pharmaceutically acceptable salt thereof, optionally in combination with at least one additional bioactive agent, for example, an additional anti-viral agent, further optionally in combination with a pharmaceutically acceptable carrier additive and/or excipient.

In one embodiment, the administration of a compound of Formula I, Formula II, Formula III, Formula IV, or Formula V or a pharmaceutically acceptable salt thereof to a patient in need thereof results in a reduction in the incidence of progressive respiratory insufficiency (PRI) as measured by greater than or equal to a 1-tier or even 2-tier or more increase in respiratory support methods required to maintain satisfactory oxygenation ($SpO_2 \geq 93\%$) using the 6-tier hierarchical levels of respiratory support methods described below.

The scale of increasing respiratory support levels includes:

Level 1: Normal oxygenation on room air ($SpO_2 \geq 93\%$), no need for supplemental O2

Level 2: Persistent hypoxemia on room air ($SpO_2 \geq 93$) with requirement for low-level supplemental $O_2$ by nasal cannular or mask (up to 2 L/min) to maintain $SpO_2 \geq 93$ Level 3: Requirement for higher levels of passive supplemental $O_2$ by nasal cannular or mask (up to 2 L/min) to maintain $SpO_2 \geq 93$ Level 4: Requirement for oxygenation by positive-pressure devices, e.g., Continuous Positive Airway Pressure (CPAP) or Bi-level Positive Airway Pressure (BiPAP) or other non-invasive positive-pressure respiratory support methods to main satisfactory oxygenation and/or ventilation Level 5: Requires invasive respiratory support (intubated mechanical ventilation or ECMO)

Level 6: Death

In one embodiment, the reduction in PRI is an increase from level 5 to level 3, level 5 to level 2, or level 5 to level 1. In one embodiment, the reduction in PRI is an increase from level 4 to level 2 or level 4 to level 1. In one embodiment, the reduction in PRI is an increase from level 3 to level 1.

In one embodiment, the administration of a compound of Formula I, Formula II, Formula III, Formula IV, or Formula V or a pharmaceutically acceptable salt thereof reduces the median time to Clinical Recovery (status 6, 7, or 8 in the NIAID Clinical Status scale using an adapted National Institute of Allergy and Infectious Diseases (NIAID) ordinal scale of Clinical Status) by at least 3, 4, 5 or more days. In one embodiment, the administration of a compound of Formula I, Formula II, Formula III, Formula IV, or Formula V or a pharmaceutically acceptable salt thereof results in an improvement as measured by the adapted ordinal scale of Clinical Status.

From most severe disease to progressively less severe disease, the stages of the adapted ordinal scale of overall Clinical Status are defined as follows:
1. Death
2. Hospitalized, on invasive mechanical ventilation or ECMO
3. Hospitalized, on non-invasive ventilation or high flow oxygen devices
4. Hospitalized, requiring supplemental oxygen
5. Hospitalized, not requiring supplemental oxygen—requiring ongoing medical care (COVID-19 related or otherwise)
6. Hospitalized, not requiring supplemental oxygen; no longer requires close medical care for COVID-19
7. Not hospitalized, but with limitation on activities and needing close outpatient care for COVID-19 manifestations
8. Not hospitalized, no limitations on activities, no need for continued close medical care In one embodiment, the administration of a compound of Formula I, Formula II, Formula III, Formula IV, or Formula V or a pharmaceutically acceptable salt thereof reduces the median time to Clinical Recovery (status 6, 7, or 8 in the NIAID Clinical Status scale using an adapted National Institute of Allergy and Infectious Diseases (NIAID) ordinal scale of Clinical Status) by at least 5 days, at least 6 days, at least 7 days, at least 8 days, at least 9 days, or at least 10 days.

In one embodiment, the administration of a compound of Formula I, Formula II, Formula III, Formula IV, or Formula V or a pharmaceutically acceptable salt thereof reduces the duration of hospitalization for a patient infected with COVID-19.

In one embodiment, the administration of a compound of Formula I, Formula II, Formula III, Formula IV, or Formula V or a pharmaceutically acceptable salt thereof reduces the time to sustained non-detectable SARS-CoV-2 virus in the nose and/or throat in a patient infected with COVID-19.

In one embodiment, the administration of a compound of Formula I, Formula II, Formula III, Formula IV, or Formula V or a pharmaceutically acceptable salt thereof reduces respiratory failure or death.

In one embodiment, the administration of a compound of Formula I, Formula II, Formula III, Formula IV, or Formula V or a pharmaceutically acceptable salt thereof reduces the proportion of patients in a hospital population who are SARS-CoV-2 positive after at least about 5, 6, 7, 8, 9, 10, 11, 12, 13, or 14 days of treatment.

Pharmaceutical Compositions and Dosage Forms

A compound of Formula I, Formula II, Formula III, Formula IV, or Formula V or a pharmaceutically acceptable salt thereof, can be administered in an effective amount for the treatment of COVID-19 in a host, typically a human, in need thereof. In one embodiment the compound is Compound 1A or Compound 3A or a pharmaceutically acceptable salt thereof, for example Compound 2A or Compound 4A. In one embodiment the compound is Compound 1B or Compound 3B or a pharmaceutically acceptable salt thereof, for example Compound 2B or Compound 4B.

The compound or its salt can be provided as the neat chemical but is more typically administered as a pharmaceutical composition that includes an effective amount for a host, typically a human, in need of a treatment for COVID-19. Thus, in one embodiment, the disclosure provides pharmaceutical compositions comprising an effective amount of a compound of Formula I, Formula II, Formula III, Formula IV, or Formula V or a pharmaceutically acceptable salt thereof, with at least one pharmaceutically acceptable carrier for the treatment of COVID-19. The pharmaceutical composition may contain a compound of Formula I, Formula II, Formula III, Formula IV, or Formula V or a pharmaceutically acceptable salt thereof, as the only active agent, or, in an alternative embodiment, in combination with at least one additional active agent.

A compound of Formula I (including but not limited to Compound 1, 1A or 1B) or Formula II (including but not limited to Compound 3, 3A or 3B), Formula III, Formula IV, Formula V or a pharmaceutically acceptable salt thereof, can be formulated with one or more pharmaceutically acceptable carriers. Oral dosage forms are sometimes selected due to ease of administration and prospective favorable patient compliance. In one embodiment, a compound of Formula I, Formula II, Formula III, Formula IV, or Formula V or a pharmaceutically acceptable salt thereof, is provided in a solid dosage form, such as a tablet or pill, which are well known in the art and described further below. Enteric coated oral tablets may also be used to enhance bioavailability of the compounds for an oral route of administration.

Pharmaceutical compositions (formulations) may be administered via oral, parenteral, intravenous, inhalation, intramuscular, topical, transdermal, buccal, subcutaneous, suppository, or other route, including intranasal spray routes of delivery. Effective dosage form will depend upon the bioavailability/pharmacokinetic of the particular agent chosen as well as the severity of disease in the patient. A compound of Formula I, Formula II, Formula III, Formula IV, or Formula V or a pharmaceutically acceptable salt thereof, can be administered, for example, in one or more tablets, capsules, injections, intravenous formulations, suspensions, liquids, emulsions, implants, particles, spheres, creams, ointments, suppositories, inhalable forms, transdermal forms, buccal, sublingual, topical, gel, mucosal, and the like.

Intravenous and intramuscular formulations are often administered in sterile saline. One of ordinary skill in the art may modify the formulations to render them more soluble in water or another vehicle, for example, this can be easily accomplished by minor modifications (salt formulation, esterification, etc.).

The pharmaceutical compositions contemplated here optionally include a carrier, as described further below. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Representative carriers include solvents, diluents, pH modifying agents, preservatives, antioxidants, suspending agents, wetting agent, viscosity agents, tonicity agents, stabilizing agents, and combinations thereof. In some embodiments, the carrier is an aqueous carrier.

One or more viscosity agents may be added to the pharmaceutical composition to increase the viscosity of the composition as desired. Examples of useful viscosity agents include, but are not limited to, hyaluronic acid, sodium hyaluronate, carbomers, polyacrylic acid, cellulosic derivatives, polycarbophil, polyvinylpyrrolidone, gelatin, dextin, polysaccharides, polyacrylamide, polyvinyl alcohol (including partially hydrolyzed polyvinyl acetate), polyvinyl acetate, derivatives thereof and mixtures thereof.

Solutions, suspensions, or emulsions for administration may be buffered with an effective amount of buffer necessary to maintain a pH suitable for the selected administration. Suitable buffers are well known by those skilled in the art. Some examples of useful buffers are acetate, borate, carbonate, citrate, and phosphate buffers.

To prepare the pharmaceutical compositions according to the present invention, a therapeutically effective amount of a compound of Formula I, Formula II, Formula III, Formula IV, or Formula V or a pharmaceutically acceptable salt thereof may be admixed with a pharmaceutically acceptable carrier according to conventional pharmaceutical compounding techniques to produce a dose. A carrier may take a wide variety of forms depending on the form of preparation desired for administration, e.g., oral or parenteral.

In preparing pharmaceutical compositions in oral dosage form, any of the usual pharmaceutical media may be used. Thus, for liquid oral preparations such as suspensions, elixirs, and solutions, suitable carriers and additives including water, glycols, oils, alcohols, flavoring agents, preservatives, coloring agents, and the like may be used. For solid oral preparations such as powders, tablets, capsules, and for solid preparations such as suppositories, suitable carriers and additives including starches, sugar carriers, such as dextrose, mannitol, lactose, and related carriers, diluents, granulating agents, lubricants, binders, disintegrating agents, and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

Amounts and weights mentioned in this disclosure typically refer to the free form (i.e., non-salt, hydrate or solvate form). The typically values described herein represent free-form equivalents, i.e., quantities as if the free form would be administered. If salts are administered the amounts need to be calculated in function of the molecular weight ratio between the salt and the free form.

The amount of a compound of Formula I, Formula II, Formula III, Formula IV, or Formula V or a pharmaceutically acceptable salt thereof, in the pharmaceutically acceptable formulation according to the present invention is an effective amount to achieve the desired outcome of treating COVID-19, reducing the likelihood of COVID-19, or the inhibition, reduction, and/or elimination of COVID-19 or its secondary effects, including disease states, conditions, and/or complications which occur secondary to the virus. As non-limiting embodiments, a therapeutically effective amount of the present compounds in a pharmaceutical dosage form may range, for example, from about 0.001 mg/kg to about 100 mg/kg per day or more. A compound of Formula I, Formula II, Formula III, Formula IV, or Formula V or a pharmaceutically acceptable salt thereof, may for example in non-limiting embodiments be administered in amounts ranging from about 0.1 mg/kg to about 15 mg/kg per day of the patient, depending upon the pharmacokinetics of the agent in the patient.

The weight of active compound in the dosage form described herein is with respect to either the free form or the salt form of the compound unless otherwise specifically indicated. For example, approximately 600 mg of Compound 2 is the equivalent of approximately 550 mg of Compound 1.

In certain embodiments, the pharmaceutical composition is in a dosage form that contains from about 1 mg to about 2000 mg, from about 10 mg to about 1000 mg, from about 100 mg to about 800 mg, from about 200 mg to about 600 mg, from about 300 mg to about 500 mg, or from about 400 mg to about 450 mg of a compound of Formula I, Formula II, Formula III, Formula IV, or Formula V or a pharmaceutically acceptable salt thereof, in a unit dosage form.

In certain embodiments, the pharmaceutical composition is in a dosage form, for example in a solid dosage form, that contains up to about 10, about 50, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg or more of a compound of Formula I, Formula II, Formula III, Formula IV, or Formula V or a pharmaceutically acceptable salt thereof, in a unit dosage form.

In certain embodiments, a compound of Formula I, Formula II, Formula III, Formula IV, or Formula V or a pharmaceutically acceptable salt thereof, for example Compound 1 or Compound 2, is administered at an initial dose (or loading dose) followed by a maintenance dose of at least about 300 mg, at least about 350 mg, at least about 400 mg, at least about 450 mg, at least about 500 mg, at least about 550 mg, at least about 650, or at least about 750 and the dose is taken once or twice in a day. In one embodiment, the loading dose is about 1.5 times greater, about 2 times greater, about 2.5 times greater, or 3-fold times greater than the maintenance dose. In one embodiment, the loading dose is administered once, twice, three, four, or more times before the first maintenance dose.

In one embodiment, the pharmaceutical composition is in a dosage form, for example in a solid dosage form, that contains at least 500 mg, at least 550 mg, 600 mg, at least 700 mg, at least 800 mg, at least 900 mg, at least 1000 mg, at least 1100 mg, at least 1200, at least 1300 mg, at least 1400 mg, or at least 1500 mg of a compound of Formula I, Formula II, Formula III, Formula IV, or Formula V or a pharmaceutically acceptable salt thereof, in a unit dosage form.

In certain embodiments, the pharmaceutical composition, for example, a solid dosage form, contains at least about 450 mg, 550 mg, 650 mg, 750 mg or 850 mg of Compound 1 or Compound 3. In one embodiment, the pharmaceutical composition contains at least about 500 mg, at least about 550 mg, or at least about 600 mg of Compound 1 or Compound 3 and the composition is administered twice a day. In one embodiment, the pharmaceutical composition contains at least about 550 mg of Compound 1 and the pharmaceutical composition is administered twice a day. In one embodiment, the pharmaceutical composition is administered at an initial dose (or loading dose) of at least about 900 mg, 1000 mg, 1100 mg, 1100 mg, or 1200 mg of Compound 1 followed by a dose of at least about 400 mg, at least about 450 mg, at least about 500 mg, at least about 550, at least about 600 mg, or at least about 650 mg of Compound 1 twice a day. In one embodiment, the pharmaceutical composition is administered at an initial dose (or loading dose) of at least about 1100 mg of Compound 1 followed by a dose of at least about 450 mg, 550 mg, 650 mg, 750 mg, or 850 mg of Compound 1 twice a day. In one embodiment, the pharmaceutical composition is administered at an initial dose (or loading dose) of at least about 1100 mg of Compound 1 followed by a dose of at least about 550 mg of Compound 1 twice a day. In one embodiment, the maintenance dose is administered for at about 4, 5, 6, 7, 8, 9, 10, or more days. In one embodiment, Compound 1 is Compound 1A. In one embodiment, Compound 1 is Compound 1B.

In certain embodiments, the pharmaceutical composition, for example, a solid dosage form, contains at least about 400 mg, at least about 500 mg, 600 mg, 700 mg, or 800 mg of Compound 2 or Compound 4. In one embodiment, the pharmaceutical composition contains at least about 500 mg, at least about 600 mg, or at least about 700 mg of Compound 2 or Compound 4 and the composition is administered twice a day. In one embodiment, the pharmaceutical composition contains at least about 600 mg of Compound 2 and the pharmaceutical composition is administered twice a day. In one embodiment, the pharmaceutical composition is administered at an initial dose (or loading dose) of at least about 900 mg, 1000 mg, 1100 mg, 1200 mg, or 1300 mg of Compound 2 followed by a dose of at least about 400 mg, 500 mg, 600 mg, 700 mg, or 800 mg of Compound 2 once, twice, or three times a day. In one embodiment, the pharmaceutical composition is administered at an initial dose (or loading dose) of at least about 1000 mg, 1200 mg, or 1400 mg of Compound 2 followed by a dose of at least about 600 mg of Compound 2 twice a day. In one embodiment, the pharmaceutical composition is administered at an initial dose (or loading dose) of at least about 1200 mg of Compound 2 followed by a dose of at least about 400 mg, 500 mg, 600 mg, 700 mg, or 800 mg of Compound 2 twice a day. In one embodiment, the pharmaceutical composition is administered at an initial dose (or loading dose) of at least about 1200 mg of Compound 2 followed by a dose of at least about 600 mg of Compound 2 twice a day. In one embodiment, the maintenance dose is administered for at about 4, 5, 6, 7, 8, 9, 10, or more days. In one embodiment, Compound 2 is Compound 2A. In one embodiment, Compound 2 is Compound 1B.

In one embodiment, an effective amount of Compound 1:

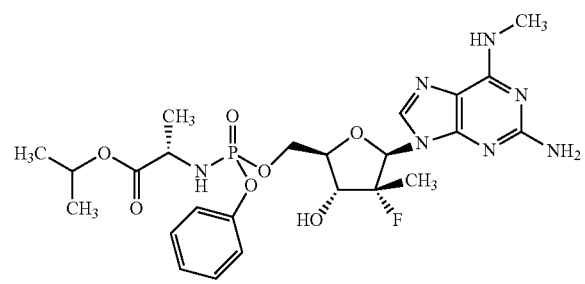 [SMILES: CNc1nc(N)nc2c1ncn2[C@@H]1O[C@H](COP(=O)(N[C@@H](C)C(=O)OC(C)C)Oc2ccccc2)[C@@H](O)[C@@]1(C)F]

or a pharmaceutically acceptable salt thereof, optionally in a pharmaceutically acceptable carrier, is administered for the treatment of the 2019 coronavirus disease (COVID-19) caused by the SARS-CoV-2 virus in a human in need thereof wherein the compound is administered according to the following schedule:

(i) a single loading dose of 1100 mg of free base in one day; followed by (ii) a maintenance dose of 550 mg of free base per day.

In one embodiment, an effective amount of Compound 1A:

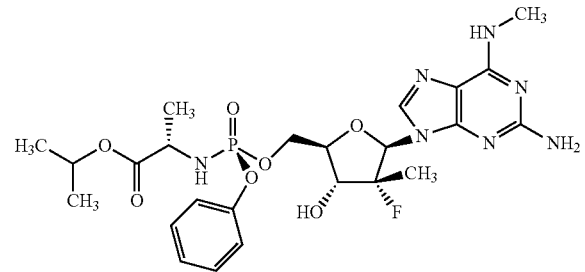 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

or a pharmaceutically acceptable salt thereof, optionally in a pharmaceutically acceptable carrier, is administered for the treatment of the 2019 coronavirus disease (COVID-19) caused by the SARS-CoV-2 virus in a human in need thereof wherein the compound is administered according to the following schedule:

(iii) a single loading dose of 1100 mg of free base in one day; followed by (iv) a maintenance dose of 550 mg of free base per day.

In one embodiment, an effective amount of Compound 2A:

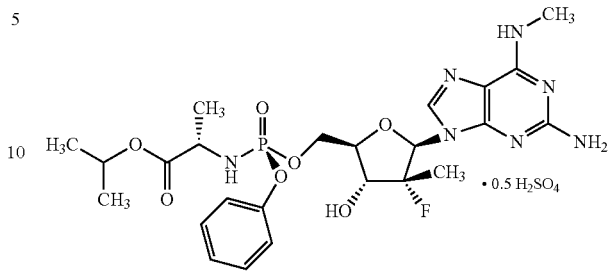

optionally in a pharmaceutically acceptable carrier, is administered for the treatment of the 2019 coronavirus disease (COVID-19) caused by the SARS-CoV-2 virus in a human in need thereof wherein the compound is administered according to the following schedule:

(i) a single loading dose of 1200 mg of salt in one day; followed by (ii) a maintenance dose of 600 mg of salt per day.

In certain embodiments, a compound of Formula I, Formula II, Formula III, Formula IV, or Formula V or a pharmaceutically acceptable salt thereof, is administered for at least five days, six days, seven days, eight days, nine days, ten days, two weeks, three weeks, one month, at least two months, at least three months, at least four months, at least five months, at least six months or more. In one embodiment, a compound of Formula I, Formula II, Formula III, Formula IV, or Formula V or a pharmaceutically acceptable salt thereof, is administered once, twice, three, or more times a day. In one embodiment, it is administered orally twice a day.

For purposes of the present invention, a prophylactically or preventive effective amount of the compositions according to the present invention may generally fall within the ranges set out above, and can be determined in the best judgement of the health care provider. In one embodiment, a compound of the present invention is administered seasonally as the risk of the virus increases to prevent infection, or can be administered, for example, before, during and/or after travel or exposure.

One of ordinary skill in the art will recognize that a therapeutically effective amount will vary with the infection or condition to be treated, its severity, the treatment regimen to be employed, the pharmacokinetic of the agent used, as well as the patient or subject (animal or human) to be treated, and such therapeutic amount can be determined by the attending physician or specialist.

Solid Dosage Forms

An aspect of the invention is a solid dosage form that includes an effective amount of a compound of Formula I (including but not limited to Compound 1, 1A, 1B, 2, 2A or 2B) or Formula II (including but not limited to Compound 3), Formula III, Formula IV, Formula V or a pharmaceutically acceptable salt thereof, optionally in a pharmaceutically acceptable carrier.

In one embodiment, the solid dosage form includes a spray dried solid dispersion of a compound of Formula I, Formula II, Formula III, Formula IV, or Formula V or a pharmaceutically acceptable salt thereof, and the composition is suitable for oral delivery. In another embodiment, the solid dosage form is a granulo layered solid dispersion of a compound of Formula I, Formula II, Formula III, Formula IV, or Formula V or a pharmaceutically acceptable salt thereof, and the composition is suitable for oral delivery.

In other embodiments, the solid dispersion also contains at least one excipient selected from copovidone, poloxamer and HPMC-AS. In one embodiment the poloxamer is Poloxamer 407 or a mixture of poloxamers that may include Poloxamer 407. In one embodiment HPMC-AS is HPMC-AS-L.

In other embodiments, a solid dosage form prepared from a compound of Formula I, Formula II, Formula III, Formula IV, or Formula V or a pharmaceutically acceptable salt thereof, also comprises one or more of the following excipients: a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol) 5000-phosphatidylethanolamine; poly(ethylene glycol) 400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, silicified microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g., poly(1,3-dioxan-2one)), polyanhydride (e.g., poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g., poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), or hydroxypropylmethyl cellulose acetate succinate (HPMCAS).

In other embodiments, a solid dosage form prepared from a compound of Formula I, Formula II, Formula III, Formula IV, or Formula V or a pharmaceutically acceptable salt thereof, also comprises one or more of the following surfactants: polyoxyethylene glycol, polyoxypropylene glycol, decyl glucoside, lauryl glucoside, octyl glucoside, polyoxyethylene glycol octylphenol, Triton X-100, glycerol alkyl ester, glyceryl laurate, cocamide MEA, cocamide DEA, dodecyldimethylamine oxide, and poloxamers. Examples of poloxamers include, poloxamers 188, 237, 338 and 407. These poloxamers are available under the trade name Pluronic® (available from BASF, Mount Olive, N.J.) and correspond to Pluronic® F-68, F-87, F-108 and F-127, respectively. Poloxamer 188 (corresponding to Pluronic® F-68) is a block copolymer with an average molecular mass of about 7,000 to about 10,000 Da, or about 8,000 to about 9,000 Da, or about 8,400 Da. Poloxamer 237 (corresponding to Pluronic® F-87) is a block copolymer with an average molecular mass of about 6,000 to about 9,000 Da, or about 6,500 to about 8,000 Da, or about 7,700 Da. Poloxamer 338 (corresponding to Pluronic® F-108) is a block copolymer with an average molecular mass of about 12,000 to about 18,000 Da, or about 13,000 to about 15,000 Da, or about 14,600 Da. Poloxamer 407 (corresponding to Pluronic® F-127) is a polyoxyethylene-polyoxypropylene triblock copolymer in a ratio of between about E101 P56 E101 to about E106 P70 E106, or about E101 P56E101, or about E106 P70 E106, with an average molecular mass of about 10,000 to about 15,000 Da, or about 12,000 to about 14,000 Da, or about 12,000 to about 13,000 Da, or about 12,600 Da.

In yet other embodiments, a solid dosage form prepared from a compound of Formula I, Formula II, Formula III, Formula IV, or Formula V or a pharmaceutically acceptable salt thereof, also comprises one or more of the following surfactants: polyvinyl acetate, cholic acid sodium salt, dioctyl sulfosuccinate sodium, hexadecyltrimethyl ammonium bromide, saponin, sugar esters, Triton X series, sorbitan trioleate, sorbitan mono-oleate, polyoxyethylene (20) sorbitan monolaurate, polyoxyethylene (20) sorbitan monooleate, oleyl polyoxyethylene (2) ether, stearyl polyoxyethylene (2) ether, lauryl polyoxyethylene (4) ether, block copolymers of oxyethylene and oxypropylene, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, cetylpyridinium chloride, benzalkonium chloride, olive oil, glyceryl monolaurate, corn oil, cotton seed oil, and sunflower seed oil.

In alternative embodiments, a solid dosage form prepared from a compound of Formula I, Formula II, Formula III, Formula IV, or Formula V or a pharmaceutically acceptable salt thereof, is prepared by a process that includes solvent or dry granulation optionally followed by compression or compaction, spray drying, nano-suspension processing, hot melt extrusion, extrusion/spheronization, molding, spheronization, layering (e.g., spray layering suspension or solution), or the like. Examples of such techniques include direct compression, using appropriate punches and dies, for example wherein the punches and dies are fitted to a suitable tableting press; wet granulation using suitable granulating equipment such as a high shear granulator to form wetted particles to be dried into granules; granulation followed by compression using appropriate punches and dies, wherein the punches and dies are fitted to a suitable tableting press; extrusion of a wet mass to form a cylindrical extrudate to be cut into desire lengths or break into lengths under gravity and attrition; extrusion/spheronization where the extrudate is rounded into spherical particles and densified by spheronization; spray layering of a suspension or solution onto an inert core using a technique such as a convention pan or Wurster column; injection or compression molding using suitable molds fitted to a compression unit; and the like.

Exemplary disintegrants include alginic acid, carboxymethylcellulose calcium, carboxymethylcellulose sodium, cross-linked sodium carboxymethylcellulose (sodium croscarmellose), powdered cellulose, chitosan, croscarmellose sodium, crospovidone, guar gum, low substituted hydroxypropyl cellulose, methyl cellulose, microcrystalline cellulose, sodium alginate, sodium starch glycolate, partially pregelatinized starch, pregelatinized starch, starch, sodium carboxymethyl starch, and the like, or a combination thereof.

Exemplary lubricants include calcium stearate, magnesium stearate, glyceryl behenate, glyceryl palmitostearate, hydrogenated castor oil, light mineral oil, sodium lauryl sulfate, magnesium lauryl sulfate, sodium stearyl fumarate, stearic acid, zinc stearate, silicon dioxide, colloidal silicon dioxide, dimethyldichlorosilane treated with silica, talc, or a combination thereof.

The dosage form cores described herein may be coated to result in coated tablets. The dosage from cores can be coated with a functional or non-functional coating, or a combination of functional and non-functional coatings. "Functional coating" includes tablet coatings that modify the release properties of the total composition, for example, a sustained-release or delayed-release coating. "Non-functional coating" includes a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition. A non-functional coating can also mask the taste of the uncoated composition including the active pharmaceutical ingredient. A coating may comprise a light blocking material, a light absorbing material, or a light blocking material and a light absorbing material.

Exemplary polymethacrylates include copolymers of acrylic and methacrylic acid esters, such as a. an aminomethacrylate copolymer USP/NF such as a poly(butyl methacrylate, (2-dimethyl aminoethyl)methacrylate, methyl methacrylate) 1:2:1 (e.g., EUDRAGIT E 100, EUDRAGIT EPO, and EUDRAGIT E 12.5; CAS No. 24938-16-7); b. a poly(methacrylic acid, ethyl acrylate) 1:1 (e.g., EUDRAGIT L30 D-55, EUDRAGIT L100-55, EASTACRYL 30D, KOLLICOAT MAE 30D AND 30DP; CAS No. 25212-88-8); c. a poly(methacrylic acid, methyl methacrylate) 1:1 (e.g., EUDRAGIT L 100, EUDRAGIT L 12.5 and 12.5 P; also known as methacrylic acid copolymer, type ANF; CAS No. 25806-15-1); d. a poly(methacrylic acid, methyl methacrylate) 1:2 (e.g., EUDRAGIT S 100, EUDRAGIT S 12.5 and 12.5P; CAS No. 25086-15-1); e. a poly(methyl acrylate, methyl methacrylate, methacrylic acid) 7:3:1 (e.g., Eudragit FS 30 D; CAS No. 26936-24-3); f. a poly(ethyl acrylate, methylmethacrylate, trimethylammonioethyl methacrylate chloride) 1:2:0.2 or 1:2:0.1 (e.g., EUDRAGITS RL 100, RL PO, RL 30 D, RL 12.5, RS 100, RS PO, RS 30 D, or RS 12.5; CAS No. 33434-24-1); g. a poly(ethyl acrylate, methyl methacrylate) 2:1 (e.g., EUDRAGIT NE 30 D, Eudragit NE 40D, Eudragit NM 30D; CAS No. 9010-88-2); and the like, or a combination thereof.

Suitable alkylcelluloses include, for example, methylcellulose, ethylcellulose, and the like, or a combination thereof. Exemplary water based ethylcellulose coatings include AQUACOAT, a 30% dispersion further containing sodium lauryl sulfate and cetyl alcohol, available from FMC, Philadelphia, PA; SURELEASE a 25% dispersion further containing a stabilizer or other coating component (e.g., ammonium oleate, dibutyl sebacate, colloidal anhydrous silica, medium chain triglycerides, etc.) available from Colorcon, West Point, PA; ethyl cellulose available from Aqualon or Dow Chemical Co (Ethocel), Midland, MI. Those skilled in the art will appreciate that other cellulosic polymers, including other alkyl cellulosic polymers, can be substituted for part or all of the ethylcellulose.

Other suitable materials that can be used to prepare a functional coating include hydroxypropyl methylcellulose acetate succinate (HPMCAS); cellulose acetate phthalate (CAP); a polyvinylacetate phthalate; neutral or synthetic waxes, fatty alcohols (such as lauryl, myristyl, stearyl, cetyl or specifically cetostearyl alcohol), fatty acids, including fatty acid esters, fatty acid glycerides (mono-, di-, and tri-glycerides), hydrogenated fats, hydrocarbons, normal waxes, stearic acid, stearyl alcohol, hydrophobic and hydrophilic materials having hydrocarbon backbones, or a combination thereof. Suitable waxes include beeswax, glycowax, castor wax, carnauba wax, microcrystalline wax, candelilla, and wax-like substances, e.g., material normally solid at room temperature and having a melting point of from about 30° C. to about 100° C., or a combination thereof.

In other embodiments, a functional coating may include digestible, long chain (e.g., C8-C50, specifically C12-C40), substituted or unsubstituted hydrocarbons, such as fatty acids, fatty alcohols, glyceryl esters of fatty acids, mineral and vegetable oils, waxes, or a combination thereof. Hydrocarbons having a melting point of between about 25° C. and about 90° C. may be used. Specifically, long chain hydrocarbon materials, fatty (aliphatic) alcohols can be used.

The coatings can optionally contain additional pharmaceutically acceptable excipients such as a plasticizer, a stabilizer, a water-soluble component (e.g., pore formers), an anti-tacking agent (e.g., talc), a surfactant, and the like, or a combination thereof.

A functional coating may include a release-modifying agent, which affects the release properties of the functional coating. The release-modifying agent can, for example, function as a pore-former or a matrix disrupter. The release-modifying agent can be organic or inorganic, and include materials that can be dissolved, extracted or leached from the coating in the environment of use. The release-modifying agent can comprise one or more hydrophilic polymers including cellulose ethers and other cellulosics, such as hydroxypropyl methylcellulose, hydroxypropylcellulose, hydroxyethylcellulose, methyl cellulose, cellulose acetate phthalate, or hydroxypropyl methylcellulose acetate phthalate; povidone; polyvinyl alcohol; an acrylic polymer, such as gastric soluble Eudragit FS 30D, pH sensitive Eudragit L30D 55, L 100, S 100, or L 100-55; or a combination thereof. Other exemplary release-modifying agents include a povidone; a saccharide (e.g., lactose, and the like); a metal stearate; an inorganic salt (e.g., dibasic calcium phosphate, sodium chloride, and the like); a polyethylene glycol (e.g., polyethylene glycol (PEG) 1450, and the like); a sugar alcohol (e.g., sorbitol, mannitol, and the like); an alkali alkyl sulfate (e.g., sodium lauryl sulfate); a polyoxyethylene sorbitan fatty acid ester (e.g., polysorbate); or a combination thereof. Exemplary matrix disrupters include water insoluble organic or inorganic material. Organic polymers including but not limited to cellulose, cellulose ethers such as ethylcellulose, cellulose esters such as cellulose acetate, cellulose acetate butyrate and cellulose acetate propionate; and starch can function as matrix disrupters. Examples or inorganic disrupters include many calcium salts such as mono-, di- and tri calcium phosphate; silica and, talc.

The coating may optionally contain a plasticizer to improve the physical properties of the coating. For example, because ethylcellulose has a relatively high glass transition temperature and does not form flexible films under normal coating conditions, it may be advantageous to add plasticizer to the ethylcellulose before using the same as a coating material. Generally, the amount of plasticizer included in a coating solution is based on the concentration of the polymer, e.g., can be from about 1% to about 200% depending on the polymer but is most often from about 1 wt % to about 100 wt % of the polymer. Concentrations of the plasticizer, however, can be determined by routine experimentation.

Examples of plasticizers for ethylcellulose and other celluloses include plasticizers such as dibutyl sebacate, diethyl phthalate, triethyl citrate, tributyl citrate, triacetin, or a combination thereof, although it is possible that other water-insoluble plasticizers (such as acetylated monoglycerides, phthalate esters, castor oil, etc.) can be used.

Examples of plasticizers for acrylic polymers include citric acid esters such as triethyl citrate NF, tributyl citrate, dibutyl phthalate, 1,2-propylene glycol, polyethylene glycols, propylene glycol, diethyl phthalate, castor oil, triacetin, or a combination thereof, although it is possible that other plasticizers (such as acetylated monoglycerides, phthalate esters, castor oil, etc.) can be used.

Suitable methods can be used to apply the coating material to the surface of the dosage form cores. Processes such as simple or complex coacervation, interfacial polymerization, liquid drying, thermal and ionic gelation, spray drying, spray chilling, fluidized bed coating, pan coating, or electrostatic deposition may be used.

In certain embodiments, an optional intermediate coating is used between the dosage form core and an exterior coating. Such an intermediate coating can be used to protect the active agent or other component of the core subunit from the material used in the exterior coating or to provide other properties. Exemplary intermediate coatings typically include water-soluble film forming polymers. Such intermediate coatings may include film forming polymers such as hydroxyethyl cellulose, hydroxypropyl cellulose, gelatin, hydroxypropyl methylcellulose, polyethylene glycol, polyethylene oxide, and the like, or a combination thereof; and a plasticizer. Plasticizers can be used to reduce brittleness and increase tensile strength and elasticity. Exemplary plasticizers include polyethylene glycol propylene glycol and glycerin.

Combination and Alternation Therapy

The compounds or their pharmaceutically acceptable salts as described herein can be administered on top of the current standard of care for COVID patients, or in combination or alternation with any other compound or therapy that the healthcare provider deems beneficial for the patient. The combination and/or alternation therapy can be therapeutic, adjunctive, or palliative.

It has been observed that COVID patients can pass through various stages of disease, and that the standard of care can differ based on what stage of illness the patient presents with or advances to. COVID is noteworthy for the development of "cross-talk" between the immune system and the coagulation system. As the disease progresses, the patient can mount an overreaction by the immune system, which can lead to a number of serious implications, including a cytokine storm. Via the cross-talk between the immune system and the coagulation system, the patient can begin clotting in various areas of the body, including the respiratory system, brain, heart and other organs. Multiple clots throughout the body have been observed in COVID patients, requiring anticoagulant therapy. It is considered that these clots may cause long term, or even permanent damage if not treated and disease alleviated.

More specifically, COVID-19 has been described as progressing through three general stages of illness: stage 1 (early infection), stage 2 (pulmonary phase), and stage 3 (hyperinflammation phase/cytokine storm).

Stage 1 is characterized by non-specific, and often mild, symptoms. Viral replication is occurring, and it is appropriate to begin immediate treatment with the compounds described herein and perhaps in combination or alternation with another anti-viral therapy. Interferon-β may also be administered to augment the innate immune response to the virus. In one embodiment, therefore, a compound of Formula I, Formula II, Formula III, Formula IV, or Formula V or a pharmaceutically acceptable salt thereof is used in an effective amount in combination or alternation with interferon-β and or an additional anti-viral drug. Zinc supplements and or Vitamin C is also sometimes administered at this stage or as the illness progresses.

Stage 2 of COVID-19 is the pulmonary phase where patients may experience acute hypoxemic respiratory failure. In fact, the primary organ failure of COVID-19 is hypoxemic respiratory failure. It has been shown that moderate immunosuppression via a steroid, for example, dexamethasone, can be beneficial to patients with acute hypoxemic respiratory failure and/or patients on mechanical ventilation. In one embodiment, a compound of Formula I, Formula II, Formula III, Formula IV, or Formula V or a pharmaceutically acceptable salt thereof is used in an effective amount in combination with a corticosteroid which may be a glucocorticoid. Non-limiting examples are budesonide (Entocort EC), bethamethasone, (Celestone), prednisone (Prednisone Intensol), prednisolone (Orapred, Prelone), triamcinolone (Aristospan Intra-Articular, Aristospan Intralesional, Kenalog), methylprednisolone (Medrol, Depo-Medrol, Solu-Medrol), hydrocortisone, or dexamethasone (Dexamethasone Intensol, DexPak 10 Day, DexPak 13 Day, DexPak 6 Day).

The NS5B inhibitor Remdesivir has provided mixed results when given to COVID19 patients. It can only be administered in a hospital setting, and only by intravenous injection, typically three times a day, which makes it inappropriate for mild to moderate COVID19 patients. In one embodiment, a compound of Formula I, Formula II, Formula III, Formula IV, or Formula V or a pharmaceutically acceptable salt thereof, is administered in combination or in alternation with Remdesivir to amplify the overall antiviral effect.

Stage 3, the final stage of the disease, is characterized by progressive disseminated intravascular coagulation (DIC), a condition in which small blood clots develop throughout the bloodstream. This stage also can include multi-organ failure (e.g. vasodilatory shock, myocarditis). It has also been observed that many patients respond to this severe stage of COVID-19 infection with a "cytokine storm." There does appear to be a bi-directional, synergistic relationship between DIC and cytokine storm. To combat DIC, patients are often administered an anti-coagulant agent, which may, for example, be an indirect thrombin inhibitor or a direct oral anticoagulant ("DOAC"). Non-limiting examples are low-molecular weight heparin, warfarin, bivalirudin (Angiomax), rivaroxaban (Xarelto), dabigatran (Pradaxa), apixaban (Eliquis), or edoxaban (Lixiana). In one embodiment, a compound of Formula I, Formula II, Formula III, Formula IV, or Formula V or a pharmaceutically acceptable salt thereof, is administered in combination or in alternation with anti-coagulant therapy. In some severe cases of clotting in COVID patients, TPA can be administered (tissue plasminogen activator).

It has been observed that high levels of the cytokine interleukin-6 (IL-6) are a precursor to respiratory failure and death in COVID-19 patients. To treat this surge of an immune response, which may constitute a cytokine storm, patients can be administered an IL-6-targeting monoclonal antibody, pharmaceutical inhibitor or protein degrader such as a bispecific compound that binds to IL-6 and also to a protein that mediates degradation. Examples of antibodies include tocilizumab, sarilumab, siltuximab, olokizumab and clazakizumab. In one embodiment, a compound of Formula I, Formula II, Formula III, Formula IV, or Formula V or a pharmaceutically acceptable salt thereof, is administered in combination or in alternation with tocilizumab or sarilumab. Additional nonlimiting examples of immunosuppressant drugs used to treat the overreacting immune system include Janus kinase inhibitors (tofacitinib (Xeljanz)); calcineurin inhibitors (cyclosporine (Neoral, Sandimmune, SangCya)), tacrolimus (Astagraf XL, Envarsus XR, Prograf)); mTOR inhibitors (sirolimus (Rapamune), everolimus (Afinitor, Zortress)); and, IMDH inhibitors (azathioprine (Azasan, Imuran), leflunomide (Arava), mycophenolate (CellCept, Myfortic)). Additional antibodies and biologics include abatacept (Orencia), adalimumab (Humira), anakinra (Kineret), certolizumab (Cimzia), etanercept (Enbrel), golimumab (Simponi), infliximab (Remicade), ixekizumab (Taltz), natalizumab (Tysabri), rituximab (Rituxan), secukinumab (Cosentyx), tocilizumab (Actemra), ustekinumab (Stelara), vedolizumab (Entyvio), basiliximab (Simulect), and daclizumab (Zinbryta)).

IL-1 blocks the production of IL-6 and other proinflammatory cytokines. COVID patients are also sometimes treated with anti-IL-1 therapy to reduce a hyperinflammatory response, for example, an intravenous administration of anakinra. Anti-IL-1 therapy generally may be for example, a targeting monoclonal antibody, pharmaceutical inhibitor or protein degrader such as a bispecific compound that binds to IL-1 and also to a protein that mediates degradation.

Patients with COVID often develop viral pneumonia, which can lead to bacterial pneumonia. Patients with severe COVID-19 can also be affected by sepsis or "septic shock". Treatment for bacterial pneumonia secondary to COVID or for sepsis includes the administration of antibiotics, for example a macrolide antibiotic, including azithromycin, clarithromycin, erythromycin, or roxithromycin. Additional antibiotics include amoxicillin, doxycycline, cephalexin, ciprofloxacin, clindamycin, metronidazole, sulfamethoxazole, trimethoprim, amoxicillin, clavulanate, or levofloxacin. In one embodiment, thus a compound of Formula I, Formula II, Formula III, Formula IV, or Formula V or a pharmaceutically acceptable salt thereof, is administered in combination or in alternation with an antibiotic, for example, azithromycin. Some of these antibiotics such as azithromycin have independent anti-inflammatory properties. Such drugs may be used both as anti-inflammatory agents for COVID patients and have a treatment effect on secondary bacterial infections.

A unique challenge in treating patients infected with COVID-19 is the relatively long-term need for sedation if patients require mechanical ventilation which might last up to or greater than 5, 10 or even 14 days. For ongoing pain during this treatment, analgesics can be added sequentially, and for ongoing anxiety, sedatives can be added sequentially. Non-limiting examples of analgesics include acetaminophen, ketamine, and PRN opioids (hydromorphone, fentanyl, and morphine). Non-limiting examples of sedatives include melatonin, atypical antipsychotics with sedative-predominant properties (olanzapine, quetiapine), propofol or dexmedetomidine, haloperidol, and phenobarbital. In one embodiment, a compound of Formula I, Formula II, Formula III, Formula IV, or Formula V or a pharmaceutically acceptable salt thereof, is administered in combination or in alternation with a pain reliever, such as acetaminophen, ketamine, hydromorphone, fentanyl, or morphine. In one embodiment, a compound of Formula I, Formula II, Formula III, Formula IV, or Formula V or a pharmaceutically acceptable salt thereof, is administered in combination or in alternation with a sedative, such as melatonin, olanzapine, quetiapine, propofol, dexmedetomidine, haloperidol, or phenobarbital.

Investigational drugs for COVID-19 include chloroquine and hydroxychloroquine. In one embodiment, a compound of Formula I, Formula II, Formula III, Formula IV, or Formula V or a pharmaceutically acceptable salt thereof, is administered in combination or in alternation with chloroquine or hydroxychloroquine.

A protease inhibitor such as lopinavir or ritonavir, previously approved for HIV, may also be administered.

Additional drugs that may be used in the treatment of a COVID patient include, but are not limited to favipiravir, fingolimod (Gilenya), methylprednisolone, bevacizumab (Avastin), Actemra (tocilizumab), umifenovir, losartan and the monoclonal antibody combination of REGN3048 and REGN3051 or ribavirin. Any of these drugs or vaccines can be used in combination or alternation with an active compound provided herein to treat a viral infection susceptible to such.

In one embodiment, a compound of the present invention is used in an effective amount in combination with anti-coronavirus vaccine therapy, including but not limited to mRNA-1273 (Moderna, Inc.), AZD-1222 (AstraZeneca and University of Oxford), BNT162 (Pfizer and BioNTech), CoronaVac (Sinovac), NVX-CoV 2372 (NovoVax), SCB-2019 (Sanofi and GSK), ZyCoV-D (Zydus Cadila), and CoVaxin(Bharat Biotech). In another embodiment, a compound of the present invention is used in an effective amount in combination with passive antibody therapy or convalescent plasma therapy.

SARS-CoV-2 is constantly mutating, which many increase virulence and transmission rates. Drug-resistant variants of viruses may emerge after prolonged treatment with an antiviral agent. Drug resistance may occur by mutation of a gene that encodes for an enzyme used in viral replication. The efficacy of a drug against an RNA virus infection in certain cases can be prolonged, augmented, or restored by administering the compound in combination or alternation with another, and perhaps even two or three other, antiviral compounds that induce a different mutation or act through a different pathway, from that of the principle drug.

Alternatively, the pharmacokinetics, bio distribution, half-life, or other parameter of the drug can be altered by such combination therapy (which may include alternation therapy if considered concerted). Since the disclosed purine nucleotides are polymerase inhibitors, it may be useful to administer the compound to a host in combination with, for example a:

(1) Protease inhibitor;
(2) Another polymerase inhibitor;
(3) Allosteric polymerase inhibitor;
(4) Interferon alfa-2a, which may be pegylated or otherwise modified, and/or ribavirin;
(5) Non-substrate-based inhibitor;
(6) Helicase inhibitor;
(7) Antisense oligodeoxynucleotide (S-ODN);
(8) Aptamer;
(9) Nuclease-resistant ribozyme;
(10) iRNA, including microRNA and SiRNA;
(11) Antibody, partial antibody or domain antibody to the virus; or
(12) Viral antigen or partial antigen that induces a host antibody response.

EXAMPLES

General Methods $^1$H, $^{19}$F and $^{31}$P NMR spectra were recorded on a 400 MHz Fourier transform Brücker spectrometer. Spectra were obtained DMSO-$d_6$ unless stated otherwise. The spin multiplicities are indicated by the symbols s (singlet), d (doublet), t (triplet), m (multiplet) and, br (broad). Coupling constants (J) are reported in Hz. The reactions were generally carried out under a dry nitrogen atmosphere using Sigma-Aldrich anhydrous solvents. All common chemicals were purchased from commercial sources.
The following abbreviations are used in the Examples:
BID: Twice a day
DCM: Dichloromethane
EtOAc: Ethyl acetate
EtOH: Ethanol
GT: Genotype
HPLC: High pressure liquid chromatography
LD: Loading dose
NaOH: Sodium hydroxide
Na$_2$SO$_4$: Sodium sulphate (anhydrous)
MeOH: Methanol
Na$_2$SO$_4$: Sodium sulfate
NH$_4$Cl: Ammonium chloride
PE: Petroleum ether
Silica gel (230 to 400 mesh, Sorbent)
t-BuMgCl: t-Butyl magnesium chloride
THF: Tetrahydrofuran (THF), anhydrous
TP: Triphosphate Example 1. Synthesis of Compound 1A and Compound 2A Part A: Synthesis of (2R,3R,4R,5R)-5-(2-amino-6-(methylamino)-9H-purin-9-yl)-4-fluoro-2-(hydroxymethyl)-4-methyltetrahydrofuran-3-ol (1-7)

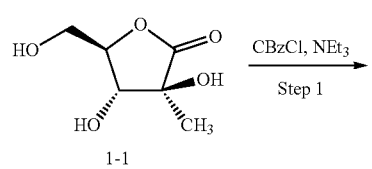

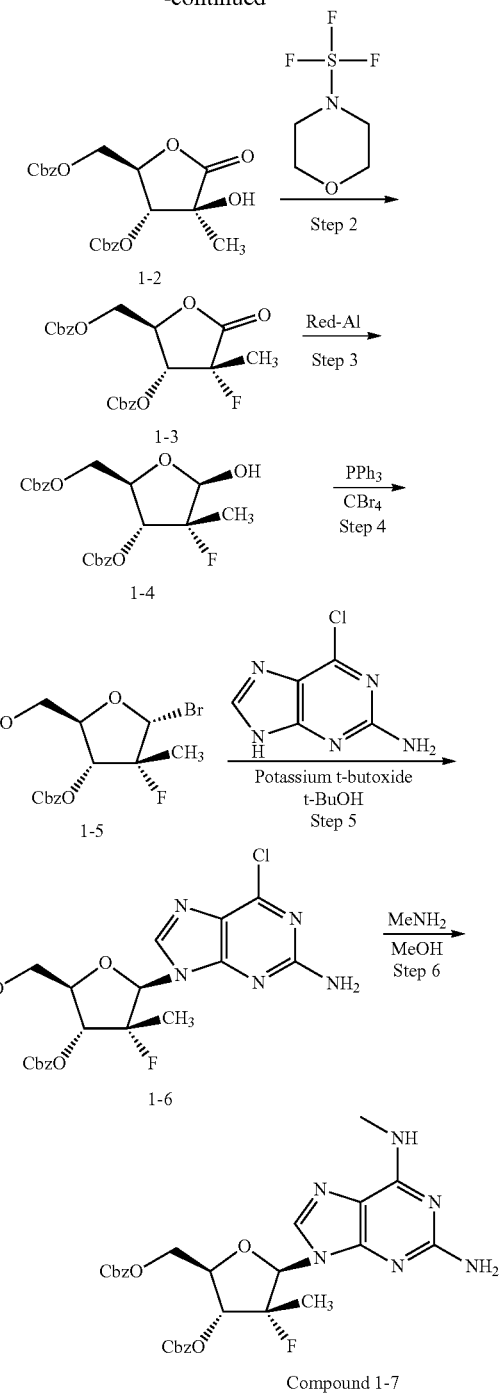

In Step 1, Compound 1-1 is dissolved in DCM and the reaction is cooled to 10° C. before benzyl chloroformate is added followed by NEt$_3$. The reaction is allowed to cool to room temperature and stir for 12-14 hours. Following appropriate work-up and purification conditions, Compound 1-2 is isolated. In Step 2, Compound 1-2 is dissolved in acetonitrile and cooled to −15 to 5° C. before Morpho DAST is added. The reaction is allowed to stir for 6 hours. Following appropriate work-up and purification conditions, Compound 1-3 is isolated. In Step 3, Compound 1-3 is dissolved in toluene and the reaction is cooled to 0-10° C. before Red Al is added. Following appropriate work-up and purification conditions, Compound 1-4 is isolated as the diastereomer with (R)-stereochemistry at the hydroxyl position. In Step 4, Compound 1-4 is dissolved in acetonitrile and cooled to −15 to 5° C. before CBr₄ and PPh₃ are added. Following appropriate work-up and purification conditions, Compound 1-5 is isolated. In Step 5, Compound 1-5 is dissolved is acetonitrile and t-BuOH, t-BuOK, and 6-chloro-9H-purin-2-amine are added. The reaction is heated to 40-50° C. Following appropriate work-up and purification conditions, Compound 1-6 is isolated. In Step 6, Compound 1-6 is dissolved in MeOH and MeNH₂ is added. The reaction is heated to 20-30 C. Following appropriate work-up and purification conditions, Compound 1-7 is isolated.

Part B: Synthesis of dihydroquinine salt of isopropyl (hydroxy(phenoxy)phosphoryl)-L-alaninate (1-12)

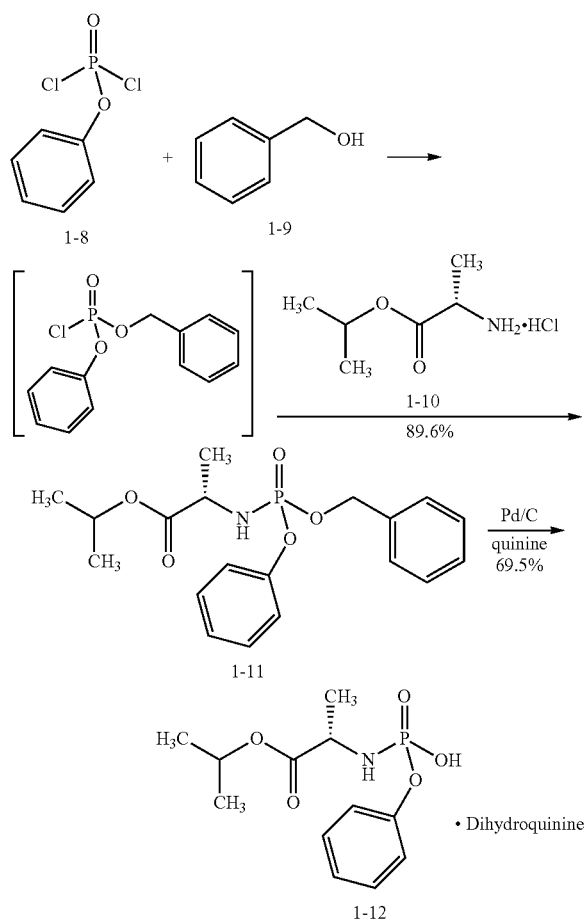

Phenyl dichlorophosphate (1-8, 150 g, 1.0 eq.) was added into 1300 mL of isopropyl acetate. The solution was cooled to −10° C.±5° C. and then a solution of benzyl alcohol (1-9, 80.6 g, 1.05 eq.) and Et₃N (86.3 g, 1.2 eq.) was added. The mixture was stirred for 3 hours at −10±5° C. The end point of reaction was monitored by TLC.

L-Alanine isopropyl ester hydrochloride (1-10, 125 g, 1.05 eq.) and Et₃N (152 g, 2.1 eq.) were added at −10° C.±5° C. The reaction mixture was stirred at −10±5° C. for 2 hours. The end point of reaction was monitored by TLC.

The reaction mixture was filtered, and the filter cake was washed with 20 mL of isopropyl acetate. The filtrate was washed with 1N HCl, water, and aqueous sodium bicarbonate. The separated organic layer was dried with anhydrous Na₂SO₄ and then concentrated to dryness under vacuum at 40° C.-50° C. to give 240 g of crude product 1-11 as a diastereomeric mixture (approximately, 1:1). (Pale yellow oil; yield: 89.6% mol/mol; HPLC purity: 83.4% by area; HPLC assay: 86.2% w/w). The product contained around 6%-7% residual benzyl alcohol. The crude 1-4 was used directly in the next step.

Compound 1-11 (135 g, 1.0 eq., 86.2% assay) and quinine (100 g, 1.0 eq.) were added into 650 mL of i-PrOH. After 5% Pd/C (19.2 g, 60% water by KF) was added, hydrogenation was performed at 20° C.-25° C. for 8 hours using a hydrogen bag in a closed system. After completion of reaction, the mixture was filtered through a Büchner funnel. The filtrate was concentrated under vacuum to remove the solvent.

To the above residue, 300 mL of TBME was added. The mixture was concentrated to remove the solvent under vacuum at 40° C.-45° C., and then this step was repeated with another 300 mL of MTBE. To the above, 600 mL of MTBE was added, and the mixture was stirred at 40° C.-45° C. for 1 hour and then stirred at 0° C.-5° C. for additional 1 hour. The mixture was filtered, and the filter cake was washed with 100 mL of MTBE. The cake was dried at 45° C. for 16 hours without vacuum to give 152 g of the dihydroquinine salt of isopropyl (hydroxy(phenoxy)phosphoryl)-L-alaninate (1-12, white solid; yield: 69.5% mol/mol; HPLC Purity: 97.91%).

Part C: Synthesis of Compound 1A

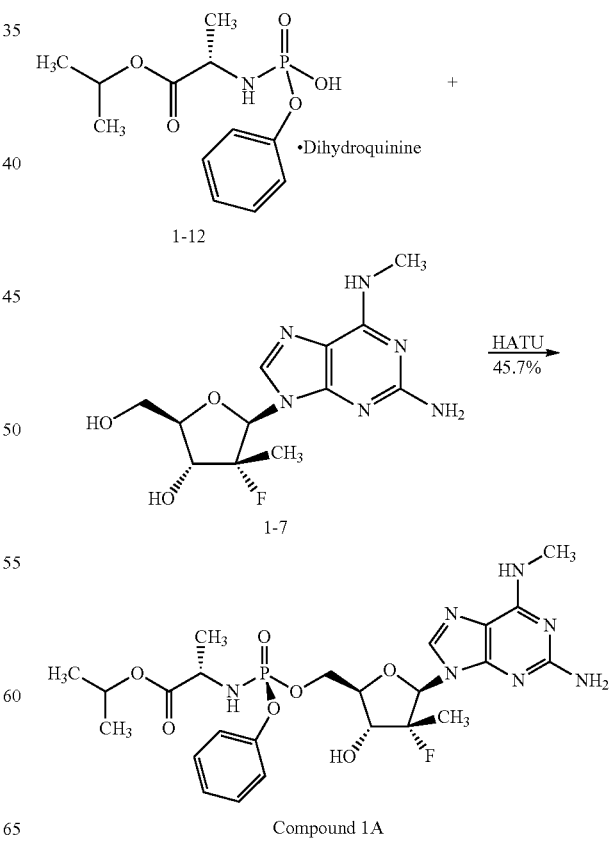

The dihydroquinine salt of isopropyl (hydroxy(phenoxy) phosphoryl)-L-alaninate (1-12, 5.9 g, 1.5 eq.), Compound 1-7 (2.0 g, 1.0 eq), DIPEA (0.83 g, 1.0 eq), and HATU (3.65 g, 1.5 eq) were added into 100 mL of dichloromethane. The mixture was heated to 40° C. and stirred for 18 hours. The reaction was monitored by TLC and HPLC.

After the reaction was completed, the reaction mixture was cooled to room temperature, washed with 1N hydrochloric acid (100 mL×2), water (100 mL×2), and 5% aqueous sodium bicarbonate 15 mL×1). The separated organic phase was dried with 2 g of anhydrous sodium sulfate, filtered, and concentrated at 40° C.-45° C. under vacuum to give a yellow oil.

Isopropyl acetate (10 mL of) was added. After stirring, the mixture was concentrated under vacuum. Then, 25 mL of isopropyl acetate was added. The mixture was heated to 45° C. to afford a clear solution. After stirring at room temperature for 2 hours, the solid precipitate was filtered and dried without vacuum at 45° C. for 15 hours to give 2.0 g of crude Compound 1A (yield: 53.8% mol/mol; HPLC purity: 93.1% by area (containing 3.7% of $R_p$-Compound 1B).

The mixture of crude Compound 1A (2.0 g) and 15 mL of isopropyl acetate was heated to 80° C.-85° C. to afford a solution. The solution was cooled to 20° C.-25° C. and stirred for 1 hour. The precipitated solid was filtered, washed with isopropyl acetate (1 mL), and dried without vacuum at 50° C. for 16 hours to give 1.7 g of Compound 1A (yield: 45.7% mol/mol; HPLC purity: 98.99%). $^1$H NMR, $^{19}$F NMR, and $^{31}$P NMR spectra confirmed the structure of Compound 1A.

Example 2. Synthesis of Hemi-Sulfate Salt Compound 2A

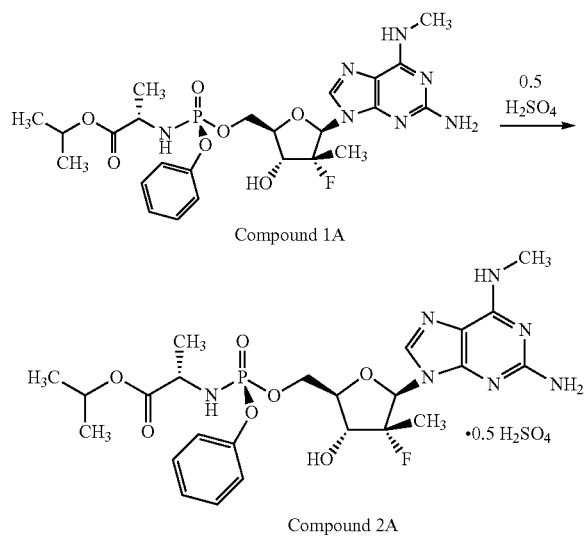

A 250 mL flask was charged with MeOH (151 mL) and the solution was cooled to 0-5° C. A concentrated solution of $H_2SO_4$ was added dropwise over 10 minutes. A separate flask was charged with Compound 1A (151 g) and acetone (910 mL), and the $H_2SO_4$/MeOH solution was added dropwise at 25-30° C. over 2.5 hours. A large amount of solid was precipitated. After the solution was stirred for 12-15 hours at 25-30° C., the mixture was filtered, washed with MeOH/acetone (25 mL/150 mL), and dried at 55-60° C. in vacuum to afford Compound 2A (121 g, 74%). $^1$HNMR: (400 MHz, DMSO-d$_6$): δ 8.41 (br, 1H), 7.97 (s, 1H), 7.36 (t, J=8.0 Hz, 2H), 7.22 (d, J=8.0 Hz, 2H), 7.17 (t, J=8.0 Hz, 1H), 6.73 (s, 2H), 6.07 (d, J=8.0 Hz, 1H), 6.00 (dd, J=12.0, 8.0 Hz, 1H), 5.81 (br, 1H), 4.84-4.73 (m, 1H), 4.44-4.28 (m, 3H), 4.10 (t, J=8.0 Hz, 2H), 3.85-3.74 (m, 1H), 2.95 (s, 3H), 1.21 (s, J=4.0 Hz, 3H), 1.15-1.10 (m, 9H).

Example 3. Activity of Compound 1A Against Coronavirus in Huh7 Cells

The activity of Compound 1A was tested against the human coronaviruses alpha-229E and beta-OC43 in Huh7 cells.

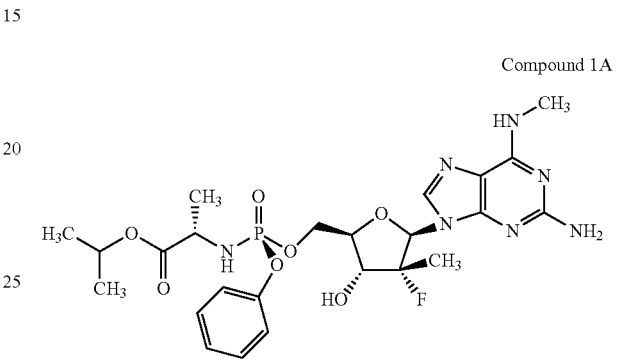

Huh7 cells were seeded in 96-well plates at a concentration that yielded 80-100% confluent monolayers in each well after overnight incubation. Compound 1A was dissolved in DMSO to 10 mg/mL and 8 half-log serial dilutions in test medium (modified Eagle's medium containing 5% fetal bovine serum and 50 μL gentamicin) were prepared with the highest concentration of 50 μg/mL. 100 μL of each concentration were added to 5 test wells on the 96-well plate and 3 wells were infected with test virus in test medium (≤100 CCID$_{50}$ per well). An equivalent amount of test medium was added to the remaining test wells to assess toxicity to uninfected cells. Six wells were infected to serve as untreated virus controls. Media only was added to 6 wells to serve as cell controls. Plates were incubated at 37° C. in a humidified 5% CO$_2$ atmosphere until cytopathic effect (CPE) was observed microscopically.

To obtain the CPE endpoint, wells were stained with 0.011% neutral red dye for approximately 2 hours. The dye was siphoned off and wells were rinsed once with phosphate-buffered saline to remove residual, unincorporated dye. 200 μL of 50:50 Sorensen citrate buffer/ethanol was added for >30 min with agitation and then light absorbance at 540 nm was measured on a spectrophotometer.

To obtain the virus yield reduction (VYR) endpoint, supernatant fluid from 3 replicate wells of each compound concentration were pooled and virus titer was measured using a standard endpoint dilution CCID$_{50}$ assay and titer calculations using the Reed Muench (1948) equation (Reed, U and Muench, H. Am. *J. Hygiene* 27:493-497 (1948)). The concentration of compound required to reduce virus yield by 1 log$_{10}$ (EC$_{90}$) was determined using regression analysis.

As shown in Table 1, Compound 1A is potent against both the alpha-229E coronavirus and the beta-OC43 coronavirus. Compound 1A exhibits an EC$_{90}$ value of 0.71 μM against alpha-229E in the virus yield reduction assay and an EC$_{90}$ value of 0.29 μM against beta-OC43. Additionally, Compound 1A exhibits high CC$_{50}$ values and selectivity indexes (SI) against both the alpha and beta coronaviruses. For example, against the beta coronavirus, Compound 1A has a selectivity index of greater than 170 when measured using the viral yield reduction assay and a $CC_{50}$ value of greater than 50 μM when measured in neutral red assay.

TABLE 1

Activity of Compound 1A against Coronaviruses Alpha-229E and Beta-OC43

| Virus in Huh7 cells | Visual | | | Neutral Red | | | VYR | |
|---|---|---|---|---|---|---|---|---|
| | $EC_{50}$ (μM) | $CC_{50}$ (μM) | SI | $EC_{50}$ (μM) | $CC_{50}$ (μM) | SI | $EC_{90}$ (μM) | SI |
| Alpha-229E | 1 | >50 | >50 | 1 | >50 | >50 | 0.71 | >70 |
| Beta-OC43 | NT | >50 | NT | NT | >50 | NT | 0.29 | >170 |

Visual and neutral red SI: $CC_{50}/EC_{50}$
VYR SI: $CC_{50}/EC_{90}$
NT: not tested Example 4. Activity of Compound 1A and 1B Against Coronavirus in BHK-21 and MES-21 Cells Compound 1A and Compound 1B were tested for activity against human coronavirus in BHK-21 cells (Table 2A and Table 2B) and MES-1 cells (Table 3A and Table 3B). The $EC_{50}$ and the $CC_{50}$ was determined and compared to Sofosbuvir.

Compound activity against coronavirus was based on inhibition of virus induced cytopathogenicity acutely infected with a multiplicity of infection (m.o.i.) of 0.01. After a 3-day incubation at 37° C. cell viability was determined by the MTT method as described by Pauwels et al. (J. Virol. Methods 1988, 20, 309-321).

To determine the cytotoxicity, cells were seeded at an initial density of 1×106 cells/mL in 96 well plates containing Minimum Essential Medium with Earles's salts (MEM-E), L-glutamine, 1 mM sodium pyruvate and 25 mg/L kanamycin, supplemented with 10% fetal bovine serum. Cell cultures were then incubated at 37° C. in a humidified 5% $CO_2$ atmosphere in the absence or presence of serial dilutions of test compounds. Cell viability was determined by the MTT method.

TABLE 2A

Activity of Select Compounds against HCoV in BHK-21 Cells

| Compound | $CC_{50}$ [uM]$^a$ | $EC_{50}$ [uM]$^b$ |
|---|---|---|
| 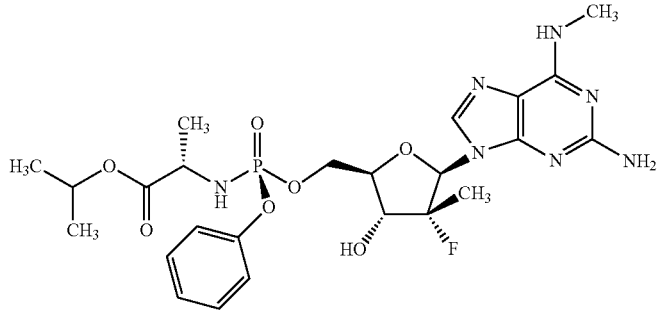<br>Compound 1A | >100 | 1.6 |
| 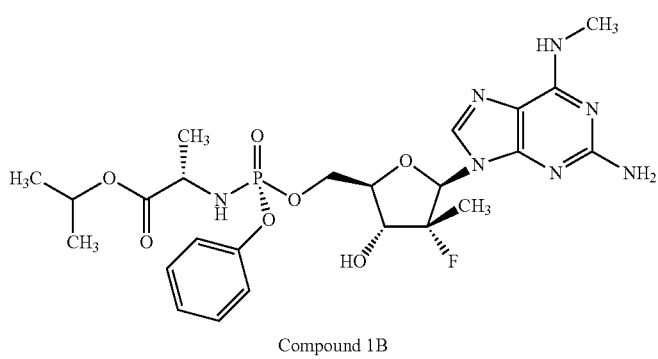 [SMILES: CNc1nc(N)nc2c1ncn2[C@@H]1O[C@H](CO[P@](=O)(N[C@@H](C)C(=O)OC(C)C)Oc2ccccc2)[C@@H](O)[C@@]1(C)F]<br>Compound 1B | >100 | 2.5 |

TABLE 2A-continued

Activity of Select Compounds against HCoV in BHK-21 Cells

| Compound | $CC_{50}$ [uM]$^a$ | $EC_{50}$ [uM]$^b$ |
|---|---|---|
| 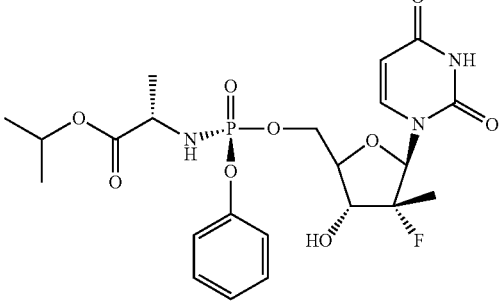Sofosbuvir | >100 | >100 |

$^a$Compd conc. (μM) required to reduce the viability of mock infected BHK cells by 50% as determined by the MTT method after 3 days of incubation
$^b$Compd conc. (μM) required to achieve 50% protection of BHK cells from virus-induced cytopathogenicity as determined by the MTT method at day 3 post-infection

TABLE 2B

Activity of Select Compounds against HCoV in BHK-21 Cells

| Compound | $CC_{50}$ [uM]$^a$ | $EC_{50}$ [uM]$^b$ |
|---|---|---|
| 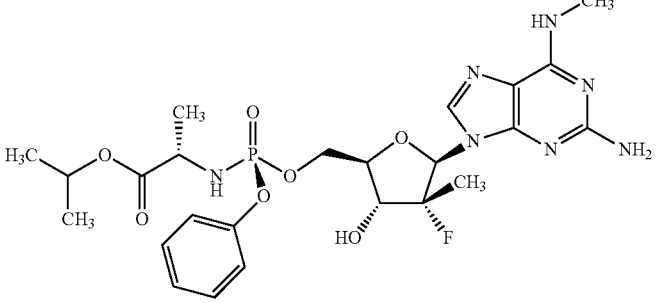Compound 1A | >100 | 2.0 |
| 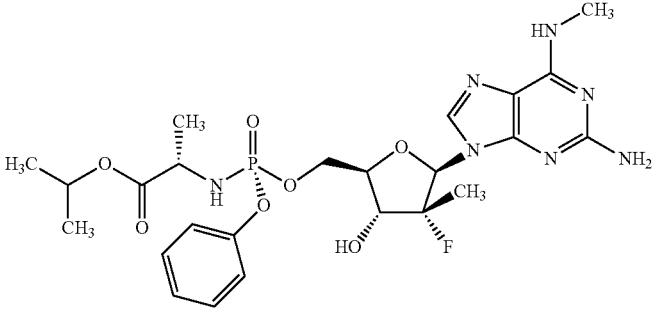Compound 1B | >100 | 2.9 |

TABLE 2B-continued

| Activity of Select Compounds against HCoV in BHK-21 Cells | | |
|---|---|---|
| Compound | $CC_{50}$ [uM][a] | $EC_{50}$ [uM][b] |
| 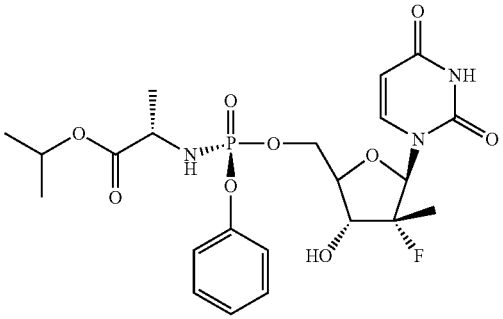 Sofosbuvir | >100 | >100 |

[a]Compd conc. (μM) required to reduce the viability of mock infected BHK cells by 50% as determined by the MTT method after 3 days of incubation
[b]Compd conc. (μM) required to achieve 50% protection of BHK cells from virus-induced cytopathogenicity as determined by the MTT method at day 3 post-infection

TABLE 3A

| Activity of Select Compounds against HCoV in MES-1 Cells | | |
|---|---|---|
| | $CC_{50}$ [uM][c] | $EC_{50}$ [uM][d] |
| 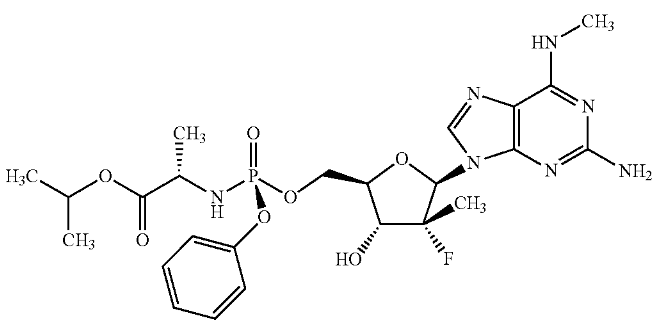  Compound 1A | >100 | 1.6 |
| 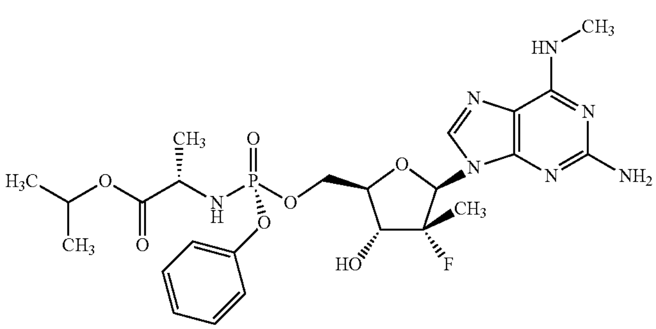  Compound 1B | >100 | 2.0 |

TABLE 3A-continued

Activity of Select Compounds against HCoV in MES-1 Cells

| | $CC_{50}$ [uM][c] | $EC_{50}$ [uM][d] |
|---|---|---|
| 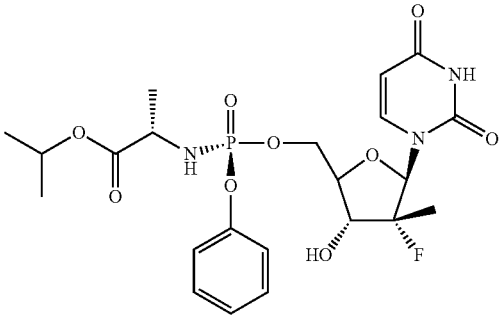
Sofosbuvir | >100 | >100 |

[c]Compd conc. (μM) required to reduce viability of mock infected MES-1 cells by 50% as determined by the MTT method after 3 days of incubation
[d]Compd conc. (μM) required to achieve 50% protection of MES-1 cells from virus-induced cytopathogenicity as determined by the MTT method at day 3 post-infection

TABLE 3B

Activity of Select Compounds against HCoV in MES-1 Cells

| | $CC_{50}$ [uM][c] | $EC_{50}$ [uM][d] |
|---|---|---|
| 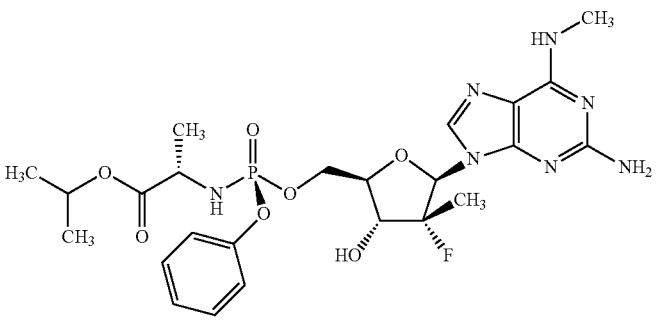
Compound 1A | >100 | 2.0 |
| 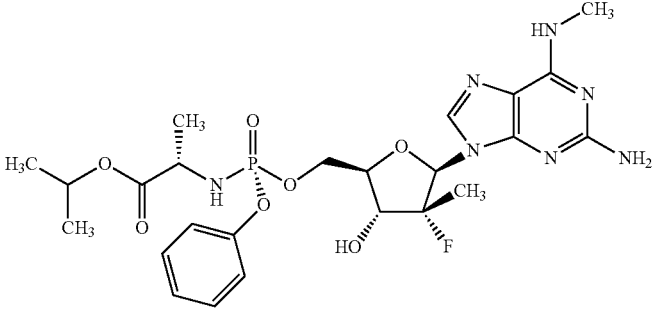
Compound 1B | >100 | 2.2 |

TABLE 3B-continued

Activity of Select Compounds against HCoV in MES-1 Cells

| | $CC_{50}$ [uM][c] | $EC_{50}$ [uM][d] |
|---|---|---|
| 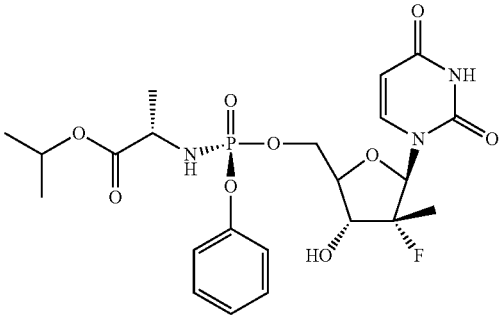<br>Sofosbuvir | >100 | >100 |

[c]Compd conc. (µM) required to reduce viability of mock infected MES-1 cells by 50%, as determined by the MTT method after 3 days of incubation.
[d]Compd conc. (µM) required to achieve 50% protection of MES-1 cells from virus-induced cytopathogenicity as determined by the MTT method at day 3 post-infection

Example 5. Activity of Compound 1A Against SARS-CoV and SARS-CoV-2

Compound 1A was tested against SARS-CoV in Huh7 cells and SARS-CoV-2 in HAL cells (human airway epithelial cells; also referred to as differentiated normal human bronchial epithelial (dNHBE) cells) and the results are provided in Table 4. The $CC_{50}$ was determined using the neutral red assay and the $EC_{90}$ and SI were determined using the virus yield reduction assay. The $EC_{90}$ is provided in µg/mL and µM. Compound 1A exhibits an $EC_{90}$ of 0.34 µM against SARS-CoV. Against SARS-CoV-2, Compound 1A exhibits $EC_{90}$ values ranging from 0.47 µM, 0.51 µM, and 0.64 µM (average of 0.54 µM).

TABLE 4

Activity of Compound 1A Against SARS-CoV and SARS-CoV-2

| HuCoV | | Neutral Red Assay | Virus Yield Reduction Assay | | |
|---|---|---|---|---|---|
| Virus (strain) | Cell Line | $CC_{50}$ (µg/mL) | $EC_{90}$ (µg/mL) | $EC_{90}$ (µM) | Selectivity Index |
| SARS-CoV (Urbani) | Huh7 | >50 | 0.2 | 0.34 | >250 |
| SARS-CoV-2 (WA1) | HAE | >50[1] | 0.37[2] | 0.64 | >135 |

[1]$CC_{50}$ was estimated by visual inspection of the cells
[2]Value represents the mean of two replicate $EC_{90}$ determinations, 0.33 and 0.41 µg/mL The activity of Compound 1A was evaluated in Huh-7 cells infected with SARS-CoV (Urbani) in a neutral red (NR) assay to assess cytotoxicity and then tested using a virus yield reduction (VYR) assay to assess antiviral activity.

Neutral red assay: Compound 1A was dissolved in 100% DMSO at a concentration of 10 mg/mL and serially diluted using eight half-log dilutions in test medium (Minimum Essential Medium supplemented with 5% FBS and 50 µg/mL gentamicin). The starting (high) test concentration was 50 µg/mL. Each dilution was added to 5 wells of a 96-well plate with 80-100% confluent Huh7 or RD cells (hCoV beta OC43 only). Three wells of each dilution were infected with virus and two wells remained uninfected as toxicity controls. Six untreated wells were infected as virus controls and six untreated wells were left uninfected to use as cell controls. Viruses were diluted to a specific 50% cell culture infectious dose ($CCID_{50}$) per mL to achieve the lowest possible multiplicity of infection (MOI) that would yield >80% toxicity within 5-7 days. The MOI was 0.03 $CCID_{50}$/cell. Plates were incubated at 37±2° C., 5% CO2.

On day 7 post-infection (p.i.), the plates were stained with neutral red dye for approximately 2 hours (±15 minutes). Supernatant dye was removed, wells were rinsed with PBS, and the incorporated dye was extracted in 50:50 Sorensen citrate buffer/ethanol for >30 minutes and the optical density was read on a spectrophotometer at 540 nm. Optical densities were converted to percent of cell controls and the concentration of Compound 1A required to cause 50% cell death in the absence of virus was calculated ($CC_{50}$). The selective index (SI) is the $CC_{50}$ divided by the $EC_{50}$.

Virus yield reduction assay: Vero76 cells were seeded in 96-well plates and grown overnight (37° C.) to 80% confluency. A sample of the supernatant fluid from each compound concentration was collected on day 3 post-infection (3 wells pooled) and tested for virus titer using a standard endpoint dilution $CCID_{50}$ assay and titer calculations using the Reed-Muench (1948) equation (Reed, L J and Muench, H. Am. J. Hygiene 27:493-497 (1948)). The concentration of compound required to reduce virus yield by 1 log 10 ($EC_{90}$) was calculated by regression analysis.

The antiviral activity of Compound 1A was next evaluated against SARS-CoV-2 (WA1) using HAE cells made to order by MatTek Corporation (Ashland, MA).

Cell Culture: HAE cells were grown on 6 mm mesh disks and arrived in kits with either 12- or 24-well transwell inserts. During transportation, the tissues were stabilized on a sheet of agarose, which was removed upon receipt. One insert was estimated to consist of approximately 1.2×106 cells. Kits of cell inserts (EpiAirway™ AIR-100, AIR-112) originated from a single donor, #9831, a 23-year old, healthy, non-smoking, Caucasian male. The cells have unique properties in forming layers, the apical side of which is exposed only to air and that creates a mucin layer. Upon arrival, the cell transwell inserts were immediately transferred to individual wells of a 6-well plate according to manufacturer's instructions, and 1 mL of MatTek's proprietary culture medium (AIR-100-MM) was added to the basolateral side, whereas the apical side was exposed to a humidified 5% $CO_2$ environment. Cells were cultured at 37° C. for one day before the start of the experiment. After the 24 hour equilibration period, the mucin layer, secreted from the apical side of the cells, was removed by washing with 400 µL pre-warmed 30 mM HEPES buffered saline solution 3×. Culture medium was replenished following the wash steps.

Viruses: Virus was diluted in AIR-100-MM medium before infection, yielding a multiplicity of infection (MOI) of approximately 0.0015 $CCID_{50}$ per cell.

Experimental design: Each compound treatment (120 µL) and virus (120 µL) was applied to the apical side. At the same time, the compound treatment (1 mL) was applied to the basal side for a 2-h incubation. As a virus control, some of the cells were treated with placebo (cell culture medium only). Following the 2-h infection, the apical medium was removed, and the basal side was replaced with fresh compound or medium (1 mL). The cells were maintained at the air-liquid interface. On day 5, cytotoxicity ($CC_{50}$ values) in the placebo-treated inserts was estimated by visual inspection, and the medium was removed from all inserts and discarded from the basal side. Virus released into the apical compartment of the HAE cells was harvested by the addition of 400 µL of culture medium that was pre-warmed at 37° C. The contents were incubated for 30 minutes, mixed well, collected, thoroughly vortexed and plated on Vero 76 cells for VYR titration. Duplicate wells were used for virus control and cell controls.

Determination of virus titers from each treated cell culture: Vero 76 cells were seeded in 96-well plates and grown overnight (37° C.) to confluence. Samples containing virus were diluted in 10-fold increments in infection medium and 200 µL of each dilution transferred into respective wells of a 96-well microtiter plate. Four microwells were used for each dilution to determine 50% viral endpoints. After 5 days of incubation, each well was scored positive for virus if any cytopathic effect (CPE) was observed as compared with the uninfected control and counts were confirmed for endpoint on days 6 and 7. The virus dose that was able to infect 50% of the cell cultures ($CCID_{50}$ per 0.1 mL) was calculated by the Reed-Muench method (1948) (Reed, L J and Muench, H. Am. J. Hygiene 27:493-497 (1948)) and the 90% effective concentration ($EC_{90}$; concentration to reduce virus yield by 1 log 10) was determined by regression analysis. The day 5 values were reported. Untreated, uninfected cells were used as the cell controls.

Example 6. In Vitro Activity of Compound 1A and Other Oral Antiviral Drugs Against Various Human Coronaviruses Compound 1A and other oral antiviral drugs were tested against various human coronaviruses (Table 5) in various cell lines. The data demonstrate the potent in vitro activity of Compound 1A against several CoVs, with individual $EC_{90}$ values ranging from 0.34 to 1.2 µM against HCoV-229E, HCoV-OC43, SARS-CoV-1 and SARS-CoV-2 and less activity against MERS-CoV (average $EC_{90}$=36 µM). Against SARS-CoV-2, Compound 1A exhibits $EC_{90}$ values ranging from 0.47 µM, 0.51 µM, and 0.64 µM (average of 0.54 µM).

TABLE 5

Activity of Compound 1A and Other Oral Antiviral Drugs Against Human Coronaviruses

| Virus (genus) | Cell line | Compound | Neutral Red Assay | | Virus Yield Reduction Assay | Selectivity Index |
|---|---|---|---|---|---|---|
| | | | $EC_{50}$ (µM) | $CC_{50}$ (µM) | $EC_{90}$ (µM) | ($CC_{50}/EC_{90}$) |
| HCoV-229E (alpha) | BHK-21 | Compound 1A | 1.8[a,b] | >100 | | >58[c] |
| | | sofosbuvir | >100[b] | >100 | | N/A |
| | Huh-7 | Compound 1A | 1.7/1.6 | >86 | 1.0 | >75 |
| | | chloroquine | 8.1 | 21 | <0.050 | 2.6[c] |
| | | hydroxychloroquine | 7.4 | 26 | <0.048 | 3.5[c] |
| HCoV-OC43 (beta) | Huh-7 | Compound 1A | ND[d] | >86 | 0.5/<0.03 | >170/>3100 |
| | RD | Compound 1A | 2.8 | >86 | 2.2 | >39 |
| MERS-CoV (beta) | Huh-7 | Compound 1A | 15/36 | >86 | 17/56 | >5/>1.5 |
| SARS-CoV-1 (beta) | Huh-7 | Compound 1A | ND | >86 | 0.34 | >250 |
| SARS-CoV-2 (beta) | HAE | Compound 1A | ND | >86[e]/>8.6[e] | 0.64[f]/0.47[g] | >130/>18 |
| | | $N^4$-hydroxycytidine | | >19[e] | 3.9[h] | >5.1 |

[a]Average of 2 experiments (1.6 and 2.0 µM)
[b]$EC_{50}$ determined by dye staining (virus yield reduction substantially overestimates antiviral potency of cytotoxic compounds)
[c]$CC_{50}/EC_{50}$
[d]Not determined (no cytopathic effect with this virus in this cell line)
[e]Cytotoxicity assessed by visual inspection of cell monolayers
[f]Average of two replicates (0.57 and 0.70 µM)
[g]Average of two replicates (0.52 and 0.42 µM)
[h]Average of two replicates (4.7 and 3.1 µM)
BHK-21, baby hamster kidney cell line
Huh-7, human hepatocyte carcinoma cell line (established ability to form triphosphate from Compound 1A)
RD, human rhabdomyosarcoma cell line (unknown ability to form triphosphate from Compound 1A)
HAE, human airway epithelial cell culture (established ability to form triphosphate from Compound 1A) (established ability to form triphosphate from Compound 1A)

In an initial screening, BHK-21 cells acutely infected with a seasonal human alpha coronavirus, HCoV-229E, were exposed to serial dilutions of Compound 1A. After a 3-day incubation, the effective concentration of Compound 1A required to achieve 50% inhibition ($EC_{50}$) of the virus-induced cytopathic effect (CPE) from two independent experiments averaged 1.8 µM. In contrast, the 2'-fluoro-2'-methyl uridine nucleotide prodrug sofosbuvir did not inhibit HCoV-229E replication at concentrations as high as 100 µM (Table 5). No toxicity was detected from either drug.

The in vitro potency of Compound 1A against HCoV-229E, HCoV-OC43 (another seasonal human coronavirus strain), MERS-CoV and SARS-CoV-1 was then evaluated in Huh-7 cell-based assays. This human hepatocarcinoma cell line was selected based on its ability to activate Compound 1A intracellularly to its triphosphate metabolite, unlike MRC-5 cells in which Compound 1A lacked activity against HCoV-229E ($EC_{50}$>100 µM) as reported in Good, S. S. et al. PLoS One 15(1), e0227104 (2020)). Antiviral activity was assessed by two different methods after exposure of Huh-7 cells to virus and serial dilutions of test compound by determining 1) the $EC_{50}$ for virus-induced CPE by neutral red dye staining after a 5-day (229E and OC43) or 7-day (MERS and SARS) incubation and 2) the effective concentration required to reduce secretion of infectious virus into the culture medium by 90% ($EC_{90}$) after a 3-day incubation using a standard endpoint dilution $CCID_{50}$ assay to determine virus yield reduction (VYR). Half-maximal cytotoxicity ($CC_{50}$) was measured by neutral red staining of compound-treated duplicates in the absence of virus. Although a robust VYR endpoint was obtained in Huh-7 cells infected with HCoV-OC43 or SARS-CoV-1, CPE was not observed and $EC_{50}$ values using neutral red staining were not obtained with these viruses. Individual determinations of $EC_{90}$ values for Compound 1A against HCoV-229E, HCoV-OC43 and SARS-CoV-1 ranged from 0.34 to 1.2 µM, whereas the value against MERS-CoV averaged 37 µM (Table 5). No cytotoxicity was detected with Compound 1A up to 86 µM, the highest concentration tested.

Chloroquine and hydroxychloroquine appeared to be quite potent against HCoV-229E and HCoV-OC43 based on their $EC_{90}$ values of <0.05 µM obtained using VYR measurements (Table 5). The respective $EC_{50}$ values for these two drugs (8.1 and 7.4 µM), obtained using the neutral red assay, were substantially higher and only 2.6- to 3.6-fold less than the corresponding $CC_{50}$ values, indicating considerably lower potencies and poor selectivity indices. These differences illustrate an inherent error in assessing antiviral activities of cytotoxic compounds using only measurements of VYR. When cells are poisoned by toxic drugs and are progressing toward death, their ability to support viral replication and propagation in addition to their own health likely is greatly diminished. At the point when cell death is detected by staining, viral yield reduction measurements likely reflect a combination of antiviral activity and cytotoxicity, thus overestimating antiviral potencies.

In contrast to data published in Wang, M. et al. (Cell Research 2020, 30, 269), Huh-7 cells were not permissive for replication of SARS-CoV-2. An assay was developed using human airway epithelial (HAE) cell preparations, a highly relevant in vitro model of the lung, which has been established as a more representative system than cell lines for SARS-CoV-2 replication (Jomsdottir, H. R., Virol. J. 13, 24 (2016)). These primary cells form polarized monolayers, the apical side of which is exposed to air and produces a mucin layer, consistent with the physiology of the human airways (Jomsdottir, H. R., Virol. J. 13, 24 (2016)). Average $EC_{90}$ and $CC_{50}$ values for Compound 1A against SARS-CoV-2 from two separate HAE assays (0.5 and >86 µM, respectively) were in the same range as those obtained for HCoV-OC43 and SARS-CoV-1 (Table 5).

In the second HAE assay, the activity of Compound 1A was tested in parallel with $N^4$-hydroxycytidine with recently reported in vitro and in vivo activity against SARS-CoV-2 (Sheahan, T. P. et al. Sci. Transl. Med. 12, eabb5883 (2020)). The potency of $N^4$-hydroxycytidine against SARS-CoV-2 ($EC_{90}$=3.9 µM) was 8 times less than that of Compound 1A in the same experiment.

A 30-fold difference of Compound 1A activity between MERS-CoV and other CoVs was observed. Nucleotide and nucleotide analogue selection is achieved at the CoV RdRp active site, the nsp12 gene product activated by its processivity co-factors nsp7 and nsp8 (Subissi, L., Proc. Natl. Acad. Sci. USA 111 (37) 3900-9 (2014)). Conserved amino acid motifs A and C are involved in phosphodiester bond formation, whereas motifs F and B participate in nucleotide channeling and binding at the active site, respectively. No significant structural differences are apparent between MERS-CoV and other CoVs in these essential motifs. With a similar ribose modification between Compound 1A and sofosbuvir, it is unlikely that the selective lack of activity of sofosbuvir would be due to excision by the CoV exonuclease carried by nsp14 (Ferron, F., Proc. Natl. Acad. Sci. USA 115 (2) 162-171 (2018)). Rather, the results suggest that the triphosphate formed from Compound 1A most likely targets another less conserved viral GTP-binding protein, whose inhibition would account for both the antiviral effect and the MERS-CoV differential sensitivity pattern.

Cells, Antivirals and Viruses

BHK-21 (baby hamster kidney) cells, Huh-7 (human hepatocarcinoma) cells, RD (human rhabdomyosarcoma) cells and the seasonal human coronaviruses (HCoV-229E and HCoV-OC43) were obtained from American Type Culture Collection, Manassas, VA. MERS-CoV (EMC), SARS-CoV-1 (Urbani) and SARS-CoV-2 (USA-WA1/2020) were supplied by The Centers for Disease Control and Prevention, Atlanta, GA. The HAE cell preparations (EpiAirway™ AIR-100 or AIR-112) were purchased from MatTek Corporation, Ashland, MA. Compound 1A and N4-hydroxycytidine were prepared for Atea Pharmaceuticals by Topharman Shanghai Co., Ltd., Shanghai, China and Oxeltis, Montpellier, France, respectively. Chloroquine and hydroxychloroquine were purchased from Mason-Chem, Palo Alto, CA and sofosbuvir was purchased from Pharma Sys, Inc., Cary, NC.

Antiviral Assays

BHK-21 cells: Test compounds were dissolved in DMSO at 100 mM and then diluted in Minimum Essential Medium with Earle's salts (MEM-E) containing 1 mM sodium pyruvate and 25 µg/mL kanamycin, supplemented with 10% FBS (growth medium) to final concentrations of 100, 20, 4 and 0.8 µM (two 24-well replica plates each). After BHK-21 cells were grown to confluency in 96-well plates, growth medium was replaced with fresh maintenance medium (growth medium with 1% inactivated FBS in place of 10% FBS) containing serially diluted test compound and HCoV-229E at a multiplicity of infection (MOI) of 0.01. Uninfected cells in the presence of serially diluted compound were used to assess the cytotoxicity of compounds. After a 3-day incubation at 37° C. in a humidified 5% $CO_2$ atmosphere, cell viability was determined by the MTT method (Pauwels, R et al. J. Virol. Methods 20(4):309-321 (1988)). The effective concentration of test compound required to prevent virus-induced cytopathic effect (CPE) by 50%

($EC_{50}$) and to cause 50% cell death in the absence of virus ($CC_{50}$) were calculated by regression analysis.

Huh-7 and RD cells: The antiviral activities of test compounds were evaluated against human coronaviruses alpha (229E), beta (OC43), MERS (EMC) and SARS (Urbani) using a neutral red assay to determine inhibition of virus-induced and compound-induced CPE and using a virus yield reduction (VYR) assay as a second, independent determination of the inhibition of virus-induced CPE.

Neutral red assay: Test compounds were dissolved in DMSO at a concentration of 10 mg/mL and serially diluted using eight half-log dilutions in test medium (Minimum Essential Medium supplemented with 5% FBS and 50 μg/mL gentamicin) so that the highest test concentration was 50 μg/mL. Each dilution was added to 5 wells of a 96-well plate with 80-100% confluent Huh-7 or RD cells (OC43 only). Three wells of each dilution were infected with virus, and two wells remained uninfected as toxicity controls. Six untreated wells were infected as virus controls and six untreated wells were left uninfected to use as virus controls. Viruses were diluted to achieve MOIs of 0.003, 0.002, 0.001 and 0.03 $CCID_{50}$ per cell for 229E, OC43, MERS and SARS, respectively. Plates were incubated at 37±2° C. in a humidified atmosphere containing 5% $CO_2$.

On day 5 (229E and OC43) or day 7 (MERS and SARS) post-infection, when untreated virus control wells reached maximum CPE, the plates were stained with neutral red dye for approximately 2 hours (±15 minutes). Supernatant dye was removed, wells were rinsed with PBS, and the incorporated dye was extracted in 50:50 Sorensen citrate buffer/ethanol for >30 minutes and the optical density was read on a spectrophotometer at 540 nm. Optical densities were converted to percent of controls and the concentrations of test compound required to prevent virus-induced CPE by 50% ($EC_{50}$) and to cause 50% cell death in the absence of virus ($CC_{50}$) were calculated.

Virus yield reduction assay: Vero 76 cells were seeded in 96-well plates and grown overnight (37° C.) to confluence. A sample of the supernatant fluid from each compound concentration was collected on day 3 post infection (3 wells pooled) and tested for virus titer using a standard endpoint dilution $CCID_{50}$ assay and titer calculations using the Reed-Muench equation (1948) (Reed, L J and Muench, H. Am. *J. Hygiene* 27:493-497 (1948)) and the concentration of compound required to reduce virus yield by 90% ($EC_{90}$) was determined by regression analysis.

HAE Cell Preparations

The antiviral activities of test compounds were evaluated against SARS-CoV-2 (USA-WA1/2020) using made to order human airway epithelial (HAE) cells.

Cell Culture: HAE cells were grown on 6 mm mesh disks and arrived in kits with either 12- or 24-well transwell inserts. During transportation the tissues were stabilized on a sheet of agarose, which was removed upon receipt. One insert was estimated to consist of approximately $1.2 \times 10^6$ cells. Kits of cell inserts (EpiAirway™ AIR-100 or AIR-112) originated from a single donor, #9831, a 23-year old, healthy, non-smoking, Caucasian male. The cells form polarized monolayers, the apical side of which is exposed to air and creates a mucin layer. Upon arrival, the cell transwell inserts were immediately transferred to individual wells of a 6-well plate according to the manufacturer's instructions, and 1 mL of MatTek's proprietary culture medium (AIR-100-MM) was added to the basolateral side, whereas the apical side was exposed to a humidified 5% $CO_2$ environment. Cells were cultured at 37° C. in a humidified atmosphere containing 5% $CO_2$ for one day before the start of the experiment. After the 24-h equilibration period, the mucin layer, secreted from the apical side of the cells, was removed by washing with 400 μL pre-warmed 30 mM HEPES buffered saline solution 3×. Culture medium was replenished following the wash steps.

Viruses: Virus was diluted in AIR-100-MM medium before infection to yield a MOI when added to cultures of approximately 0.0015 $CCID_{50}$ per cell.

Experimental design: Each compound treatment (120 μL) and virus (120 μL) was applied to the apical side, and the compound treatment (1 mL) was applied to the basal side. As a virus control, some of the cells were treated with cell culture medium only. After a 2-h infection incubation, the apical medium was removed, and the basal medium was replaced with fresh compound or medium (1 mL). The cells were maintained at the air-liquid interface. On day 5, cytotoxicity ($CC_{50}$ values) in the uninfected, compound-treated inserts was estimated by visual inspection, and the basal medium was removed from all inserts and discarded. Virus released into the apical compartment of the HAE cells was harvested by the addition of 400 μL of culture medium that was pre-warmed at 37° C. The contents were incubated for 30 min, mixed well, collected, thoroughly vortexed and plated on Vero 76 cells for VYR titration. Separate wells were used for virus control and duplicate wells were used for untreated cell controls. Virus titers from each treated culture were determined as described above.

Example 7. Compound 1A Triphosphate Levels in Human Nasal and Bronchial Cells

Compound 1A (10 μM) was incubated in triplicate with human nasal and bronchial epithelial cells for 8 hours. At the end of the 8-hr exposure to individual test articles, the incubation medium was removed and the cell layer was washed with Hepes buffered saline solution (HBSS). HBSS was removed, followed by the addition of fresh cell culture medium without test article. At 0, 15, 24, 48, and 72 hours after the removal of test article, the extracellular medium was removed, and the cell layer was rinsed with HBSS. The cells were scraped off from plates and suspended in cold 60% methanol in water containing the internal standard AT 9005 and stored at ca. −20° C., followed by centrifugation for LC/MS/MS analysis for the formation of the corresponding triphosphate metabolite of Compound 1A, Compound 1-6 (Scheme 1). Table 6 provides the mean intracellular concentration of the triphosphate metabolite Compound 1-6 at each of the time points. FIG. 1 is a graph of the concentration of Compound 1-6 at each time point post-exposure in bronchial cells and nasal cells. The half-life ($t_{1/2}$) in nasal cells was 38 hours and 39 hours in bronchial cells. The triphosphate level in bronchial cells was greater than in nasal cells, but substantial levels of triphosphate were formed in both. The half-life in both cells was over 1.5 days and no toxicity was observed up to 100 μM.

TABLE 6

Intracellular Concentration of Triphosphate Concentrations in Bronchial and Nasal Cells

| Cell Type | Time After Washout (h) | Mean Intracellular Compound 1-6 Concentration (μM)[1] |
|---|---|---|
| Human bronchial | 0 | 698 |
|  | 15 | 560 |

TABLE 6-continued

Intracellular Concentration of Triphosphate
Concentrations in Bronchial and Nasal Cells

| Cell Type | Time After Washout (h) | Mean Intracellular Compound 1-6 Concentration ($\mu M$)[1] |
|---|---|---|
| epithelial cells | 24 | 462 |
|  | 48 | 290 |
|  | 72 | 217 |
| Human nasal | 0 | 236 |
| epithelial cells | 15 | 204 |
|  | 24 | 170 |
|  | 48 | 107 |
|  | 72 | 73.8 |

[1]Calculated using an average volume of 1320 microns$^3$ for alveolar type I and II epithelial cells (Crapo, J.D. et al. 1982 Am. Rev. Respir. Dis. 126(2): 332-7. doi: 10.1164/arrd.1982.126.2.332.)

Figure 2:
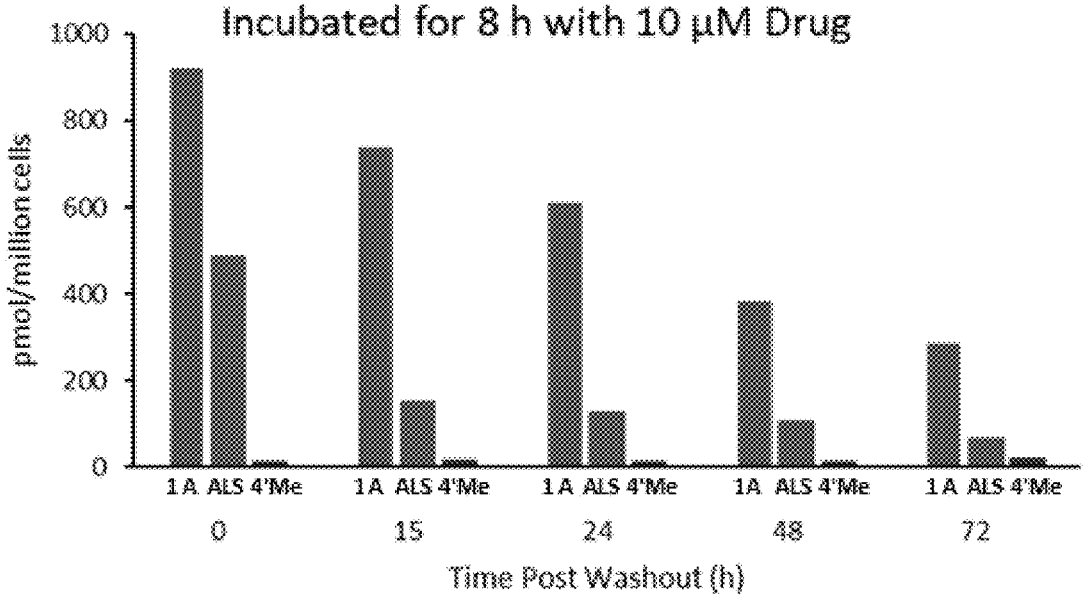
FIG. 2 is a graph comparing the triphosphate Compound 1-6 levels in human bronchial epithelial cells following exposure to Compound 1A (1A), ALS-8112 (ALS), and the 4'-Me substituted prodrug isopropyl ((S)-(((2R,3R,4R,5R)-5-(2-amino-6-(methylamino)-9H-purin-9-yl)-4-fluoro-3-hydroxy-2,4-dimethyltetrahydrofuran-2-yl)methoxy)(phenoxy)phosphoryl)-L-alaninate (4'-Me) as described in Example 7. The x-axis is the time post-washout measured in hours and the y-axis is the concentration of Compound 1-6 in pmol/million cells.
Figure 3:
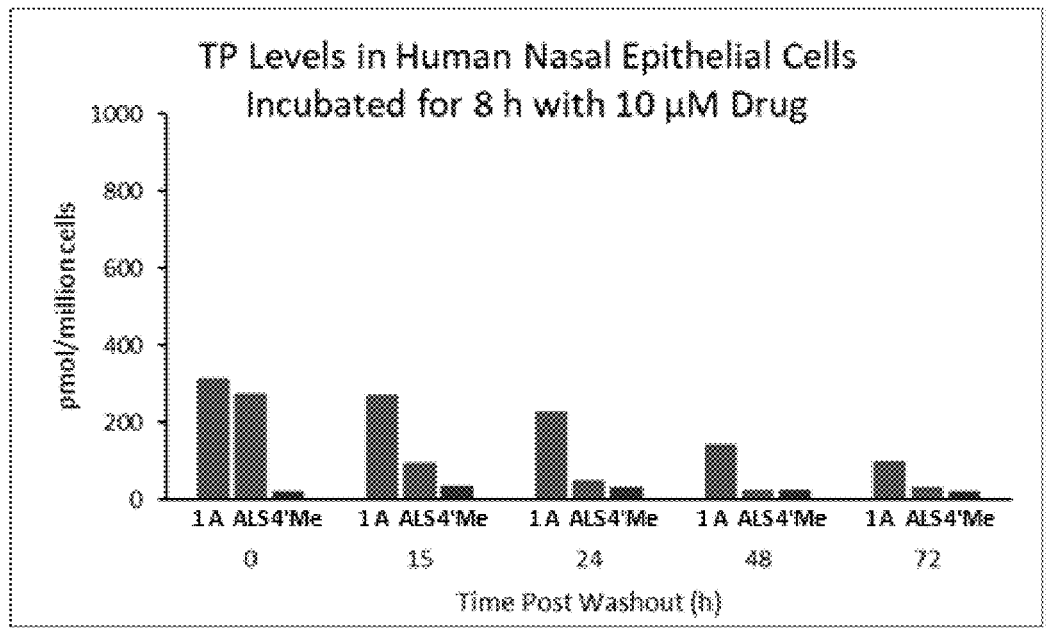
FIG. 3 is a graph comparing the triphosphate Compound 1-6 levels in human nasal epithelial cells following exposure to Compound 1A (1A), ALS-8112 (ALS), and 4'-Me substituted prodrug isopropyl ((S)-(((2R,3R,4R,5R)-5-(2-amino-6-(methylamino)-9H-purin-9-yl)-4-fluoro-3-hydroxy-2,4-dimethyltetrahydrofuran-2-yl)methoxy) (phenoxy)phosphoryl)-L-alaninate (4'-Me) as described in Example 7. The x-axis is the time post-washout measured in hours and the y-axis is the concentration of Compound 1-6 in pmol/million cells.

FIG. 2 and FIG. 3 are bar graphs of the triphosphate levels in bronchial and nasal cells, respectively, at each of the time points. FIGS. 2 and 3 compare the triphosphate level formed from Compound 1A to the triphosphate level formed from ALS-8112 (shown below) and the 4'-Me substituted prodrug (isopropyl ((S)-(((2R,3R,4R,5R)-5-(2-amino-6-(methylamino)-9H-purin-9-yl)-4-fluoro-3-hydroxy-2,4-dimethyltetrahydrofuran-2-yl)methoxy)(phenoxy)phosphoryl)-L-alaninate, shown below on the left). ALS-8112 is a clinically effective drug against RSV with an in vitro $EC_{90}$ of 1.3-2.7 $\mu M$ in RSV-infected HAE cells (Deval, J. et al. 2015 PLoS Pathog 11(6): e1004995).

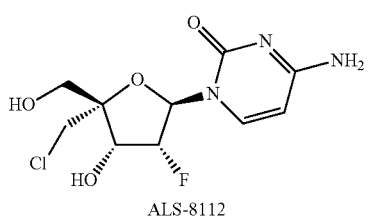

ALS-8112

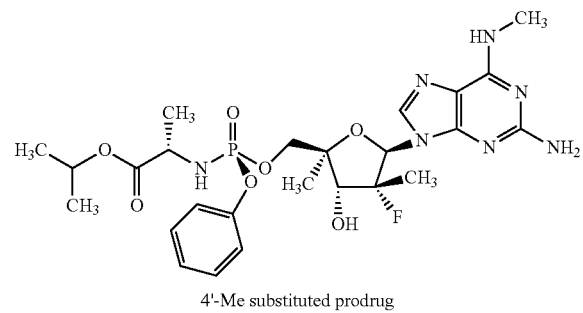

4'-Me substituted prodrug

As shown in FIGS. 2 and 3, substantially more triphosphate is formed from Compound 1A compared to ALS-8112 or the 4'-Me substituted prodrug in both human bronchial and nasal cells. At end of 8 hour incubation with each drug at a concentration of 10 $\mu M$, ratios of triphosphate from Compound 1A vs. ALS-8112 and the 4'-Me substituted prodrug were 2 and 84 in bronchial cells and 1 and 14 in nasal cells, respectively. Ratios of triphosphate from Compound 1A vs. ALS-8112 and the 4'-Me substituted prodrug were 5 and 54 in bronchial cells and 3 and 8 in nasal cells, respectively, 15 hours after washout.

Example 8. Triphosphate Levels in Tissues of Non-Human Primates after Oral Administration of Compound 2A Non-human primates were administered a three-day oral dosing regimen of Compound 2A to achieve steady state levels. The primates were given one 60 mg/kg dose followed by five 30 mg/kg doses every 12 hours (doses were allometrically scaled from clinical dosing regimen of 100 mg loading dose+550 mg twice a day (BID)).

The plasma PK of metabolites Compound 1A, Compound 1-2, and the triphosphate surrogate Compound 1-7 were determined. Just prior to the penultimate dose and at 0.5, 1, 2, 4, 6, 8 and 12 h (just prior to the last dose) thereafter, blood samples were obtained from 3 monkeys and mixed with EDTA. Plasmas were then prepared by centrifugation and analyzed for concentrations of Compound 1A, Compound 1-2, and Compound 1-7 by LC-MS/MS. (Triphosphate Compound 1-6 is produced in the cell and does not leave. It is therefore not measurable in the plasma. However, the 5'-OH metabolite Compound 1-7 (see Scheme 1) is exported from the cell, and therefore is measurable in plasma and can act as a surrogate for the intracellular active metabolite Compound 1-6.) The plasma PK data for the metabolites are given in Table 7.

TABLE 7

Plasma PK data for Metabolites 1A, 1-2, and 1-7 following Compound 2A Dosing

| | Mean Plasma Pharmacokinetic Parameters | | | | |
|---|---|---|---|---|---|
| Compound | $C_{max}$ ($\mu M$) | $C_{12\,h}$ ($\mu M$) | $T_{max}$ (h) | $T_{1/2}$ (h) | $AUC_{0-12\,h}$ ($\mu M * h$) |
| 1A (parent prodrug) | 0.64 | Not detected | 0.5-1 | 0.74 | 0.44 |
| 1-2 (intermediate prodrug) | 0.68 | 0.20 | 1-4 | 8.8 | 4.4 |
| 1-7 (plasma surrogate for intracellular TP) | 0.16 | 0.10 | 2 | 17 | 0.47 |

Figure 4:
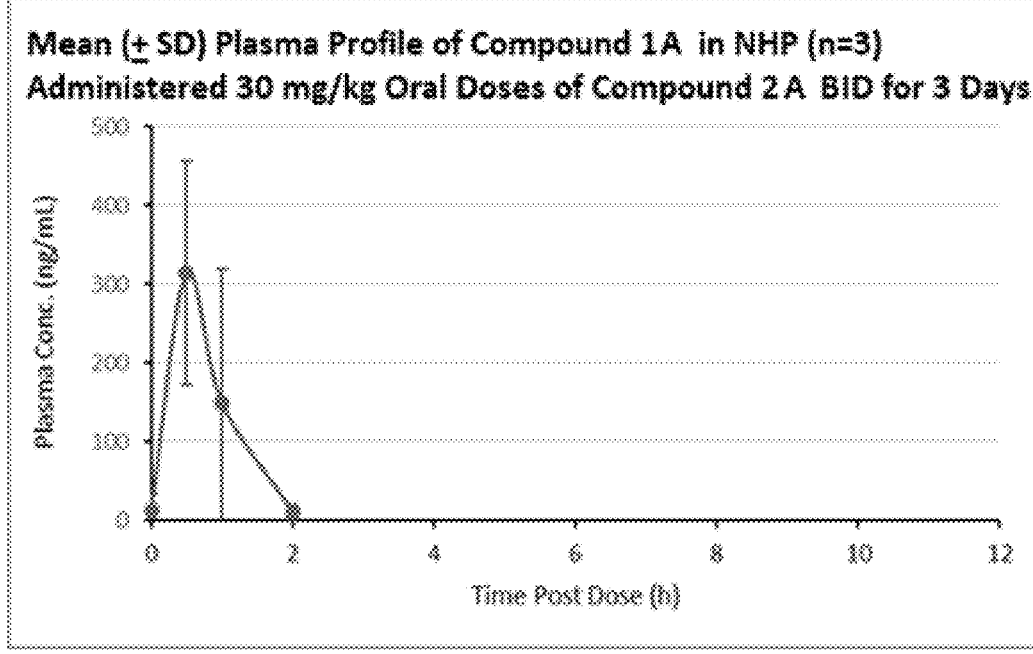
FIG. 4 is a graph of the mean plasma profile of Compound 1A in monkeys administered 30 mg/kg oral doses of Compound 2A twice a day (BID) for 3 days as described in Example 8. The x-axis is the time post-dose measured in hours and the y-axis is the plasma concentration of Compound 1A measured in ng/mL.
Figure 5:
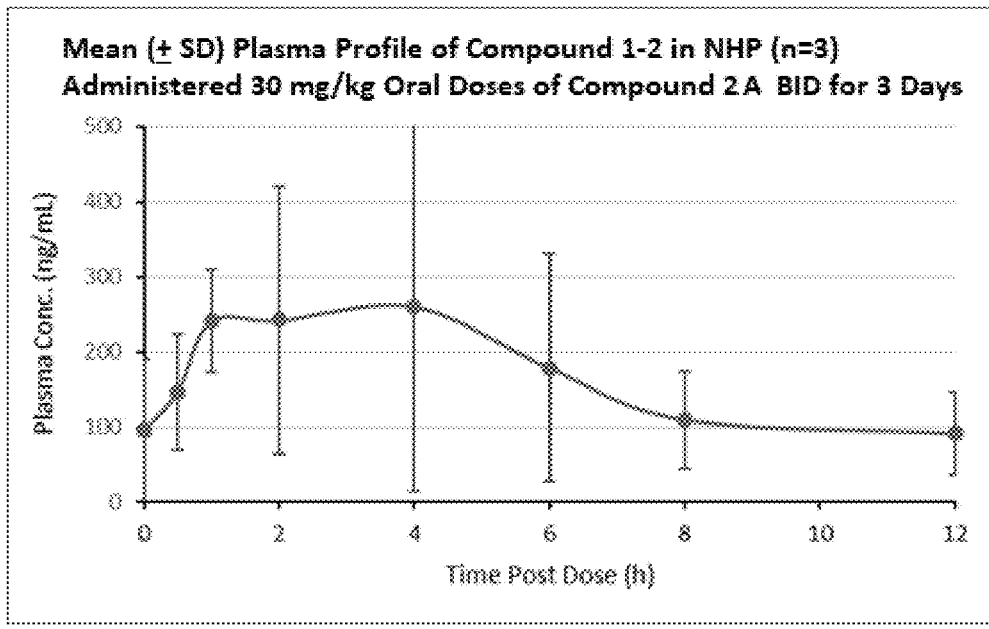
FIG. 5 is a graph of the mean plasma profile of metabolite Compound 1-2 in monkeys administered 30 mg/kg oral doses of Compound 2A twice a day (BID) for 3 days as described in Example 8. The x-axis is the time post-dose measured in hours and the y-axis is the plasma concentration of Compound 1-2 measured in ng/mL.
Figure 6:
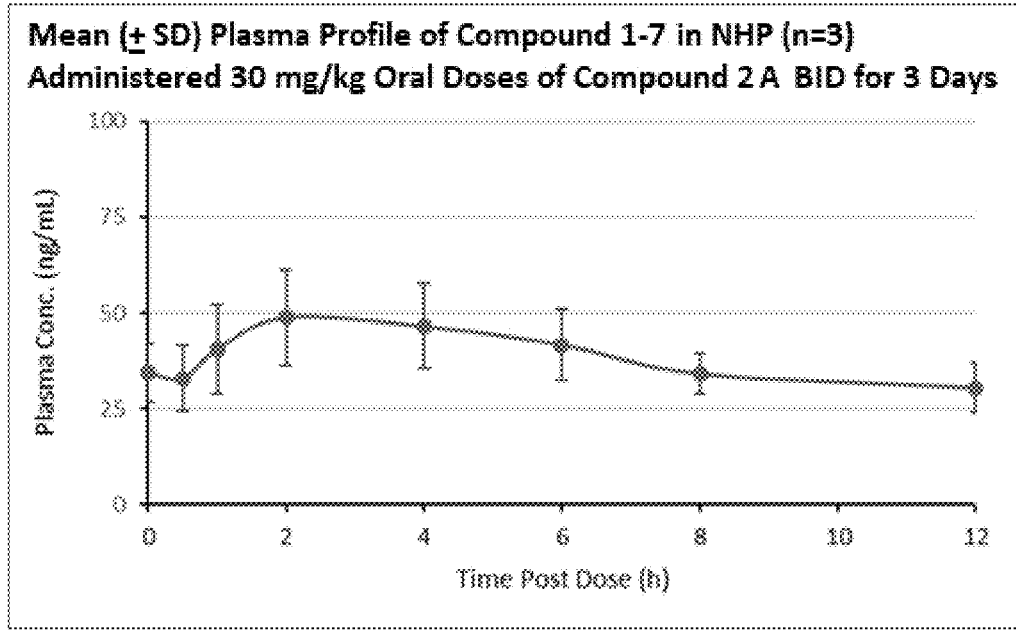
FIG. 6 is a graph of the mean plasma profile of triphosphate surrogate metabolite Compound 1-7 in monkeys administered 30 mg/kg oral doses of Compound 2A twice a day (BID) for 3 days as described in Example 8. The x-axis is the time post-dose measured in hours and the y-axis is the plasma concentration of Compound 1-7 measured in ng/mL.

FIGS. 4, 5, and 6 are graphs of the mean plasma profile of Compound 1A, Compound 1-2, and Compound 1-7, respectively, in the non-human primates following administration of oral doses of Compound 2A (30 mg/kg BID for 3 days). Plasma trough concentrations (mean of 0- and 12 h time points) for Compound 1-2 (intermediate prodrug) and Compound 1-7 (surrogate for intracellular TP levels) are 0.20 and 0.11 $\mu M$, respectively. The profiles show rapid conversion of Compound 1A to Compound 1-2 and Compound 1-7 (a surrogate for triphosphate Compound 1-6).

Figure 7:
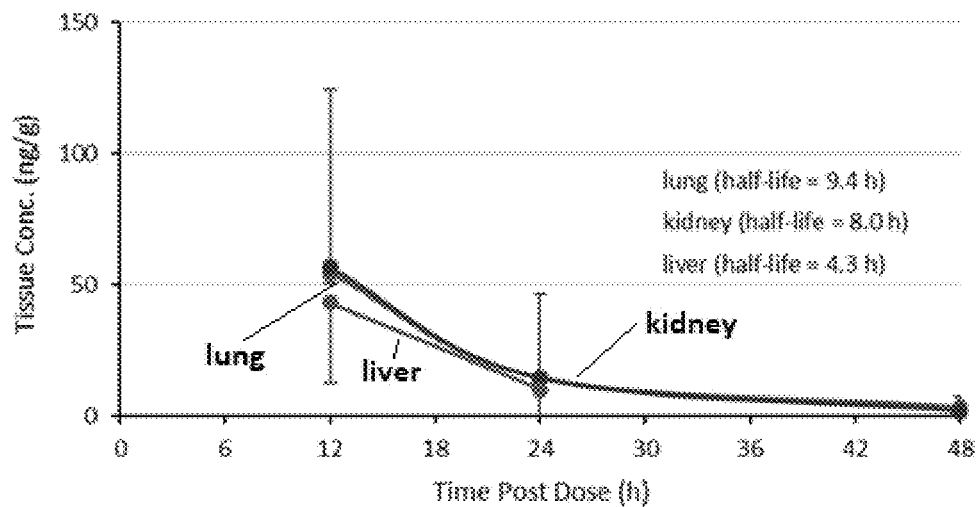
FIG. 7 is a graph of the triphosphate Compound 1-6 concentration in lung, kidney, and liver tissue in monkeys following administration of 30 mg/kg oral doses of Compound 2A twice a day (BID) for 3 days as described in Example 8. The half-life in the lung, kidney, and liver was 9.4 hours, 8.0 hours, and 4.3 hours, respectively. The x-axis is the time post-dose measured in hours and the y-axis is the tissue concentration of Compound 1-6 measured in ng/g.

Lung, kidney, and liver tissue levels were next determined for triphosphate Compound 1-6, Compound 1A, and other metabolites at 12, 24, and 48 hours post last dose (3 males per time point) as shown in FIG. 7. As described above, three male non-naïve cynomolgus monkeys were administered a 60 mg/kg loading dose followed by five 30 mg/kg doses every 12 h of Compound 2A. Samples of plasma, lung, kidney and liver tissue were collected at 12, 24, and 48 hours post last dose from the three anesthetized animals at each time point and immediately flash-frozen in liquid nitrogen. Approximately 0.5 g of each sample of tissue was homogenized using a Polytron in 5 volumes (5 mL/g) 70% methanol:30% 268 mM EDTA adjusted to pH 7.8 and containing appropriate internal standards in tubes immersed in a dry ice:ethanol bath. Homogenates were analyzed for concentrations of Compound 1A, Compound 1-2, Compound 1-6, and Compound 1-7 by LC-MS/MS.

The trough (12 h) levels of active metabolite triphosphate Compound 1-6 in lung, kidney and liver non-human primate tissues 12 hours after the last dose of Compound 2A was 0.14 μM, 0.13 μM, and 0.09 μM, respectively. (This corresponds to 55 ng/g (lung), 57 ng/g (kidney), and 43 ng/g (liver)). The triphosphate species concentration was 1.6-fold greater in the lung compared to the liver at 12-hour steady-state trough levels. Plasma tough level of Compound 1-7, the surrogate for Compound 1-6 in plasma, was 39 ng/mL. Table 8 provides the mean intracellular concentration of the triphosphate metabolite Compound 1-6 in lung, kidney, and liver tissue at each of the time points. As shown in FIG. 7, the half-life of Compound 1-6 in lung, kidney, and liver was 9.4 hours, 8.0 hours, and 4.3 hours, respectively. The half-life of Compound 1-6 was determined by dividing ln(2) by k, the rate constant for the decrease in Compound 1-6 concentration obtained from the slope of the plot of ln (tissue concentration) vs. time after linear regression analysis.

TABLE 8

Intracellular Concentration of Compound 2A Triphosphate Concentrations in Lung, Kidney, and Liver Cells

| Tissue | Time Post Last Dose (h) | Mean Intracellular Compound 1-6 Concentration (μM)[1] |
|---|---|---|
| Lung | 12 | 0.14 |
|  | 24 | 0.037 |
|  | 48 | 0.009 |
| Kidney | 12 | 0.13 |
|  | 24 | 0.032 |
|  | 48 | 0.004 |
| Liver | 12 | 0.089 |
|  | 24 | 0.021 |
|  | 48 | Not Detected |

[1]Calculated using non-interstitial volumes of 0.75 and 0.9 mL/g lung and liver, respectively, and an assumed volume of 0.83 mL/g kidney (Mandikian, D. et al. 2018 AAPS Journal 20(6):107. doi.org/10.1208/s12248-018-0264-z.)

Figure 8:
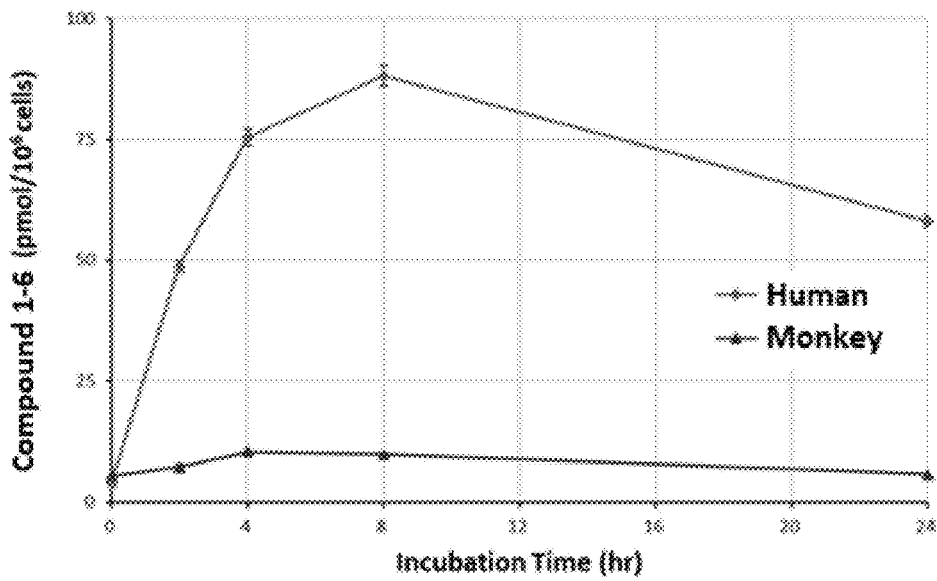
FIG. 8 is a graph of levels of triphosphate Compound 1-6 in hepatocytes incubated with Compound 2A as described in Example 9 and previously described in from Good, S. S. et al. 2020 PLoS ONE 15(1):e0227104. The concentration was 7 times higher in human hepatocytes than in monkeys. The x-axis is the incubation time measured in hours and the y-axis is the Compound 1-6 concentration measured in pmol/$10^6$ cells.
Figure 9:
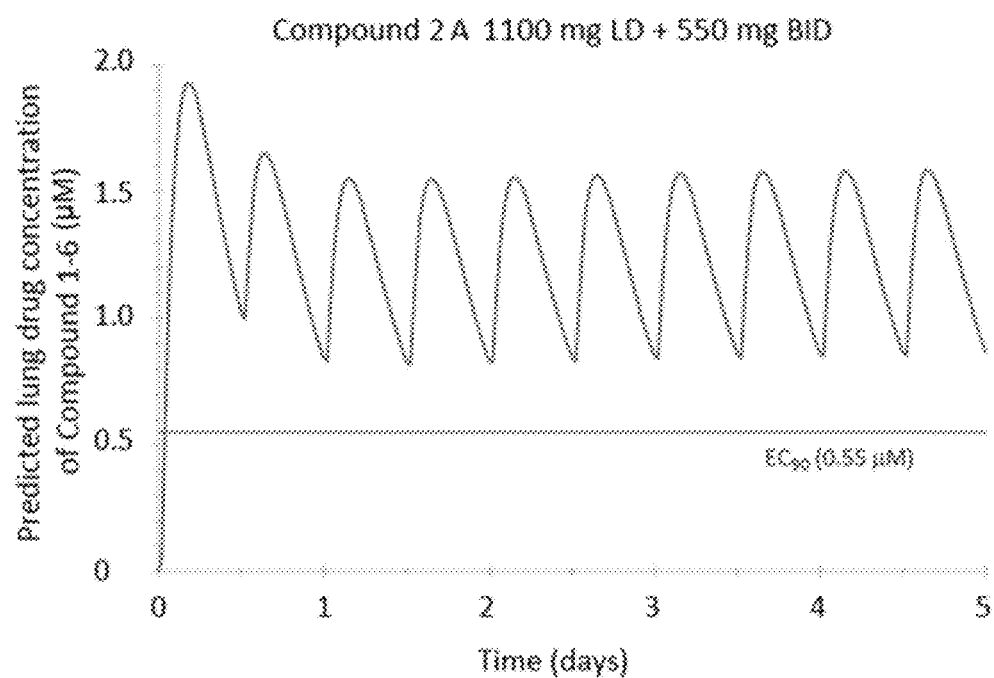
FIG. 9 is the simulation of intracellular concentrations of Compound 1-6 in human lung tissue as described in Example 10. The predicted lung concentration is based on predicted trough ($C_{12h}$) steady-state plasma Compound 1-7, a plasma surrogate for intracellular triphosphate Compound 1-6, (Berliba, e. et al. 2019 Antimicrob. Agents Chemother. 63(12):e01201-19) in humans multiplied by a ratio of 1.6 (the triphosphate concentration in the lung is 1.6 times greater than in the liver at steady-state trough levels as described in Example 8). The x-axis is time measured in days and the y-axis is simulated lung Compound 1-6 concentration measured in M.
Figure 10:
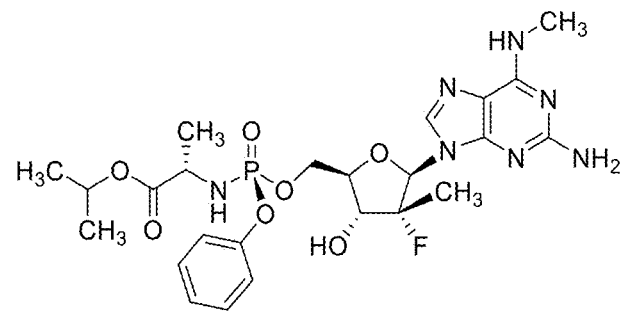
FIG. 10 is an illustration of an active compound according to the present invention, which can be administered as a pharmaceutically acceptable salt.

Example 9. Prediction of Human Lung and Kidney Concentrations of Triphosphate Compound 1-6 Based on Compound 1-6 Tissue Levels in Non-Human Primates As described in (Good, S. S. et al. 2020 PLoS ONE 15(1):e0227104), the levels of triphosphate Compound 1-6 in human and monkey hepatocytes incubated with 10 μM of Compound 1A were determined. FIG. 8 is a graph comparing the levels in the two species, and as shown in the Figure, triphosphate Compound 1-6 concentrations in human hepatocytes is 7-fold greater than in non-human primate (monkey) hepatocytes assessed by $AUC_{0-24}$ values. The data is also presented in Table 9.

TABLE 9

Intracellular Concentration of Triphosphate Concentrations in Monkey and Human Hepatocytes

| Species | Incubation Time (h) | Mean Intracellular Compound 1-6 Concentration (μM)[1] |
|---|---|---|
| Non-human Primate | 2 | 2.1 |
|  | 4 | 3.1 |

TABLE 9-continued

Intracellular Concentration of Triphosphate Concentrations in Monkey and Human Hepatocytes

| Species | Incubation Time (h) | Mean Intracellular Compound 1-6 Concentration (μM)[1] |
|---|---|---|
|  | 8 | 2.9 |
|  | 24 | 1.7 |
| Human | 2 | 14 |
|  | 4 | 22 |
|  | 8 | 26 |
|  | 24 | 17 |

[1]Calculated using a hepatocyte volume of $3.4 \times 10^{-9}$ mL (Lodish, H. et al. 2000 Molecular Cell Biology (fifth edition), W.H. Freeman and Co., New York. P. 10.

Based on the ratio (7.0) of human to monkey concentrations of triphosphate Compound 1-6 as assessed by its in vitro formation in primary hepatocytes, the predicted human tissue level was determined. The actual tissue levels of triphosphate Compound 1-6 in monkeys and the predicted tissue levels in humans is shown in Table 10. A clinical dosing regimen of 1100 mg LD (loading dose)+550 mg BID (twice a day) is predicted to achieve lung intracellular levels of triphosphate Compound 1-6 at trough (12 h) above the in vitro $EC_{90}$ of Compound 2A against SARS-CoV-2 replication in HAE cell cultures. Triphosphate levels during this dosing regimen are predicted to consistently remain above the in vitro $EC_{90}$ of Compound 2A against SARS-CoV-2. Predictions are conservative (at least for the lung) because the ling triphosphate half-life in human bronchial/nasal cells (38 hours) as compared to the non-human primate lung tissue (9.4 hours) predicts higher steady-state levels in humans with BID dosing, but this was not factored into predictions.

TABLE 10

Actual (Monkey) and Predicted (Human) Tissue Levels of Compound 1-6

| | Intracellular Triphosphate 1-6 Conc. at 12 hours Post-dose (μM) | | |
|---|---|---|---|
| Species | Liver | Kidney | Lung |
| Non-human primate | 0.089 | 0.13 | 0.14 |
| Human | 0.62 | 0.91 | 0.98 |

Example 10. Simulation of Intracellular Concentrations of Triphosphate Compound 1-6 in Human Lung Tissue Plasma conc-time profiles of Compound 1-7 (a surrogate for triphosphate Compound 1-6 because Compound 1-6 cannot be measured in plasma) was obtained from subjects (N=18) who received 600 mg QD dose of Compound 2A (equivalent to 553 mg of free base Compound 1A) for 7 days as part of the AT-01B-001 study (as described in FIG. 1 and Table 3 of Berliba, e. et al. 2019 Antimicrob. Agents Chemother. 63(12):e01201-19). The profiles were subjected to population pharmacokinetic (PPK) analysis using Monolix Suite 2019 Suite 2019 (Lixosoft, Antony, France). The obtained PPK parameters together with the associated variance and covariance matrices were then used to simulate, using the Simulx module of Monolix Suite, plasma PK profiles of Compound 1-7 for various dosing regimens.

It was assumed that 1) lung triphosphate levels of Compound 1-7 were 1.6 the plasma levels of its nucleoside metabolite Compound 1-7 based on the ratio obtained in monkeys for lung-to-liver concentrations of Compound 1-6; and 2) the average in vitro $EC_{90}$ of Compound 1A against SARS-CoV-2 was about 0.55 uM in HAE cell preparations. Under these assumptions, the simulated lung Compound 1-6 levels would exceed the in vitro $EC_{90}$ shortly after administration of a loading dose of 1100 mg and remain above $EC_{90}$ with the 550 BID maintenance doses for the remaining days. The simulated lung Compound 1-6 concentration over the course of 5 days is shown in FIG. 9.

Example 11. Formulation Description and Manufacturing of Compound 2A

A representative non-limiting batch formula for Compound 2A tablets (50 mg and 100 mg) is presented in Table 11. The tablets were produced from a common blend using a direct compression process. The active pharmaceutical ingredient (API) was adjusted based on the as-is assay, with the adjustment made in the percentage of microcrystalline cellulose. The API and excipients (microcrystalline cellulose, lactose monohydrate, and croscarmellose sodium) were screened, placed into a V-blender (PK Blendmaster, 0.5 L bowl) and mixed for 5 minutes at 25 rpm. Magnesium Stearate was then screened, added and the blend was mixed for an additional 2 minutes. The common blend was divided for use in producing 50 mg and 100 mg tablets. The lubricated blend was then compressed at a speed of 10 tablets/minutes using a single punch research tablet press (Korsch XP1) and a gravity powder feeder. The 50 mg tablets were produced using round standard concave 6 mm tooling and 3.5 kN forces. The 100 mg tablets were produced using 8 mm round standard concave tooling and 3.9-4.2 kN forces.

TABLE 11

Formulation of 50 mg and 100 mg Compound 2 Tablets

| | | | Mg/unit | |
|---|---|---|---|---|
| Raw Material | % w/w | g/batch | 50 mg Tablet | 100 mg Tablet |
| Compound 2A | 50.0 | 180.0 | 50.0 | 100.0 |
| Microcrystalline Cellulose, USP/NF, EP | 20.0 | 72.0 | 20.0 | 40.0 |
| Lactose Monohydrate, USP/NF, BP, EP, JP | 24.0 | 86.4 | 24.0 | 48.0 |
| Croscarmellose Sodium, USP/NF, EP | 5.0 | 18.0 | 5.0 | 10.0 |
| Magnesium Stearate, USP/NF, BP, EP JP | 1.0 | 3.6 | 1.0 | 2.0 |
| Total | | | 100.0 | 200.0 |

Compound 2A was adjusted based on the as-is assay, with the adjustment made in the percentage of microcrystalline cellulose. Compound 2A and excipients (microcrystalline cellulose, lactose monohydrate, and croscarmellose sodium) were screened, placed into a V-blender (PK Blendmaster, 0.5 L bowl) and mixed for 5 minutes at 25 rpm. Magnesium stearate was then screened, added and the blend was mixed for an additional 2 minutes. The common blend was divided for use in producing 50 mg and 100 mg tablets. The lubricated blend was then compressed at a speed of 10 tablets/minutes using a single punch research tablet press (Korsch XP1) and a gravity powder feeder. The 50 mg tablets were produced using round standard concave 6 mm tooling and 3.5 kN forces. The 100 mg tablets were produced using 8 mm round standard concave tooling and 3.9-4.2 kN forces. The specifications of the 50 mg and 100 mg tablets are shown in Table 12.

TABLE 12

Specifications of 50 mg and 100 mg Tablets of Compound 2A

| | 50 mg Tablets | 100 mg Tablets |
|---|---|---|
| Average Weight (n = 10) | 100 ± 5 mg | 200 ± 10 mg |
| Individual Weight | 100 ± 10 mg | 200 ± 20 mg |
| Hardness | 5.3 kp | 8.3 kp |
| Disintegration | <15 minutes | <15 minutes |
| Friability | NMT 0.5% | NMT 0.5% |

The 50 mg and 100 mg tablets produced as described above were subjected to 6 month stability studies under three conditions: 5° C. (refrigeration), 25° C./60% RH (ambient), and 40° C./75% RH (accelerated). Both the 50 mg and 100 mg tablets were chemically stable under all three conditions tested.

Under refrigeration conditions (5° C.), both the 50 mg and 100 mg tablets remained white solids that did not change in appearance from T=0 to T=6 months. Throughout the 6-month study, no impurities were reported that were greater than 0.05% for either the 50 mg tablets or the 100 mg tablets. The water content after 6 months was also less than 3.0% w/w for both tablets. Similar results were reported when the tablets were subjected to ambient conditions (25° C./60% RH); no impurities that were greater than 0.05% were reported throughout the 6 months for both tablets and the water content did not exceed 3.0% w/w at the 6-month mark. When the tablets were subjected to accelerated conditions (40° C./75% RH), the appearance of the 50 mg and 100 mg tablets did not change from a white, round tablet. One impurity was reported after 3 months, but the impurity was only 0.09%. A second impurity was reported after 6 months, but the total impurity percentage was only 0.21% for both the 50 mg and 100 mg tablets. Water content was 3.4% w/w at 6 months for the 50 mg tablets and 3.2% w/w for the 100 mg tablets.

In a separate study, the stability of 50 mg and 100 mg tablets of Compound 2A at ambient conditions (25° C./60% RH) was measured over 9 months. The appearance of the 50 mg and 100 mg tablet did not change from a white round tablet over the course of 9 months. Impurities in the 50 mg tablet were less than 0.10% after 9 months and impurities in the 100 mg tablet were less than 0.05%. The water content of the 50 mg tablet and the 100 mg tablet after 9 months was only 2.7% w/w and 2.6% w/w, respectively.

This specification has been described with reference to embodiments of the invention. Given the teaching herein, one of ordinary skill in the art will be able to modify the invention for a desired purpose and such variations are considered within the scope of the invention.

What is claimed is:

1. A method for the treatment of a coronavirus in a human in need thereof comprising administering an effective amount of Compound 1:

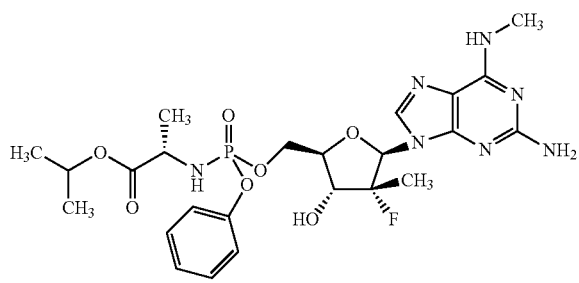 [SMILES: CNc1nc(N)nc2c1ncn2[C@@H]1O[C@H](COP(=O)(N[C@@H](C)C(=O)OC(C)C)Oc2ccccc2)[C@@H](O)[C@@]1(C)F]

or a pharmaceutically acceptable salt thereof, optionally in a pharmaceutically acceptable carrier.

2. The method of claim 1, comprising administering an effective amount of Compound 1A

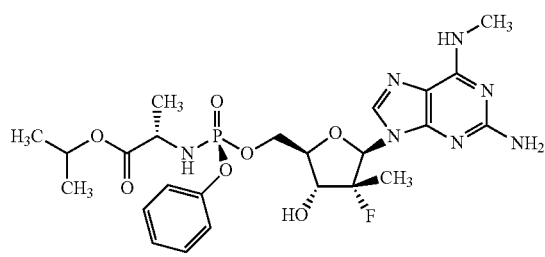 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

or a pharmaceutically acceptable salt thereof, optionally in a pharmaceutically acceptable carrier.

3. The method of claim 1, wherein the coronavirus is an alphacoronavirus.

4. The method of claim 3, wherein the alphacoronavirus is HCoV-229E.

5. The method of claim 1, wherein the coronavirus is a betacoronavirus.

6. The method of claim 5, wherein the betacoronavirus is HCoV-OC43.

7. The method of claim 1, wherein the pharmaceutically acceptable carrier is a dosage form suitable for oral administration.

8. The method of claim 2, wherein the pharmaceutically acceptable carrier is a dosage form suitable for oral administration.

9. The method of claim 7, wherein the dosage form is a solid dosage form.

10. The method of claim 8, wherein the dosage form is a solid dosage form.

11. The method of claim 9, wherein the solid dosage form is a tablet, capsule or gelcap.

12. The method of claim 10, wherein the solid dosage form is a tablet, capsule or gelcap.

13. The method of claim 2, wherein the pharmaceutically acceptable carrier is a dosage form suitable for intravenous delivery.

14. The method of claim 7, wherein the dosage form is a solution or a suspension for oral delivery.

15. The method of claim 1, comprising administering an effective amount of Compound 2

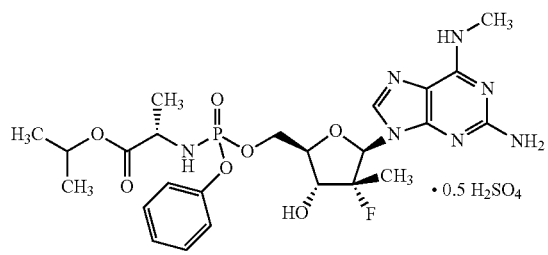 [SMILES: CNc1nc(N)nc2c1ncn2[C@@H]1O[C@H](COP(=O)(N[C@@H](C)C(=O)OC(C)C)Oc2ccccc2)[C@@H](O)[C@@]1(C)F]

optionally in a pharmaceutically acceptable carrier.

16. The method of claim 2, comprising administering an effective amount of Compound 2A

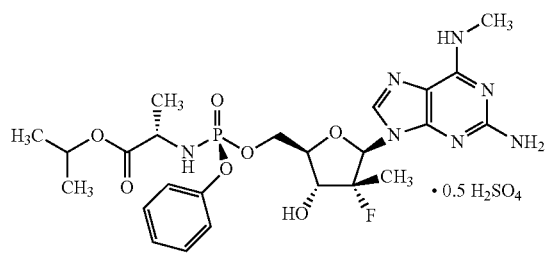 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

optionally in a pharmaceutically acceptable carrier.

17. The method of claim 16, comprising administering about 600 mg of Compound 2A hemisulfate salt:

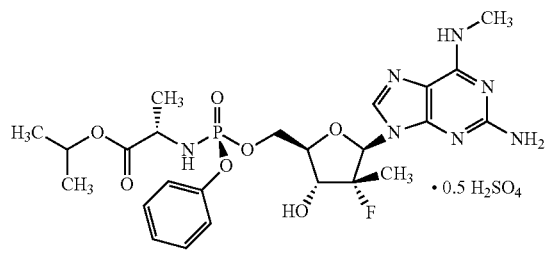 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

in an oral dosage form twice a day to a human in need thereof.

* * * * *